United States Patent
Gordon

(10) Patent No.: US 11,105,801 B2
(45) Date of Patent: Aug. 31, 2021

(54) BIOANALYTE SIGNAL AMPLIFICATION AND DETECTION WITH ARTIFICIAL INTELLIGENCE DIAGNOSIS

(71) Applicant: Neil Gordon, Hampstead (CA)

(72) Inventor: Neil Gordon, Hampstead (CA)

(*) Notice: Subject to any disclaimer, the term of this patent is extended or adjusted under 35 U.S.C. 154(b) by 140 days.

(21) Appl. No.: 16/125,602

(22) Filed: Sep. 7, 2018

(65) Prior Publication Data
US 2019/0079084 A1 Mar. 14, 2019

Related U.S. Application Data

(60) Provisional application No. 62/556,350, filed on Sep. 9, 2017.

(51) Int. Cl.
| | |
|---|---|
| *C12Q 1/68* | (2018.01) |
| *G01N 33/53* | (2006.01) |
| *C07H 21/00* | (2006.01) |
| *G01N 33/543* | (2006.01) |
| *C12Q 1/682* | (2018.01) |

(52) U.S. Cl.
CPC ....... *G01N 33/54366* (2013.01); *C12Q 1/682* (2013.01); *G01N 33/5438* (2013.01); *G01N 33/54386* (2013.01)

(58) Field of Classification Search
CPC .......... C12Q 1/68; G01N 33/53; C07H 21/00
See application file for complete search history.

(56) References Cited

U.S. PATENT DOCUMENTS

| 9,624,532 B2* | 4/2017 | Gordon | C12Q 1/6804 |
|---|---|---|---|
| 2009/0298703 A1* | 12/2009 | Gough | G06T 7/0012 |
| | | | 506/8 |
| 2010/0081134 A1* | 4/2010 | Mirkin | C12Q 1/6816 |
| | | | 435/6.11 |
| 2015/0141272 A1* | 5/2015 | Gordon | C12Q 1/6804 |
| | | | 506/9 |
| 2018/0106791 A1* | 4/2018 | Gordon | C12Q 1/6825 |
| 2019/0079084 A1* | 3/2019 | Gordon | G01N 33/54366 |

FOREIGN PATENT DOCUMENTS

| CA | 2954115 A1 * | 4/2018 | ............. C07H 21/00 |
|---|---|---|---|
| WO | WO-2018068134 A1 * | 4/2018 | ........... C12Q 1/6825 |
| WO | WO-2019046964 A1 * | 3/2019 | ....... G01N 33/54366 |

OTHER PUBLICATIONS

Gordon N., Universal Bioanalyte Signal Amplification for Electrochemical Biosensor. Biosensor J. 5: 1 (Year: 2016).*
Heineman et al., Strategies for Electrochemical Immunoassay. Analytical Chemistry 57(12) :1321A (Year: 1985).*
Jayamonohan et al., Highly Sensitive Bacteria Quantification Using Immunomagnetic Separation and Electrochemical Detection of Guanine-Labeled Secondary Beads.Sensors 15 : 12034 (Year: 2015).*
Ronkainen et al., Electrochemical biosensors. Chemical Society Reviews 39 : 1747 (Year: 2010).*
Wang et al., DNA-Based Amplified Bioelectronic Detection and Coding of Proteins. Agnew. Int. Ed. 43 :2158 (Year: 2004).*
Wang et al., Sensitive Immunoassay of a Biomarker Tumor Necrosis Factor-r Based on Poly(guanine)-Functionalized Silica NanoparticleLabel. Analytical Chemistry 78 : 6974 (Year: 2006).*
Kulikowski, CA., Artifical Intelligence Methods and Systems for Medical Consultation. IEEE Transactions vol. PAMI-2, No. 5 (SEP) (Year: 1980).*

* cited by examiner

Primary Examiner — Ethan C Whisenant

(57) ABSTRACT

This invention discloses a signal amplification sandwich structure for amplifying detection signals from proteins, nucleic acids and microbes using a plurality of an electrochemically detectable oligonucleotide tag bound to a multifunctional particle. The invention further discloses a method and device that uses the signal amplification sandwich structure to detect and/or quantify low levels of one or more biological analytes using an off-the-shelf point-of-care electrochemical potentiostat, like a glucose meter for virtually any biological analyte. The invention further discloses a method and device that applies an artificial intelligence (AI) system to recommend actions for assessment and diagnosis of a disease, outbreak or condition with an artificial intelligence learning system to incorporate improvements, additions and modifications to the artificial intelligence systems and its constituents.

21 Claims, 18 Drawing Sheets

Specification includes a Sequence Listing.

BIOANALYTE SIGNAL AMPLIFICATION AND DETECTION WITH ARTIFICIAL INTELLIGENCE DIAGNOSIS

CROSS-REFERENCE TO RELATED APPLICATIONS

This application claims benefit under 35 U.S.C. § 119(e) of U.S. provisional patent application Ser. No. 62/556,350 titled "Electrochemical signal amplification, detection and quantification of bioanalytes", filed on Sep. 9, 2017, which, including all figures and tables, is incorporated herein by reference in its entirety.

This application refers to a sequence listing, which is provided as an electronic document filename "ElectrochemicallyDetectableOligoTags1_ST25", 2710 bytes in size, created on Feb. 11, 2021, and which is incorporated herein by reference in its entirety.

FIELD OF THE INVENTION

The present invention relates generally to the field of biological assays. More particularly, the invention relates to devices and methods that allow ultra-low levels of virtually any biological analyte to be amplified, detected and quantified rapidly, simply and inexpensively, then diagnosed for diseases, outbreaks and conditions with artificial intelligence.

BACKGROUND OF THE INVENTION

The following discussion of the background of the invention is merely provided to aid the reader in understanding the invention and is not admitted to describe or constitute prior art to the present invention. All references, including publications, patent applications, and patents, cited herein are incorporated by reference in full to the same extent as if each individual publication was specifically and individually indicated to be incorporated by reference.

The analysis of biological analytes (also referred to as bioanalytes and analytes) is critical for human health, safety and the environment. For example, infectious diseases can be diagnosed and treated by identifying the specific causes of the disease. This can be done by analyzing bodily samples using biological assays for the presence of disease-causing biological analytes including cells such as bacteria, protozoa and fungi, virus particles, toxins caused by the infectious materials, as well as biomolecular constituents of the infectious materials such as DNA, RNA and proteins.

Diseases, cancers and medical conditions such as cardiac arrest can be identified by the presence and levels of protein antigens and antibodies produced by the human immune system or other bodily mechanism. Genetic markers can also be used to indicate an abnormal state or predisposition to diseases, cancers and medical conditions. Hazardous biological materials can also be transmitted by infected food, plants, water, air, objects such as surfaces or containers, insects, birds, fish, lizards, rodents, animals, and people. Samples can be analyzed for pathogenic cells, virus particles, protein toxins, and biomolecules such as nucleic acids and proteins. Some hazardous biological materials are naturally occurring while others can be intentionally released by bioterrorists. Many other applications and sectors such as biotechnology, pharmaceutical, and forensic also require analysis for the identification, presence and levels or concentrations of biological analytes. Accurate, timely and practical analysis of biological analytes is extremely complex. Some analytes can be present as substances that are difficult and costly to accurately assay. Some analytes are not specific to a single disease, cancer, or medical condition, and some diseases, cancers and medical conditions are not specific to a single analyte. Therefore identification of analytes can require multiplex assays for multiple analytes and in some cases multiple types of analytes for confirmation.

Some analytes can be present in extremely low levels and may not be detected by an assay, resulting in false negative outcomes. This requires highly sensitive assays that can detect low levels and typically the additional use of an amplification or enrichment process to increase the number of analytes before assaying. Some analytes can be surrounded by nonspecific materials in several orders of magnitude greater levels, as well as nonspecific materials comprising nonspecific strains and species of the target analyte which are physically and chemically similar. Nonspecific materials can prevent the analytes from being detected by an assay, and result in false negative outcomes. In the case where the analyte is not present in the sample, the nonspecific material may be incorrectly detected as a bioanalyte by the assay, causing a false positive outcome. This requires highly specific assays and preferably the additional use of a purification process to remove nonspecific materials before assaying. Even though some analytes may be present in a sample and correctly detected by the assay, some analytes can have an abnormal or harmful level which is higher or lower than a normal level. Some analytes have levels that change over time. This requires assays that can quantify analyte levels or concentrations, accurately and frequently.

Some analytes are highly infectious, extremely harmful, and costly to treat or remediate. These analytes need to be analyzed in a very timely manner to minimize the transmission of the infection. As well, some analytes have an elevated level for a limited period of time. Some assay operators have limited technical proficiency and need assays that are automated and easy to use. Some testing organizations have budgetary constraints and require assays to be low cost for consumables, labor, sample collection, assay equipment and laboratory facilities.

Numerous assays are known for detecting biological analytes in a sample. Four general types of biological analytes are cells, nucleic acids, proteins and redox active species. The technologies and assays directed at detecting these analytes are basically separate and independent. In certain cases different technologies can be used to measure the presence of analytes associated with the same disease. As an example, Table 1 illustrates the relative limits of detection and turnaround times for selected commercial products that use cell cultures, nucleic acid amplification tests and protein immunoassays for detecting analytes associated with certain infectious diseases. Cell cultures and nucleic acid amplification tests have the lowest limits of detection but also have longer turnaround times because of the test complexity, labor-intensity, and laboratory logistics of preparing samples, replicating analytes and performing the assays. Protein immunoassays can be done in laboratories, and are also available as simple rapid point-of-care tests that have a higher limit of detection.

TABLE 1

Relative Limits of Detection and Turnaround Times of
Different Detection Technologies Used by Commercial Products

| Analyte | Cell Culture | Nucleic Acid Amplification Test | Protein Immunoassay (Lab Test) | Protein Immunoassay (POC Test) |
|---|---|---|---|---|
| | | Limit of Detection | | |
| C. difficile Toxin Protein | 1 pg/mL | 10 pg/mL | 300 pg/mL | 1000 pg/mL |
| Campylobacter C. jejuni Bacteria | $3 \times 10^2$ cfu/mL | $3 \times 10^3$ cfu/mL | $3 \times 10^6$ cfu/mL | $3 \times 10^7$ cfu/mL |
| HIV Virus | Not applicable to viruses | ~15 virions/mL | ~3000 virions/mL | >>3000 virions/mL |
| | | Turnaround Time | | |
| Time between sample and test result | 2-7 days | 1-2 days | 1-2 days | 5-60 min |

Cell assays employ viable cells to reproduce outside of their natural environment to amplify the detection signals. Targets cells reproduce in a growth media incubated at an appropriate temperature, gas mixture and pH. Materials can be included to suppress the growth of nonspecific cells. Detectable dyes provide color which intensifies with an increasing number of cells. Cell cultures are sensitive assays, but have a slow turnaround time (2-7 days) for producing a detectable number of cell colonies, and can result in false positive results caused by nonspecific strains of the target cells that reproduce in the growth media. Cell assays can fail if target cells are unable to reproduce due to cells being dead or injured, or from contamination of the growth media. Because of the labor-intensive processing, cell assays can also fail from technician error due to an incorrect manual process, or from an inability to distinguish target cells from non-specific materials.

Nucleic acid assays cause a target region of DNA strands to amplify using polymerase chain reaction (PCR) during repeated thermally-induced biochemical processes. DNA fragments are exposed to appropriate denaturing conditions including high temperature to melt double helix DNA into single DNA strands. The temperature is lowered and target regions of the single stands act as templates which anneal with complementary nucleotide primers. The temperature is raised to an activity temperature where a polymerase enzyme causes a chemical reaction to synthesize new single DNA strands complementary to the single strand DNA templates, which form double helix DNA. The process is repeated until a sufficient number of copies are produced. Fluorescent dyes or fluorophore-containing DNA probes create a detectable signal which intensifies with an increasing number of target DNA fragments. Nucleic acid assays are highly specific and increase in sensitivity when more detectable target DNA fragments are produced. Because of the complex processes for sample preparation, amplification, detection and quantification, nucleic acid assays require highly skilled operators using costly equipment and expensive laboratory facilities. This limits the number of organizations that can conduct nucleic acid assays. Bottlenecks can occur at test labs and cause delays in testing, treatment and remediation. Nucleic acid assays can fail when non-specific DNA products amplify due to contamination or improper sample processing in advance of PCR. Failure can also occur if detectable fluorescent dyes or fluorophores are not adequately delivered along with the replicated target DNA fragments.

Protein assays identify and quantify proteins such as hormones and enzymes, by acting as antigens or antibodies in a chemical reaction. One of the most common protein assays is enzyme-linked immunosorbent assay (ELISA). In a direct ELISA an antigen analyte is adsorbed to a plate and a blocking agent is added to block potential binding sites from non-specific materials. An antibody-enzyme complex is added to bind with the antigen analyte and the plate is washed to remove unbound antibody-enzyme complexes. An appropriate enzyme substrate is added to produce an optical signal proportional to the amount of antigen analyte in the sample. In a Sandwich ELISA, a matched pair of antibodies forms a sandwich structure containing a first outer antibody layer to capture the analyte, an internal layer comprising the antigen analyte and a second outer antibody layer to detect the analyte. The capture antibody is initially bound to the plate and then binds with the antigen analyte contained in a test sample. After washing, a detection antibody-enzyme complex is added to bind with the antigen analyte and the plate is washed to remove unbound capture antibody-enzyme complexes. An appropriate enzyme substrate is added to produce an optical signal proportional to the amount of antigen analyte in the sample. Direct ELISA is faster because only one antibody is being used and fewer steps are required. Sandwich ELISA can have a lower detection limit because each capture antibody can contain several epitopes that can be bound by detection antibodies. Sandwich ELISA can also be made more sensitive using avidin-biotin complexes which have several sites for enzymes to provide multiple enzymes per analyte. This can amplify the detection signal by ten to a few hundred times. In contrast, cell cultures and PCR can produce millions or more copies. Protein assays are relatively easy to use, rapid and low cost. A major disadvantage is the inability to significantly amplify protein signals, making it necessary for the subject or its immune system to produce a detectable level of target protein analytes. This waiting period can delay detection and subsequent treatment by weeks or months. If the protein analytes are assayed using immunoassay before a detectable level is secreted, then a false negative detection outcomes will be produced causing the disease to be undetected. Another problem is the specificity of antibodies and antigens. Many antibodies, and particularly polyclonal antibodies can detect a wide range of species; however these can include non-specific strains that produce false positive detection outcomes. The use of monoclonal antibodies greatly improves specificity.

All of the abovementioned assays suffer from limitations. None of these assays can identify all types of analytes. Unlike cell and nucleic acid assays, protein assays cannot support significant signal amplification which can limit the sensitivity of protein assays. Amplification used in nucleic acid amplification tests and cell cultures adds time, cost and complexity. Cell and protein assays can have insufficient specificity and can benefit from purification steps such as magnetic separation. This adds to the assay cost and complexity. Quantification can be difficult if done manually or expensive if a transduction system is needed to convert optical signals to electrical signals. Nucleic acid amplification assays are sensitive and specific, however the complex processes used for sample preparation, amplification, detection and quantification require highly skilled operators, costly equipment, expensive laboratory facilities, and time-consuming laboratory logistics. This complexity limits the number of organizations that can conduct nucleic acid assays.

Another general type of biological assay is for redox species and works when a redox analyte electrochemically reduces and/or oxidizes at an electrode. A redox analyte is placed in close proximity to a set of electrodes and undergoes electrical stimulation such as applying a potential. This causes the analyte to lose electrons through oxidation or gain electrons through reduction, which can be measured as an electrical signal at the working electrode. The amount of analyte oxidized or reduced and the corresponding electrical signal reflect the quantity of analyte in the sample. Other materials may be also be present such as a mediator to transport redox electrons, and non-specific materials, both of which can cause electrical noise that interferes with the electrical signal from the analyte. When redox analytes are present in high levels, such as approximately $10^{14}$ glucose molecules in blood associated with 1.1 mmol/L, redox signals are relatively high compared with background noise and can be directly measured to provide rapid quantification with acceptable sensitivity and specificity. Since the detection signal is electrical, no expensive transduction system is needed to convert optical signals. This allows glucose meters using redox assays to be performed in rapid, easy to use, low cost instruments.

Other redox analytes can be present in very low levels such as approximately $10^4$ to $10^6$ guanine molecules associated with 5,000 copies/mL of HIV RNA in blood as required for clinical use. Low levels of guanine bases in nucleic acids such as RNA can be oxidized to generate very low electrical current signals while significant background noise currents are produced due to the relatively high potentials required for guanine oxidation. This makes it difficult to distinguish oxidation signals from background noise.

TABLE 2

Examples of Redox Analytes

| Redox Analyte | Sample | Level Required for Clinical Use | Redox Analytes Available for Electrochemical Quantification |
|---|---|---|---|
| Glucose | 1 µL whole blood | 1.1 mmol/L glucose (20 mg/dL) | ~$10^{14}$ glucose molecules |
| HIV | 100 µL whole blood | 5,000 RNA copies/mL | ~$10^4$-$10^6$ guanine molecules |

Various approaches have been employed to quantify nucleic acid analytes using redox assays. Assays that directly detect nucleic acids analytes without amplification (Marks et al) claim to match the sensitivity of ELISA. However these techniques lack any substantial benefit for ELISA users to invest the time and cost to adopt a new technological platform. Other approaches have been employed to quantify nucleic acid analytes using redox assays by improving the signal-to-noise ratio. One approach reduces the active surface area of a biosensor working electrode by replacing a conventional solid working electrode with a nanobiosensor comprising randomly distributed forests of nanoscale structures on the electrode surface (Lieber, et al, Thorpe, et al). Another nanobiosensor approach replaces the randomly distributed forests of nanoscale structures with ordered arrays of nanoscale structures spaced at least 1 µm apart to further reduce the surface area of a working electrode (Gordon, et al). These approaches allowed the guanine signal to be better distinguished from noise over conventional solid working electrodes but not to the degree required for direct measurement of the low level of redox species associated with target bio-analytes such as guanine molecules. Fabrication of nanoscale structures, such as 100 nm diameter carbon nanotubes, provides additional complexity over microscale structures and require specialized production equipment with high cost and limited throughput, poor production yields, and high unit costs for nanobiosensors.

Another approach employs PCR to amplify target DNA before detection by a conventional biosensor (Ozkan, et al). The use of PCR provides added complexity, time and cost which negates the benefits experienced from the glucose redox assay. Another approach employs magnetic separation to purify analytes by removing background interferences before detection by a conventional biosensor. Palesecek et al, and Wang and Kawde capture target sequences using probe DNA immobilized onto magnetic particles. After target hybridization, the particles are magnetically separated from the pool of analytes. The collected DNA is denatured in acidic solutions, and the free guanine and adenine nucleotides are collected and analyzed using anodic stripping voltammetry. Although the noise from other interferents can be reduced, the inherent background signal from water electrolysis always presents. As a result, the guanine oxidation signal is too low for direct measurement in the presence of such large background currents.

Another approach employs magnetic separation to purify analytes and a microparticle bound with signal stranded oligonucleotide tags rich in electroactive guanine to amplify the detection signal (Gordon). The magnetic microparticle and amplification microparticle form a sandwich around the analyte to increase signal-to-noise resolution and at the same time increase the absolute signal based on the length and number of guanine-rich single stranded oligonucleotides placed on the amplification microparticle. The use of two microparticles in the sandwich provides added complexity, time and cost which negates the benefits experienced from the added sensitivity.

There is a need for an assay that can determine the presence and quantity of very low level analytes including multiple analytes and multiple types of analytes in the same sample, provide high sensitivity preferably with signal amplification, provide high specificity preferably with purification, and provide the above in a rapid, easy to use and low cost device, including the capability for point-of-care use.

Another major need is the decision-making process associated with the assay for diagnosing a disease, outbreak and condition. Before an assay is used a decision needs to be make to select the most appropriate assay since a patient, an animal, a biological product or the environment is suspected of having a specific disease, outbreak or condition. An assessment is typically done to order the correct assay that can confirm or rule out if a suspected disease is present. Typically the pre-test assessment can involve a review of a wide range of parameters, symptoms and other information that indicates that one or more specific bioanalytes need to be measured. After an assay is performed the analyte levels are reviewed along with other information to diagnose a disease, outbreak and condition in order to provide appropriate treatments and possible employ other tests if an unexpected outcome is found. While the assay can provide all of the information that is required, in many cases such as early stage detection of infections, cancers and cardiac arrest, low levels of critical biological analytes are difficult to detect. As a result, the evaluation of other pertinent data along with the analytes will improve the accuracy of the biological testing and can also assist in finding the most appropriate treatment. This is particularly needed when regulations and guidelines are incorporated into a tool as expert system rules. As a result, there is a need to provide a tool that can help healthcare professionals, laboratory specialists and others to more rapidly and effectively make decisions to assess the situations, order useful tests, diagnose outcomes and recommend treatments.

SUMMARY OF THE INVENTION

In accordance with a first aspect of the present invention, there is provided a signal amplification sandwich structure for amplifying, detecting and/or quantifying an analyte or multiple different analytes in a fluid sample, wherein said structure comprises (a) a first outer layer comprising a multifunctional particle conjugated with a plurality of a first analyte binding material for binding the analyte, and the multifunctional particle is also conjugated on its outer structure or filled in its inner structure with a plurality of an electrochemically detectable oligonucleotide tag in greater amounts than said analyte in the inner layer; (b) an inner layer comprising said analyte; and (c) a second outer layer comprising a biosensor working electrode, or a sorbent situated near a biosensor working electrode, conjugated with a plurality of a second analyte binding material for binding said analyte that is a matched pair with the first analyte binding material. The electrochemically detectable oligonucleotide tags are for signal amplification, wherein said oligonucleotide tags are single-stranded, duplex or quadruplex, wherein the majority of nucleotides within said oligonucleotide tags are guanine, wherein the number of guanine per electrochemical detectable oligonucleotide tag ranges from 8 to 400, and when a unique electrochemically detectable oligonucleotide tag is used to amplify, detect and/or quantify said analyte or multiple different analytes said oligonucleotide tag is selected from the group consisting of guanine, adenine, thymine, and cytosine.

The multifunctional particles are for delivering said electrochemically detectable oligonucleotide tags to the analyte and for other functions that enhance analyte amplification, detection and/or quantification, wherein the inner structure of said multifunctional particles is selected from the group consisting of structural materials, magnetic materials, optical materials, nuclear materials, radiological materials, quantum materials, biological materials, energetic materials, electrochemical materials, chemical materials, pharmaceutical materials, antibiotic materials, chemotherapy materials, antibodies, and combinations thereof, wherein the number of electrochemically detectable oligonucleotide tags per multifunctional particle ranges from $10^2$ to $10^{13}$, wherein the multifunctional particles are spherical and/or nonspherical, wherein the diameter of spherical multifunctional particles ranges from 0.05 to 400 micrometers, wherein the surface area of nonspherical multifunctional particles has an equivalent surface area of spherical multifunctional particles with ranges from 0.05 to 400 micrometers, and wherein the surface of the multifunctional particles is smooth, rough, porous, or extended with attachments to other particles.

The signal analyte amplification performance of said signal amplification sandwich structure can be tuned to meet the desired limit of detection by adjusting one or more of the following parameters: (a) the number of electrochemically detectable oligonucleotide tags per multifunctional particle; (b) the number of guanines per electrochemically detectable oligonucleotide tag; (c) the size of the multifunctional particle for delivering electrochemically detectable oligonucleotide tags or electrochemical materials; and (d) the surface area of the multifunctional particle for conjugating electrochemically detectable oligonucleotide tags.

The majority of the nucleotides within said quadruplex electrochemically detectable oligonucleotide tags are guanine with at least 4 guanine in a square tetrad structure and an electrochemical detection technique produces 8-oxoguanine signals; wherein the majority of the nucleotides within said quadruplex electrochemically detectable oligonucleotide tags are adenine with at least 4 adenine in a square tetrad structure and an electrochemical detection technique produces 8-oxoadenine signals; wherein the majority of the nucleotides within said quadruplex electrochemically detectable oligonucleotide tags are thymine with at least 4 thymine in a square tetrad structure and an electrochemical detection technique produces 8-oxothymine signals; wherein the majority of the nucleotides within said quadruplex electrochemically detectable oligonucleotide tags are cytosine with at least 4 cytosine in a square tetrad structure and an electrochemical detection technique produces 6-oxocytosine signals; and wherein multiple quadruplexes can form on different segments of the same electrochemically detectable oligonucleotide tag and produce oxo derivative signals from the oxidation of one or more different oxo derivatives.

In accordance with another aspect of the invention, there is also provided a method for amplifying, detecting and/or quantifying one or more analytes in a fluid sample, and diagnosing a disease, outbreak or condition, wherein said method comprises the following steps performed sequentially: (a) providing an artificial intelligence assessment system to recommend actions for assessment of that queries humans, devices, files, records, images, and databases about factors related to diagnosing the disease, outbreak or condition; (b) providing a means for amplifying, detecting and/or quantifying one or more analytes in the fluid sample comprising: i. providing the fluid sample that may contain non-specific materials and an analyte or multiple different analytes; ii. providing one or more sets of multifunctional particle conjugates, wherein each set comprises a plurality of a multifunctional particle conjugated with a plurality of a first analyte binding material and is also conjugated with a plurality of an electrochemically detectable oligonucleotide tag in greater amounts than said analyte to create multifunctional particle-analyte complexes if said analyte or said multiple different analytes are present; iii. providing one or more sets of biosensor working electrodes or one or more sets of sorbents situated near the biosensor working electrodes wherein each biosensor working electrode is associated with said analyte or said group of multiple different analytes that may be present in said sample and wherein each biosensor working electrode or sorbent is conjugated with a plurality of a second analyte binding material that is a matched pair with the first analyte binding material to create signal amplification sandwich structures if said analyte is present; and iv. providing an electrochemical detection technique that produces peak electrochemical signals on each biosensor working electrode in proportion to the quantity of said analyte or said group of multiple different analytes if said analyte or said group of multiple different analytes is present in the fluid sample; (c) providing one or more test results consisting of analyte quantities, and non-bioanalyte and/or bioanalyte levels from other sources that may be associated with the disease, outbreak or condition; (d) providing an artificial intelligence diagnosis system to diagnose and recommend actions for treatment of that interprets said electrochemical signals, non-bioanalyte parameters and/or bioanalyte parameters to diagnosis the disease, outbreak or condition; and (e) providing an artificial intelligence learning system to incorporate improvements, additions and modifications to the artificial intelligence systems and its constituents.

In accordance with another aspect of the invention, there is also provided a device for amplifying, detecting and/or quantifying one or more analytes in a fluid sample and diagnosing a disease, outbreak or condition, wherein said device comprises: (a) device units comprising: i. a sample collection unit configured to collect said fluid sample, ii. a signal amplification tag attachment unit configured to form a first outer layer and inner layer of signal amplification sandwich structures, iii. a signal amplification tag capture unit configured to form a second outer layer of signal amplification sandwich structures, and iv. an electrochemical detection unit with at least one biosensor working electrode configured to measure detection signals from the electrochemically detectable oligonucleotide tags contained on said signal amplification sandwich structures, (b) an artificial intelligence unit comprising: i. an artificial intelligence assessment system configured to collect inputs and recommend actions for assessment using an assessment knowledge base, an assessment inference engine, and computer components, ii. an artificial intelligence diagnosis system configured to collect inputs and recommend actions for diagnosis using a diagnosis knowledge base, a diagnosis inference engine, and computer components, and iii. an artificial intelligence learning system configured to store, process and improve the capabilities of the artificial intelligence assessment system and the artificial intelligence diagnosis system; and (c) one or more units or interfaces that measure non-bioanalyte parameters and bioanalyte parameters.

In the above method and device, the artificial intelligence assessment system and the artificial intelligence diagnosis system each comprise: (1) an input system to obtain answers, medical histories, allergies, predispositions and symptoms from doctors, patients, operators and other people, and to import one or more of images, signals and data from sensors, devices, instruments, actuators, smart phone, computers, databases, records, files, and combinations thereof; (2) a knowledge base comprising one or more of deterministic rules, mathematical models, concentration formulas, image and pattern recognition, Boolean logic, algorithms, standards, changes of parameters over time, rate, temperature, environmental conditions, phases, reactions, events, treatments, remedies, guidelines, regulations, standards, norms, diseases, outbreaks, conditions, other pertinent information and combinations thereof; and (3) an inference engine to interpret inputs, data knowledge base in order to provide recommended actions to complete the assessment and/or diagnosis.

Other features and advantages of the present invention will be better understood upon reading of preferred embodiments thereof with reference to the appended drawings.

BRIEF DESCRIPTION OF THE DRAWINGS

FIG. 11C also contains user markers for pattern recognition of the rash.

DETAILED DESCRIPTION OF THE PREFERRED EMBODIMENTS

Figure 1:
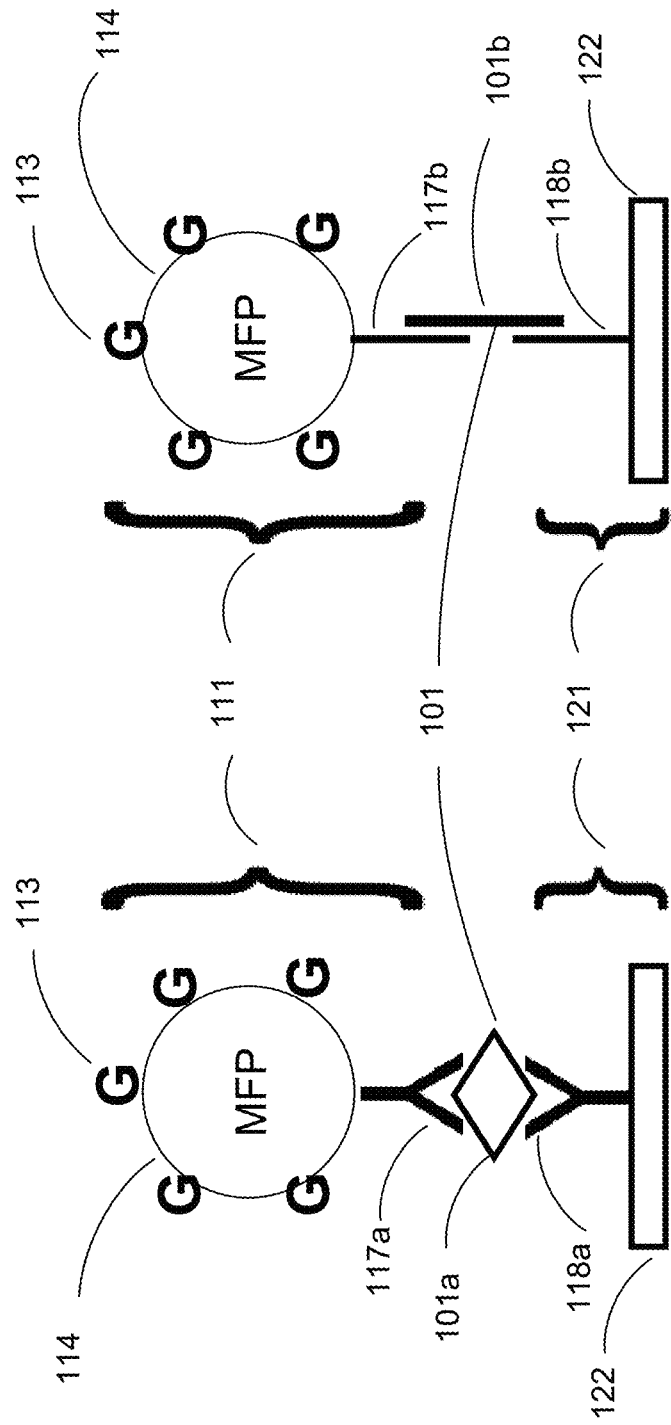
FIG. 1 is a schematic representation of electrochemically detectible oligonucleotide sandwich structures.

In this specification, although the preferred embodiments have been described in detail, it should be understood that various changes, substitutions and alterations may be made without departing from the spirit and scope of the instant invention. Therefore, the specification is to be regarded in an illustrative rather than a restrictive sense. The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

The level, amount, quantity, copies and/or concentration of an analyte can vary greatly in a sample. As would be understood by those skilled in the art, it is much more difficult to identify, detect and quantity low levels of analytes, particularly in the presence of much greater levels of nonspecific materials. The expression "magnetic separation" refers to a process that physically separates analytes from nonspecific materials by binding analytes to magnetically extractable particles. The material used for binding analytes with magnetic particles can include antibodies, monoclonal antibodies, polyclonal antibodies, amino acids, peptides, proteins, haptens, nucleic acids, oligonucleotides, DNA, RNA, aptamers, and combinations thereof.

The expression "electrochemical system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode, and positive control electrode. In the context of the present invention, a single electrochemical system may be used to quantify more than one type of analyte.

The expression "disease, outbreak or condition" is a collective term that refers to the types of diagnoses that can be made from detecting and/or quantifying an analyte or multiple different analytes and/or one or more units or interfaces that measure non-bioanalyte parameters and bioanalyte parameters. These can include but are not limited to infectious diseases, pandemics, cancer, cardiac diseases, neurological diseases, pregnancy, drugs of abuse, drugs, toxins, biomarkers, proteomics, genomics, microbiome, personalized medicine, companion diagnostics, animal health, bioterrorism, food and water safety, biotechnology, pharmaceutical, and forensic applications. It is understood that the above list and subsequent descriptions are given by way of example only, and is in no way limitative to the scope of the present invention.

The present invention generally provides structures, methods and devices for amplifying, detecting and/or quantifying an analyte or multiple different analytes in a fluid sample from a single integrated device. This invention allows ultra-low levels of virtually any biological analyte to be detected and quantified rapidly, simply and inexpensively with an electrochemical biosensor using a novel electrochemical signal amplification technique. Electrochemical detection is among the easiest, most rapid and least costly biodetection technique on the market and is the gold standard for quantifying glucose, metabolites, electrolytes, and blood gases. However, its applications are limited to the subset of analytes that have redox properties and also are present in concentrations that are high enough to be detected by an electrochemical biosensor.

The invention amplifies detection signals from low level analytes using an innovative sandwich structure that replaces optical labels with a massive amount of electrochemically detectable oligonucleotide tags rich in electroactive guanine. The tags bind with analytes to amplify the associated detection signal. An electrochemical technique generates a signal in proportion to the guanine level measured at the working electrode which is also proportional to the analyte level in the sample. Selective binding is achieved with matched pairs of either commercial or custom analyte binding materials such as antibodies or DNA probes.

A starting point for describing this invention is a conventional lateral flow immunoassay. These assays typically bind analytes with conjugates comprising a nanoparticle that may be coated or conjugated with an optical label and an antibody for binding with the analyte to form a nanoparticle-analyte complex. The complex is delivered to a sorbent that is coated or conjugated with a capture antibody for capturing the complex and forming a sandwich structure on the sorbent. The optical labels on the sandwiches are then measured with an optical reader or observed visually to determine if a measurable about of optical labels is formed based on the presence of the associated analytes.

As a comparison, this invention replaces conventional immunoassay conjugates with a novel and non-obvious conjugate. The conjugate's nanoparticle is replaced with a multifunctional structure that can be a microparticle or other shape with a much larger surface area than a nanoparticle. This allows orders of magnitude more detection tags to be conjugated to the particle surface to increase the ability of the assay to detect low levels of analytes. The multifunctional particle can also contain a functional material in its interior such as a magnetic material or antimicrobial agent.

This provides additional functionality for the conjugate to improve the assay performance such as magnetic separation, or provide functionality beyond the assay such as automatically killing infective pathogens in the test sample to reduce the incidence of transmission.

The invention further replaces conventional immunoassay optical label with a novel and non-obvious electrochemical tag. The tag is an electrochemically detectable oligonucleotide rich in electroactive nucleotides such as guanine or nucleotide derivates such as 8-oxoguanine. Not only is the oligonucleotide low cost and commercially available from multiple suppliers, it can be configured for extremely low limits of detection. This is done by increasing the length of the oligonucleotide to contain more electroactive guanine and/or increase the size of the particle to allow more oligonucleotides to be conjugated to the surface. Another advantage is the different forms of the oligonucleotide provide a different signal peak and a greater amplitude at lower levels. For example a single-stranded oligonucleotide consisting of guanine provides a guanine oxidation peak at around 0.9 V, while a quadruplex oligonucleotide consisting of guanine provides an 8-oxoguanine peak at around 0.47 V. The 8-oxoguanine peak is also more distinguishable at lower levels of tags and analyte, allowing quadruplex oligonucleotide tags to provide lower detection limits that single-stranded oligonucleotides.

Another benefit is that because different nucleotides and nucleotide derivatives produce oxidation peaks at different potentials, it is possible to differentiate tags associated with different analytes using the same biosensor working electrode by noticing the potential where the oxidation scan is producing the peak or peaks. This can allow multiplexing at the same electrode. Other examples of how the invention can be used for multiplexing is described below. Another benefit of the oligonucleotide tag over optical labels is that the electrochemical signals are quantitative and are easily measured in a digital format without requiring instruments to transduce the optical signal to electrical. This is seen in electrochemical glucose meters where the electrical signal from the electrochemical reaction is rapidly and easily measured as a quantity that is displayed on a low cost glucose meter and optically communicated though a wireless network to a central database.

However the invention provides a diverse range of benefits expressed as the following combination of capabilities that offer unprecedented industrial useful not unavailable with current detection platforms, including:

Simple, rapid and inexpensive assay
Ultra low limit of detection without PCR or enrichment
Digital, quantitative measurements
Virtually any analyte type, any sample type and multiple platform configurations
Multiplexing including different analyte types from the same sample
Ability to process a large sample (100 mL) to increase the chance of capturing low level analytes in heterogeneous samples
Additional functional for integrated magnetic separation, analyte identification by non-electrochemical means, delivery of payload for treating analytes Not only could this invention allow diseases, cancers and medical conditions to be detected at a much earlier stage when treatment options are less expensive and more successful, it could also enable a new generation of diagnostics that can measure extremely low level analytes using a rapid, simple and inexpensive point-of-care device, similar to a glucose meter, or a point of use device for environmental samples. New applications can include early cancer detection, rapid pathogen detection, microbiome, personalized medicine, and precision medicine. The technology is particularly useful for testing labs, point of care testers and individuals that need low level analytes in samples to be rapidly tested without a laboratory or skilled operators who are typically required for extensive sample preparation and operating sophisticated testing instruments.

As an example of an embodiment of the invention, the device units are configured as a lateral flow test cartridge and an instrument comprising a potentiostat such as an EmStat (DropSens BV, Houten, The Netherlands). A liquid sample that may contain $E.\ coli$ and nonspecific materials is inserted into an inlet of the test cartridge's sample collection unit. The liquid sample flows laterally to the signal amplification tag attachment unit which contains a set of multifunctional particle conjugates for amplifying the signal. Each conjugate comprises a multifunctional particle conjugated with a plurality of a polyclonal antibody for binding $E.\ coli$ and a plurality of an electrochemically detectable oligonucleotide tag in much greater amounts than the $E.\ coli$ being bound to the conjugate. $E.\ coli$ in the sample bind with the conjugates and multifunctional particle-$E.\ coli$ complexes. The complexes flow laterally to the signal amplification capture unit which contains biosensor working electrodes with monoclonal antibodies conjugated on or near the working electrode surfaces for capturing the multifunctional particle-$E.\ coli$ complexes. $E.\ coli$ in the complexes bind with capture unit's monoclonal antibodies to form signal amplification sandwich structures. The test cartridge is inserted into the analyzer which applies a square wave voltammetry scan and produces an electrical current signal proportional to the electrochemically detectable tags bound in signal amplification sandwich structures at the biosensor working electrode. The signal is also proportional to the concentration of $E.\ coli$ in the sample. The $E.\ coli$ concentration is determined from a preprogrammed mathematical formula that converts the peak electrical current form the scan to a concentration based on peak electrical currents of known samples. A second working electrode is used as a negative control to verify that the test is valid.

A benefit of this invention is that the method for measuring analytes uses as few as 3 steps which are very simple and can be automated. This allows the method to be portable and used in diverse platforms including lateral flow devices, 96-well microtiters, high throughput systems, inline systems, and other common assay platforms. Another benefit is that the method is rapid as each step can be conducted in minutes. Another benefit is that the method employs a small number of low cost reagents and off the shelf instrument components, making the cost per test very low. Similar benefits are also provided with lateral flow devices using conventional optical tags.

Ultra-Low Limit of Detection

However an unprecedented aspect of this invention is the use of a novel signal amplification sandwich structure that allows extremely low levels of analytes to be measured using the simple, rapid and inexpensive method. The signal amplification sandwich structure binds millions of electrochemically detectable oligonucleotide tags to an analyte instead of a single optical label used in conventional lateral flow assays such as a pregnancy test. An innovative aspect of this invention is that the signal analyte amplification performance of said signal amplification sandwich structure can be tuned to meet the desired limit of detection by adjusting one or more of the following parameters: (a) the number of electrochemically detectable oligonucleotide tags per multifunctional particle; (b) the number of guanines per electrochemically detectable oligonucleotide tag; (c) the size of the multifunctional particle for delivering electrochemically detectable oligonucleotide tags or electrochemical materials; and (d) the surface area of the multifunctional particle for conjugating electrochemically detectable oligonucleotide tags.

As an example of an embodiment of the invention, the amplification performance was set at ~$10^6$ guanine nucleotides per analyte by binding ~$5 \times 10^5$ oligonucleotide tags per multifunctional particle, with each oligonucleotide tag containing 20 guanine. It is necessary to ensure that the multifunctional particle used for the assay has sufficient surface area to fit the required number of oligonucleotide tags. In this example, ~$5 \times 10^5$ oligonucleotides can fit on a 1 micron spherical particle based the maximum packing density of oligonucleotides per surface area being ~$10^{12}/cm^2$. If additional amplification is required to attain a lower limit of detection, then adjustments can be made for using longer oligonucleotides that increase the number of guanine from 8 to up to 400. In the above example, the amplification performance would increase to set at ~$2 \times 10^7$. In another embodiment, the spherical particle can increase in size from 1 micron to 15 microns, providing ~56 times more surface area along with ~56 times more electrochemically detectable oligonucleotide tags.

The truly innovative aspect of the invention is allowing ultra-low levels of virtually any biological analyte to be detected and quantified rapidly, simply and inexpensively with an electrochemical biosensor. A comparison of the measurement capabilities of the invention with other biodetection platforms is provided in the following table. The values and estimates are sourced from references that describe detection limits for a wide range of similar groups of technologies and platforms. Specific technologies can have values that deviate from the values being reported. The term measurement capability is used as a general term to correlate comparative values reported for sensitivity, limit of detection and limit of quantification.

margin. Kozar indicates a measurement capability of 0.033 mmol/L for Accu-Chek Compact Plus® portable instrument (Roche Diagnostics GmbH, Mannheim, Germany). This converts to about $6.0 \times 10^{12}$ molecules which is approximately 33 times lower than the lower range of glucose levels.

Table 4 also provides the relative measurement capabilities of representative direct ELISA and sandwich ELISA platforms used for the detection of proteins. The values and estimates are provided from ELISA technical documents published by KPL (Gaithersburg, Md.) and Thermo Scientific (Rockford, Ill.). Sandwich ELISAs using horseradish peroxidase (HRP) enzymes and colorimetric detection are the most common immunoassays. ELISA measurement capabilities are typically expressed in pg/mL. For a typical protein such as Interleukin 2 (IL-2), the relative detection limits are approximately 2,125 pg/mL for direct ELISA and 1.4 pg/mL for sandwich ELISA. ELISA applications requiring sensitivities below 1 pg/mL can be obtained using chemiluminescent or chemifluorescent substrates which are much more expensive and more difficult to use. Because the molecule weights of proteins vary, a better unit to compare detection platforms is pmols. For example, in the case of Interleukin 2 (IL-2) protein with a molecular weight of 17,000 g/mol, 2125 pg/mL can be converted to pM by dividing the concentration of 2125 pg/mL by the molecular weight of 17,000 g/mol and multiplying by 1000 mL/L. This provides detection capabilities of approximately 125 pmols for direct ELISA and 0.08 mmols for sandwich ELISA. The sensitivity for sandwich ELISA is higher because of signal amplification. Each primary antibody contains several epitopes that can be bound by the labeled secondary antibody. Sandwich ELISA can also be made more sensitive using avidin-biotin complexes which have multiple sites for enzymes. This allows up to about 200 enzymes per analyte. In comparison, this invention provides many orders of magnitude greater amplification by binding up to $10^{15}$ electrochemically detectable tags per analyte. Using data from the *E. coli* O157:H7 example described earlier, the

TABLE 3

Relative Measurement Capabilities of Representative Redox Biosensors and the Invention

| Measurement Capabilities | Blood Glucose Lower Limit | Direct ELISA | Sandwich ELISA | Invention's Amplification & Nanobiosensor |
|---|---|---|---|---|
| Detection limit (M) | $1.1 \times 10^{-3}$ | $1.3 \times 10^{-10}$ | $8.3 \times 10^{-14}$ | $5.0 \times 10^{-21}$ |
| Sample volume (μL) | 3 | 100 | 100 | 1000 |
| Analytes in sample | $2.0 \times 10^{14}$ | $7.5 \times 10^9$ | $5.0 \times 10^6$ | 3 |
| Tags per analyte | 1 | 1 | 200 | $1.5 \times 10^8$ |
| Recovery by antibodies | 100% | 80% | 60% | 60% |
| Detectable tags | $2.0 \times 10^{14}$ | $6.0 \times 10^9$ | $6.0 \times 10^8$ | $2.6 \times 10^8$ |

Table 3 show the lower concentration requirement for measuring glucose in whole blood as 1.1 mmol/L (or 20 mg/dL). Some commercial glucose meters such as Abbott FreeStyle® (Abbott Diagnostics Care, Alameda, Calif.) detect glucose from a 0.3 μL sample. This corresponds to $3.3 \times 10^{-10}$ moles of glucose by multiplying 1.1 mmol/L concentration by 0.3 μL sample volume. The level can also be expressed as $2 \times 10^{14}$ glucose molecules by multiplying $3.3 \times 10^{-10}$ mols by Avogadro constant $6.02 \times 10^{23}$/mol. Since commercial glucose meters need to measure the lowest required glucose levels, they typically have the additional capability to measure significantly lower levels as a safety invention was able to detect 7 orders of magnitude lower levels than sandwich ELISA as illustrated in Table 4.

In contrast, this invention has attained $5.0 \times 10^{-18}$ mmol/L levels, which was a 13 order of magnitude improvement over the measurement capabilities of glucose nanobiosensors, by using a unique combination of detection technologies. The invention's amplification beads converted 3 analyte molecules into $2.6 \times 10^8$ detectable guanine redox molecules. A greater amplification ratio of up to $10^{15}$ electrochemically detectable targets per analyte could have been used to generate a bigger signal. Non-specific materials were removed from analytes using magnetic separation to reduce noise during detection. The guanine molecules were bound near the working electrode surface when hybridized with cytosine probes to generate a higher signal than if the redox materials were disbursed throughout the solution. A graphene oxide nanobiosensor was used which is low cost, easy to fabricate and generated easy-to-measure signals in the 30-100 nA range. As well, a normalization process was able to correct measurement inconsistencies from sensor to sensor.

As an example of a preferred embodiment is the detection and diagnosis of Lyme disease. In little more than 30 years Lyme disease has risen from relative obscurity to become a global public health problem with over 300,000 new cases per year just in the US. Most Lyme disease patients are successfully treated with antimicrobials if diagnosed at an early stage. Even if appropriately treated 10% to 20% of Lyme disease patients will remain symptomatic due to misdiagnosis. Lyme disease diagnosis is complex and lengthy. It consists of assessing Lyme disease symptoms, determining the presence of the Erythema migrans (EM) bullseye rash, and detecting Lyme disease antigen/antibody biomarkers. The EM bullseye rash is caused by a tick biting a patient and subsequently injecting between 200-500,000 Borrelia bacteria. Diagnosis of the EM can be difficult, since the rash has 3 distinct morphologies and is often confused with nummular eczema, granuloma annulare, an insect bite, ringworm, or cellulitis. 63% of EM bulleye rashes are misdiagnosed by General Practitioners. Another 20% of Lyme disease patients do not have an EM bulleye rash and risk being misdiagnosed because of the poor specificity of other symptoms such as fever and joint pain.

There are many diagnostic tests for Lyme disease. A systematic review from 48 studies on the accuracy of LD diagnostic tests at various stages of Lyme disease showed test sensitivity (i.e. true positive rate) of only 46% in stage 1 acute LD testing with the 2 tier serological testing and an astounding 54% of LD patients not detected in stage 1 (Waddell) There is a dramatic increase in test sensitivity and true positives with progression of B. Burgdorferi infection from early to late stage Lyme disease. Direct detection methods, culture and PCR of tissue or blood samples were not as sensitive or timely compared to serological testing.

TABLE 4

Lyme Disease Test Outcomes (Waddell)

| | True Positive Rate (Detected Lyme disease) | False Negative Rate (Undetected Lyme disease) |
|---|---|---|
| Stage 1 Acute LD | | |
| ELISA/Western Blot (blood) | 46% | 54% |
| Culture (biopsy/blood) | 27%-94% | 6%-73% |
| PCR (biopsy/blood) | 34%-62% | 38%-56% |
| Stage 2 Neurological/Cardiac LD | | |
| ELISA/Western Blot (blood) | 90% | 10% |
| Stage 3 Neurological/Arthritis LD | | |
| ELISA/Western Blot (blood) | 99.4% | 0.6% |

Technical Feature 1—Lower Detection Limit

The present invention provides a novel and non-obvious signal amplification sandwich structure, method and device for greatly reducing the detection limit compared with conventional assays. This is particularly important for detecting early stages of diseases, pathogens and conditions when treatment is more effective and less costly. Some of the key features include the following.

A novel and non-obvious detection label: The present invention discloses a detection label comprising a multifunctional particle conjugated with a plurality of a first analyte binding material for binding the analyte, and a plurality of an electrochemically detectable oligonucleotide tag in greater amounts than the analyte. The generated detection signal from the plurality of electrochemically detectable oligonucleotide tags is much greater than the optical signal from an optical label used in conventional assays. This tag allows the present invention to detect bound analytes at low levels than conventional analytes such as ELISA and Western Blot.

In a preferred embodiment, the oligonucleotide tags are guanine-quadruplexes which generate 8-oxoguanine electrochemical signals at 2-3 logs lower levels than guanine oxidation signals. The signals are quantitative and are proportional to the concentration of analytes bound in sandwiches. The analytes can be measured with a conventional electrochemical biosensor and potentiostat, similar to a glucose meter for pathogens. The millions of guanine-quadruplex oligonucleotides tags are bound to a streptavidin coated particle that are also conjugated with antibodies for immuno analytes or DNA probes for nucleic acid analytes. Lower LOD is achieved with bigger beads and more guanine per oligonucleotide for quadruplexes. In a preferred embodiment the particle is a magnetic particle. This allows non-specific materials in the sample to be magnetically separated from the analytes bound to the particles to reduce the impact of noise that could interfere with the detection signal.

A novel and non-obvious method and device for amplification, detection and/or quantification: The present invention also discloses a method and a device for amplification, detection and/or quantification by i) providing the fluid sample that may contain non-specific materials and an analyte or multiple different analytes; ii. providing one or more sets of multifunctional particle conjugates comprises a plurality of a multifunctional particle conjugated with a plurality of a first analyte binding material and is also conjugated with a plurality of an electrochemically detectable oligonucleotide tag in greater amounts than said analyte to create multifunctional particle-analyte complexes if said analyte or said multiple different analytes are present; iii. providing one or more sets of biosensor working electrodes or one or more sets of sorbents situated near the biosensor working electrodes wherein each biosensor working electrode is associated with said analyte or said group of multiple different analytes that may be present in said sample and wherein each biosensor working electrode or sorbent is conjugated with a plurality of a second analyte binding material that is a matched pair with the first analyte binding material to create signal amplification sandwich structures if said analyte is present; and iv. providing an electrochemical detection technique that produces electrochemical signals on each biosensor working electrode in proportion to the quantity of said analyte or said group of multiple different analytes if said analyte or said group of multiple different analytes is present in the fluid sample.

Figure 11C:
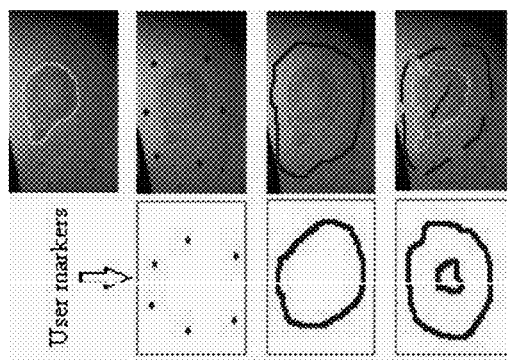
FIGS. 11B, 11C, and 11D are images of rashes associated with Lyme disease.
Figure 11B:
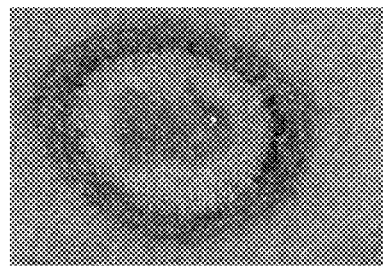
Figure 11D:
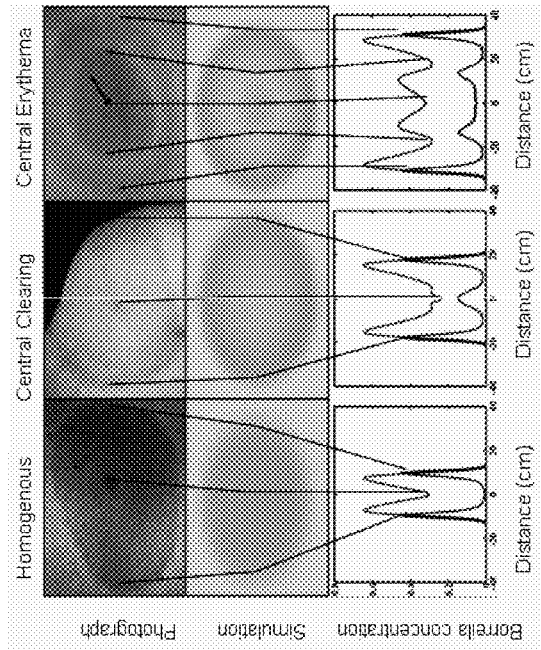
Figure 11A:
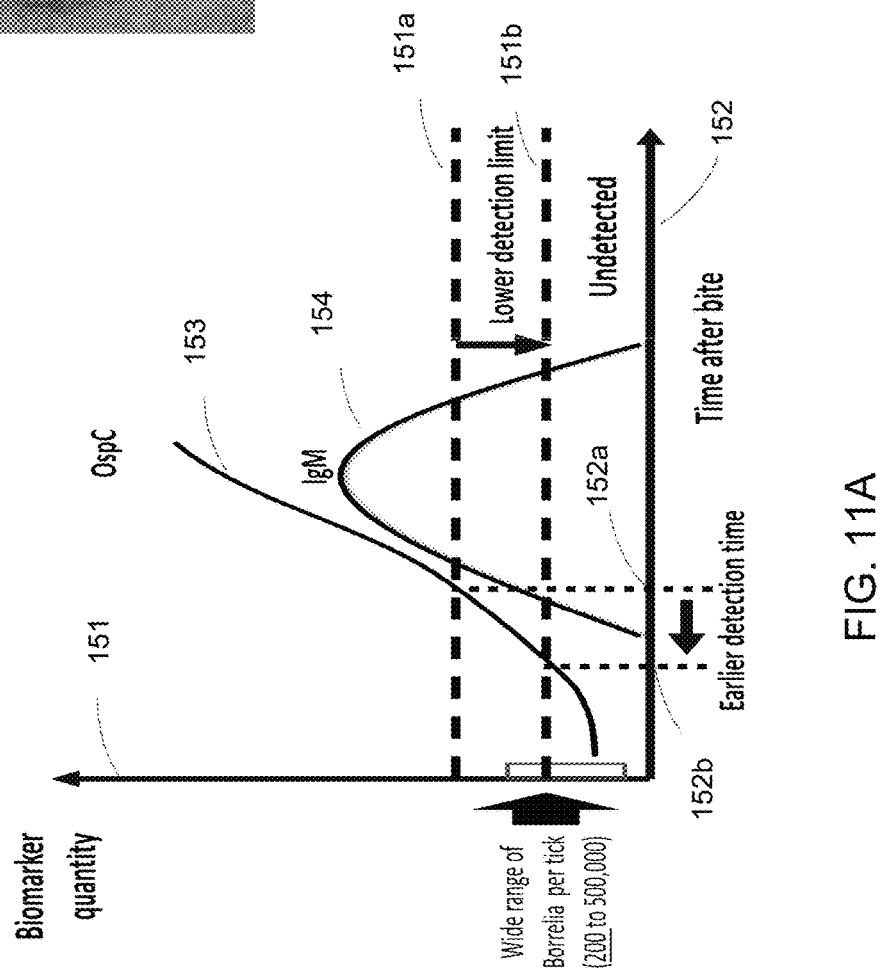
FIG. 11A is a graph of analyte concentration versus time for Lyme disease illustrating one embodiment of the present invention.

Referring to FIG. 11A, there is a graph that plots analyte concentration 151 versus time after incurring a tick bite 152. Separate lines show the concentrations over time of a Lyme disease antigen OspC 153 and a Lyme disease antibody IgM 154. The detection limit of an ELISA test is shown as the dotted line 151a which can be detected at the corresponding time post-tick bite of 152a. The lower detection limit from the present invention is shown as the dotted line 151b. The lower detection limit can be detected at the corresponding time post tick bite of 151*a*, which can be several days or weeks earlier than the ELISA test.

Other advantages of the present invention's method and device include: a) multiplexing to detect multiple *Borrelia* antigens and antibodies in the same test, b) quantitative results since the tags generated a digital electrochemical signal that can be calibrated with a concentration curve similar to a glucose meter, c) the simplicity of the signal amplification method which avoids the need for replicating techniques that require time, specialized resources and a laboratory, and d) the use of an off-the-shelf Bluetooth-enable potentiostat which allows testing at the point-of-care.
Technical Feature 2—Higher Sensitivity and Specificity at Early Stage Detection The present invention also provides a novel and non-obvious artificial intelligence system for greatly improving the invention's clinical sensitivity (i.e. True Positive Rate) and test specificity (i.e. True Negative Rate) compared with bioanalyte testing alone. Sensitivity and specificity are particularly important at the early stage of diseases, pathogens and conditions when a correct diagnosis can make the difference between life and death for certain cancers, virulent infections, outbreaks in food and water, defense against bioterrorists, deadly epidemics, and cardiac arrest, as well as prolong the quality of life for neurological diseases, cancers and other life-threatening medical and environmental conditions.

A novel and non-obvious artificial intelligence system: The present invention discloses an artificial intelligence system comprising an artificial intelligence assessment system that queries humans, devices, files, records, images, and databases about factors related to diagnosing the disease, outbreak or condition. This is used to determine if an analyte needs to be tested and if so, to ensure that the correct analytes and sample types will be tested according to symptoms, current outbreaks, and other parameters that may be pertinent to a correct diagnosis. The assessment can involve inputting parameters from questioning a patient and/or professional, accessing related tests and databases, and subsequently suggesting other tests that would be needed according to the latest regulations and guidelines entered into a knowledge base. An inference engine can also assess one or more test results consisting of non-bioanalyte and/or bioanalyte levels from other sources that may be associated with the disease, outbreak or condition.

An artificial intelligence diagnosis system is used to interpret the electrochemical signals from the analyte tests along with non-bioanalyte parameters and/or bioanalyte parameters to diagnosis the disease, outbreak or condition. The diagnosis is based on deterministic rules, mathematical models, image and pattern recognition, Boolean logic, algorithms, standards, changes of parameters over time, rate, temperature, environmental conditions, phases, reactions, and events according to the latest regulations and guidelines for diagnosing specific diseases, pathogens and conditions using a second knowledge base and inference engine. This provides a tool for assisting professionals to make comprehensive and compliant diagnostic decisions particularly if a second opinion is desired or if the guidelines are not readily available.

An artificial intelligence learning system allows updates to the guidelines to be entered manually or automatically along with new rules that come from independent sources along with new treatments, new drugs, new technologies, new pathogen strains, new resistance to antimicrobials and new discoveries. The artificial intelligence system is also linked with the present invention's method and device for amplification, detection and/or quantification to make real-time diagnosis that includes actual bio-analyte levels. This offers a more precise set of diagnosis that is not available with static guidelines.

A novel and non-obvious method and device for diagnosing diseases, pathogens and conditions: The present invention also discloses a novel and non-obvious method and device for diagnosing diseases, pathogens and conditions by: (a) providing an artificial intelligence assessment system to recommend actions for assessment of the disease, outbreak or condition; (b) providing a means for amplifying, detecting and/or quantifying one or more analytes in the fluid sample as described above, (c) providing one or more test results consisting of non-bioanalyte and/or bioanalyte levels from other sources that may be associated with the disease, outbreak or condition, (d) providing an artificial intelligence diagnosis system to recommend actions for treatment of the disease, outbreak or condition; and (e) providing an artificial intelligence learning system to incorporate improvements, additions and modifications to the artificial intelligence systems and its constituents.

For Lyme disease the present application converts the 2006 Infectious Disease Society of America expert panel guidelines for Lyme Disease Diagnosis into a series of rules. However as of the filing date of present application, the latest Lyme disease guidelines is 12 years old. In the Lyme disease example, the assessment system queries the patient, the doctor and other sources about symptoms, whether the patient has been bitten by an insect, the likely geographic location where the insect bite may have occurred, the incidence of Lyme disease and related ticks in the geographic location, and other related information pertaining to Lyme disease and other diseases that may present like Lyme disease. Relevant information is summarized on Table 5.

TABLE 5

Artificial Intelligence Assessment System Inputs

| | Symptoms | Status |
|---|---|---|
| A1 | Fever | Yes |
| A2 | Joint pain | yes |
| A3 | Rash | Yes |
| A4 | Insect bite | Yes |
| A5 | Days since bite | 7 days |
| A6 | Insect bite location (Zip code) | 12144 |
| A7 | Insect available | Yes |
| A8 | Previously had Lyme disease | No |

The assessment system would then make a preliminary assessment of whether Lyme disease can be ruled out, or whether further testing is recommended. In the latter case, the assessment system would recommend the specific test cartridge(s) that should be used by the present invention. For example, if the patient was bitten in the Northeast US then the cartridge would measure antigens and antibodies associated with *Borrelia Burgdorferi sensu lato*. If the patient presents with neurologic manifestations then the assessment system would also recommend a test cartridge to measure antigens and antibodies associated with *Borrelia garinii*. While all antibody tests require blood samples, in some cases a skin biopsy could be recommended to detect *Borrelia* antigens. The assessment system could also recommend that a photo of the EM bullseye rash be taken at one or more times to determine by image recognition if the EM matches the pattern from one or more EM morphologies in the Artificial Intelligence diagnosis database. The image recognition could also be used to rule out the EM if the photo image positively matches the image of ringworm or other non-Lyme disease rash.

TABLE 6

Artificial Intelligence Assessment System Inputs

Assessment Actions

| | |
|---|---|
| B1 | Guanine Blood test for *B. Burgdorferi* Antigens/Antibodies |
| B2 | Upload photo of rash |
| B3 | Upload photo of insect |

The artificial intelligence diagnosis system contains an image recognition algorithm to positively identify EM or rule out EM to ensure timely and targeted medical treatment for Stage 1 Lyme disease independent of the bioanalyte test. Erythema migrans typically develop 7-14 days post-tick-bite and gradually expands, and in some patients antigens and antibodies may be too low to be measured in blood at the time of the EM scan. The classic appearance of the bulls-eye rash consists of a circular red center surrounded by a region of central clearing and one or more red outer rings. However, at varying points during infection Erythema migrans may also appear as an amorphous flat rash with no central clearing (homogenous Erythema), or a rash with no central redness (central clearing rash). Previous attempts to develop a pattern recognition algorithm for EM relied on the shape properties and attribute calculation of a single EM photo with outline markers (Cuk) as shown in FIG. 11C. Static photos can be enhanced for improved predictive ability by taking multiple photos of the rash that evolve over time as the three Erythema migrans rash morphologies can be mathematically modeled in simulations (Vig) and therefore patterns have been used for better recognizing the EM shapes in FIG. 11D. Furthermore rules can be used to further differentiate EM from non Lyme disease images such as ringworm in FIG. 11B by size, shape, color, growth and include distinguishing characteristics by patient demographic, geographic region, other symptoms and related co-infections. The algorithm identifies patient images from three Erythema migrans rash morphologies that are a) true positive, b) true negative or c) indeterminate with a probability factor and key criteria. The end of the diagnosis provides a list of results and recommended actions as illustrated in Tables 7 and 8.

TABLE 7

Artificial Intelligence Diagnosis Results

| | Parameter | Parameter Value | Finding |
|---|---|---|---|
| C1a | *B. Burgdorferi* OspC | Positive | Lyme disease Positive |
| C1b | *B. Burgdorferi* VlsE | Positive | Lyme disease Positive |
| C1c | *B. Burgdorferi* IgM | Positive | Lyme disease Positive |
| C1d | *B. Burgdorferi* IgG | Positive | Lyme disease Positive |
| C2 | EM Rash | EM Morphology 3 | Lyme disease Positive |
| C3 | Insect | *Ixodes angustus* | Lyme disease Positive |

TABLE 8

Artificial Intelligence Diagnosis Recommendations

| | Parameter | Value |
|---|---|---|
| D1 | Treat with Doxycycline | 100 mg, twice per day orally, 14 days |

Other Unique Capabilities

The invention also comprises many other unique capabilities. The starting sample may be embodied by any fluid which may contain an analyte, such as blood or other bodily fluids, liquefied solids or tissues, naturally produced or processed food products, water or other liquids, or liquefied materials from air or gases. Examples include but are not limited to peripheral blood, plasma, serum, urine, saliva, nasal swab, tissue biopsy, surgical specimen, amniocentesis sample, autopsy material, body fluid, stool, surface, container, water, liquefied air particles, gases, food, food extracts, beverages, agricultural and aquacultural products, pets and animals used for food or medical research, and other materials coming from human subjects, veterinary subjects, animals, rodents, lizards, fish, birds, insects, plants, and biological structures. Original samples may be taken from any source. A sample may also be a liquid derived from the original sample by removing or adding components.

The analyte may be any biological material of interest which one may wish to identify, detect or quantify. Examples of analytes include cells, bacteria, protozoa, fungi, virus particles, proteins, peptides, enzymes, hormones, haptens, cancer markers, nucleic acids, genes, oligonucleotides, DNA, RNA, small molecules, drugs, pesticides, organic chemicals, industrial chemicals and compounds. Analytes can be species-specific, strain-specific, genotype-specific, or cluster-specific. The use of the term "target" can be applied to indicate one of more specific analytes that one wishes to identify, detect or quantify.

The analyte binding materials can be antibodies, monoclonal antibodies, polyclonal antibodies, amino acids, peptides, proteins, haptens, nucleic acids, oligonucleotides, DNA, RNA, aptamers, and combinations thereof. As known by one skilled in the art, sandwich ELISAs typically require two different binding materials referred to as matched pairs and in the case of an antigen analyte, each of the binding materials will be antibodies that react with a different epitope of the antigen. Furthermore monoclonal antibodies are specific for a single epitope and can be obtained in very pure form to be reactive with different epitopes. By using different antibodies on the magnetic bead and non-magnetic bead, the sandwich structure will increase the specificity of the assay, since few potentially cross reacting molecules will share two epitopes.

In addition to biological analytes, the fluid sample may contain other nonspecific materials such as non-target biological materials and non-biological materials. These nonspecific materials are not the object of the determination being performed. Some of these nonspecific materials can interfere with or aggregate with analytes to prevent the detection of analytes, causing undesirable false negative detection outcomes. Some of these non-specific materials including nonspecific species of the analytes can be falsely detected in the absence of the analytes, causing false positive detection outcomes. As well the total sum of nonspecific materials can outnumber the sum of analytes in a sample by several orders of magnitude to create substantial noise that prevents the detection signal generated from the analytes to be distinguished from said noise, causing undesirable false negative or inconclusive detection outcomes.

The multifunctional particles are for delivering said electrochemically detectable oligonucleotide tags to the analyte and for other functions that enhance analyte amplification, detection and/or quantification, wherein the inner structure of said multifunctional particles is selected from the group consisting of structural materials, magnetic materials, optical materials, nuclear materials, radiological materials, quantum materials, biological materials, energetic materials, electrochemical materials, chemical materials, pharmaceutical materials, antibiotic materials, chemotherapy materials, and combinations thereof. The structural materials can include styrene, polystyrene, porous polystyrene, polymer, agarose, dextran, glass, ceramic, composite material and combinations.

Signal Amplification Sandwich Structure

With reference to FIG. 1, an illustration is shown of a signal amplification sandwich structure 122 for amplifying the electrochemical detection signal from one or more analytes in a fluid sample. The signal amplification sandwich structure binds each analyte with millions of electrochemically detectable oligonucleotide tags rich in electroactive guanine. This makes it possible to detect very low analyte concentrations, and potentially even single analytes or single molecules. As it is faster, easier, and less costly to attach millions of electrochemically detectable oligonucleotide tags to analyte rather than to replicate millions of analyte copies using PCR or cultures, the signal amplification sandwich structures can allow extremely low levels of analytes to be detected at a fraction of the time and cost of amplification techniques that require time-intensive, and resource-intensive processes.

The signal amplification sandwich structure first comprises an outer layer 111 referred to as a multifunctional particle conjugate comprising a multifunctional particle 114 conjugated with a plurality of an analyte binding material 117a and is also conjugated with a plurality of electrochemically detectable oligonucleotide tags 113 in greater amounts than the associated bound analyte. The signal amplification sandwich structure next comprises an inner layer comprising analyte 101. The signal amplification sandwich structure further provides an outer layer 121 comprising a biosensor working electrode 122 with a plurality of an analyte binding material 118a conjugated on or near the biosensor working electrode surface.

Figure 2B:
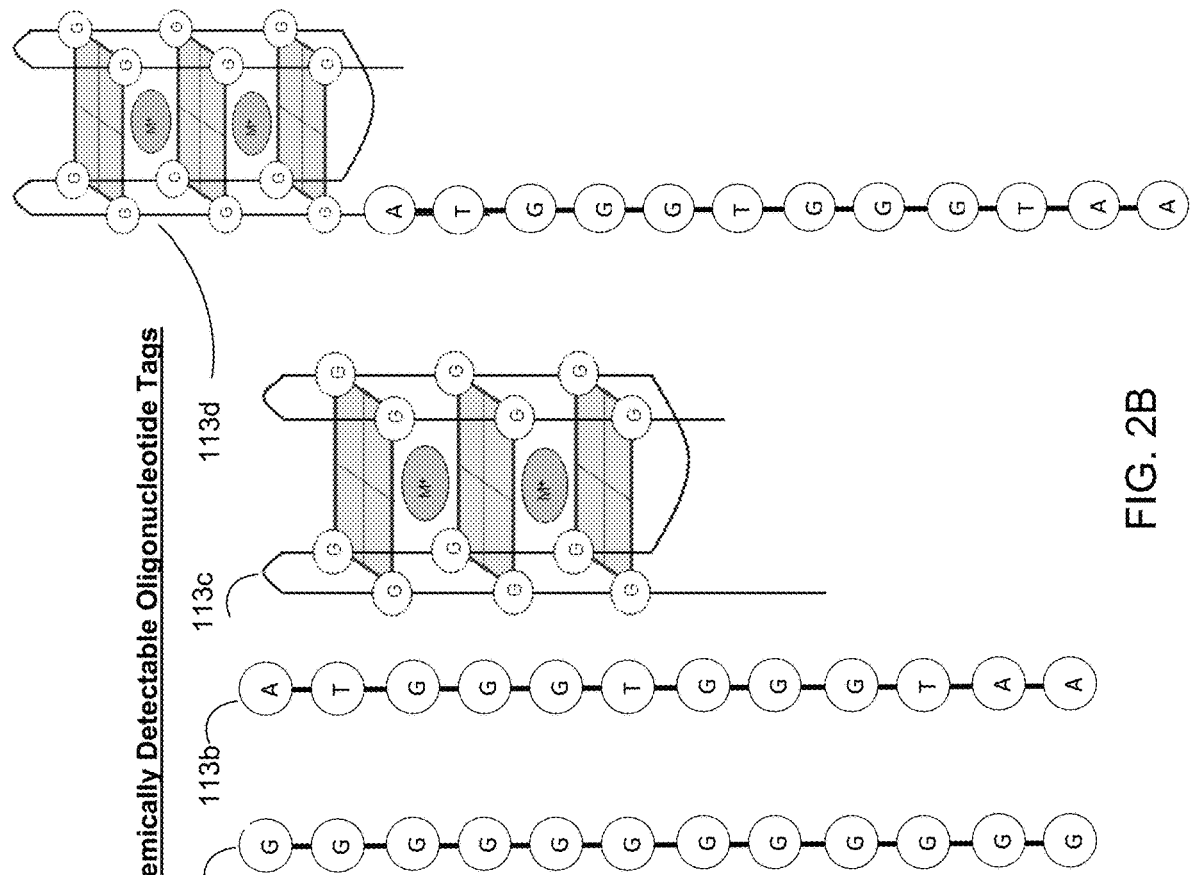
FIG. 2B is a schematic representation of electrochemically detectable oligonucleotide tags.
Figure 2A:
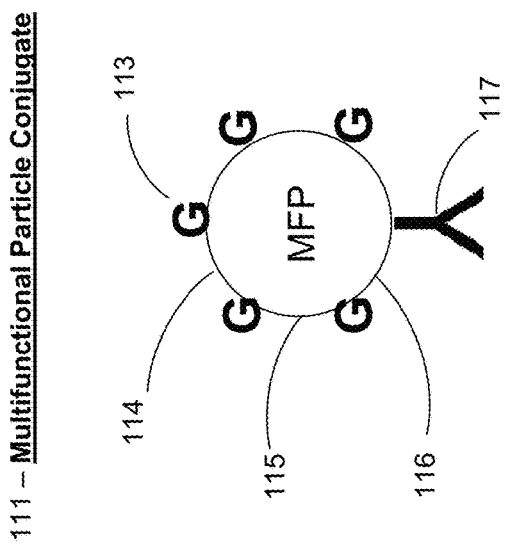
FIG. 2A is a schematic representation of a multifunctional particle conjugate.

With reference to FIGS. 1 and 2A an illustration is shown of the signal amplification sandwich structure outer layer 111 which is also referred to as a multifunctional particle conjugate. The outer layer first provides a substrate, such as a particle 114. The shape of the substrate may be a sphere, a rod, a plate, a disk, a dendrimer, or other shape having an outer structure surface 115 which can be used to bind with a plurality of the analyte binding material 117, and also bind with a plurality of an electrochemically detectable oligonucleotide tag 113. The term particle is being used to describe the substrate but the description can be used for all other substrate shapes.

In some embodiments the outer surface 115 of the particle is smooth. In some embodiments the particle's outer surface is rough or porous in order to increase the surface area for binding a greater number of electrochemically detectable oligonucleotide tags and analyte binding materials. In some embodiments, the particle's outer surface material is agarose, silica, polymer, glass, composite or other material which has suitable chemical processes for attaching analyte binding materials and electrochemically detectable tags.

Referring to FIG. 2A, the electrochemically detectable oligonucleotide tags 113 are used for signal amplification. Another innovative aspect of the signal amplification detection structure is that the electrochemically detectable oligonucleotide tags can have one or more forms, such as but not limited to single stranded oligonucleotides, duplex oligonucleotides, quadruplex oligonucleotides, combinations of oligonucleotides with other biological, natural or synthetic constituents, and combinations thereof. With reference to FIG. 2B, in one embodiment the electrochemically detectable oligonucleotide tags are single stranded oligonucleotides comprising only guanine nucleotides 113a (SEQ ID NO. 1). In another embodiment the electrochemically detectable oligonucleotide tags are single stranded oligonucleotides wherein the majority of nucleotides within said oligonucleotide tags are guanine 113b (SEQ ID NO. 2), wherein said nucleotides within said oligonucleotide tags are selected from the group consisting of guanine, adenine, thymine, and cytosine, and wherein the combination of said nucleotides produces a unique oligonucleotide tag that is used to amplify, detect and/or quantify said analyte or multiple different analytes. In another embodiment, the electrochemically detectable oligonucleotide tags are quadruplexes 113c (SEQ ID NO. 3), wherein the majority of the nucleotides within said electrochemically detectable oligonucleotide tags are guanine with at least 4 guanines in a consecutive sequence, wherein sets of 4 guanine comprise square planar tetrad structures bound by eight Hoogsteen hydrogen bonds, wherein two or more square planar tetrad structures are stacked on top of each other and stabilized by pi-pi hydrophobic interactions, and wherein between each square planar tetrad structure in the stack has a monovalent cation which is coordinated to the lone pairs of electrons of O6 in each guanine, wherein the quadruplex electrochemically detectable oligonucleotides are exposed, adsorbed or hybridized to a biosensor working electrode surface wherein a redox detection technique oxidizes said tag and produces 8-oxoguanine signals.

In another embodiment, the electrochemically detectable oligonucleotide tags are quadruplexes, wherein the majority of the nucleotides within said electrochemically detectable oligonucleotide tags are primarily adenine and produces 8-oxoadenine signals, are primarily thymine and produces 8-oxothymine signals, are primarily cytosine and produces 6-oxocytosine signals, or are combinations thereof.

In another embodiment, the electrochemically detectable oligonucleotide tag 113 and the analyte binding material 117 are fabricated on the same oligonucleotide 113d (SEQ ID NO. 4). As an example, the oligonucleotide can have biotin at the 5' end, followed by a small linker such as TTA commonly found in naturally occurring guanine quadruplex telomeres, followed by the polyguanine sequence, then a linker such as TTA TTT TTC, then the analyte binding material: 5' Biotin—TTA GG GGG GGG GGG GGG GGG GGG TTA TTT TTC CAT TAT TAG GTC AGC CAT TGT TGC TTG CCA TGC GAC TCC CGC CTT TTT T (SEQ ID NO. 5).

In one embodiment the analyte binding material is a DNA probe that binds with a nucleic acid analyte such as RNA. In another embodiment the analyte binding material is an aptamer that binds with a protein analyte such as a protein.

The signal amplification performance of the signal amplification sandwich structure is related to the number of electroactive guanine per analyte. As an example of an embodiment of the invention, the amplification performance was set at ~9,500,000 guanine nucleotides per analyte by binding ~$4.75 \times 10^5$ oligonucleotide tags per multifunctional particle, with each oligonucleotide tag containing 20 guanine. It is necessary to ensure that the multifunctional particle used for the assay has sufficient surface area to fit the required number of oligonucleotide tags. In this example, ~$4.75 \times 10^5$ oligonucleotides can fit on a 1 micron spherical particle based the maximum packing density of oligonucleotides per surface area being ~$10^{12}/cm^2$. If additional amplification is required to attain a lower limit of detection, then adjustments can be made for using longer oligonucleotides, a greater number of guanines per oligonucleotide, a larger particle size, a particle material with a porous surface, an attachment to other particles, or combinations thereof.

The actual amplification performance needs to be validated for the number of analytes that bind with a unique multifunctional particle and a biosensor working electrode. Ideally each analyte could bind with a unique multifunctional particle. Statistically, some analytes may bind with multiple multifunctional particles and there is also the possibility that some analytes will not bind to any multifunctional particles. So statistically it is likely that there will be a reduced average yield of analytes linked to unique multifunctional particle-analyte conjugates and subsequently form signal amplification structures.

The amplification ratio of guanine molecules per analyte is limited by the size of the multifunctional particle that is used. A larger multifunctional particle will be able to bind with a larger number of electrochemically detectable oligonucleotide tags. In addition it is possible to place the electrochemically detectable tags on the inside of the delivery system or attach secondary structures to the multifunctional particles to further increase the available surface area. All of the factors impacting the tag amplification ratio need to be developed and validated for specific applications.

An innovative aspect of this invention is that the analyte amplification performance of the signal amplification sandwich structure can be tuned to meet the desired limit of detection by adjusting one or more parameters: (a) the number of electrochemically detectable oligonucleotide tags per multifunctional particle; (b) the number of guanines per electrochemically detectable oligonucleotide tag; (c) the size of the multifunctional particle for delivering electrochemically detectable oligonucleotide tags or electrochemical materials; and (d) the surface area of the multifunctional particle for conjugating electrochemically detectable oligonucleotide tags. As an illustration, the number of electrochemically detectable oligonucleotide tags per multifunctional particle ranges from $10^2$ to $10^{13}$, the number of guanines per electrochemical detectable oligonucleotide tag ranges from 10 to 400, wherein the multifunctional particles are spherical and/or nonspherical, the diameter of spherical multifunctional particles ranges from 0.05 to 400 micrometers, the surface area of nonspherical multifunctional particles has an equivalent surface area of spherical multifunctional particles with ranges from 0.05 to 400 micrometers, and the surface of the multifunctional particles is smooth, rough, porous, or extended with attachments to other particles.

In some embodiments the analyte binding materials 117a and 118a are antibodies that are used to bind analytes 101a that bind to antibodies and proteomic materials such as antigens, proteins, cells, and virus particles. In some embodiments the analyte binding materials 117b and 118b are oligonucleotides that are used to bind analytes 101b that hybridize with nucleic acids and genomic materials such as nucleic acids, RNA, DNA and genes. However, the analyte binding materials can be antibodies, monoclonal antibodies, polyclonal antibodies, amino acids, peptides, proteins, haptens, nucleic acids, oligonucleotides, DNA, RNA, aptamers, recombinant proteins, or combinations thereof.

The analyte binding materials 117a and 117b on the multifunctional particles 114 can be the same as the analyte binding materials 118a and 118b on the biosensor working electrodes, but typically are different. For example, antibodies would be selected based on the highest specificity that can be achieved for binding with the analyte along with a low cross reactivity with nonspecific materials including nonspecific strains or species of the analyte. A different antibody on the biosensor working electrode such as a polyclonal antibody would avoid the potential problem of the binding site being fully taken by the first antibody on multifunctional particles.

Another innovative aspect of this signal amplification detection structure is that the particle 114 also has an inner structure 116 that is multifunctional, whereby one or more functions can be provided by the structure in addition to or to enhance analyte amplification, detection and/or quantification. Multifunctionality is provided in part by selecting a material for the inner structure 116 that provides the desired functionality. In one embodiment the multifunctional particles have an inner structure consisting of a magnetic material. When a magnetic field is applied, multifunctional particles along with analytes attached to the multifunctional particles though the analyte binding materials are attracted to the magnetic field and are separated from nonspecific materials that can inhibit detection and cause false detection signals. In another embodiment an optical bar code in the inner structure can allow the identification of specific forms of the analyte such as strains, species, serotypes, sequence or other classification. In another embodiment, a chemical material in the inner structure can be released to kill pathogenic analytes or cancer cells.

In some embodiments a plurality of an analyte binding material is bound to the external surface of the particle, and a plurality of an electrochemically detectable oligonucleotide tag is provided inside a hollow particle. In these embodiments, the particles can be opened in order to release or expose the electrochemically detectable oligonucleotide tags for detection or other materials for additional applications such as medical treatment or environmental remediation.

Referring to the multifunctional structures as particles, the multifunctional particles are for delivering said electrochemically detectable oligonucleotide tags to the analyte, wherein the inner structure of said multifunctional particles is selected from the group consisting of structural materials, magnetic materials, optical materials, nuclear materials, radiological materials, quantum materials, biological materials, energetic materials, electrochemical materials, chemical materials, pharmaceutical materials, antibiotic materials, chemotherapy materials, and combinations thereof. The outer layer would facilitate binding with the analyte binding material and also with the electrochemically detectable oligonucleotide tags.

Amplification, Detection, Quantification and Diagnosis Method

Figure 7:
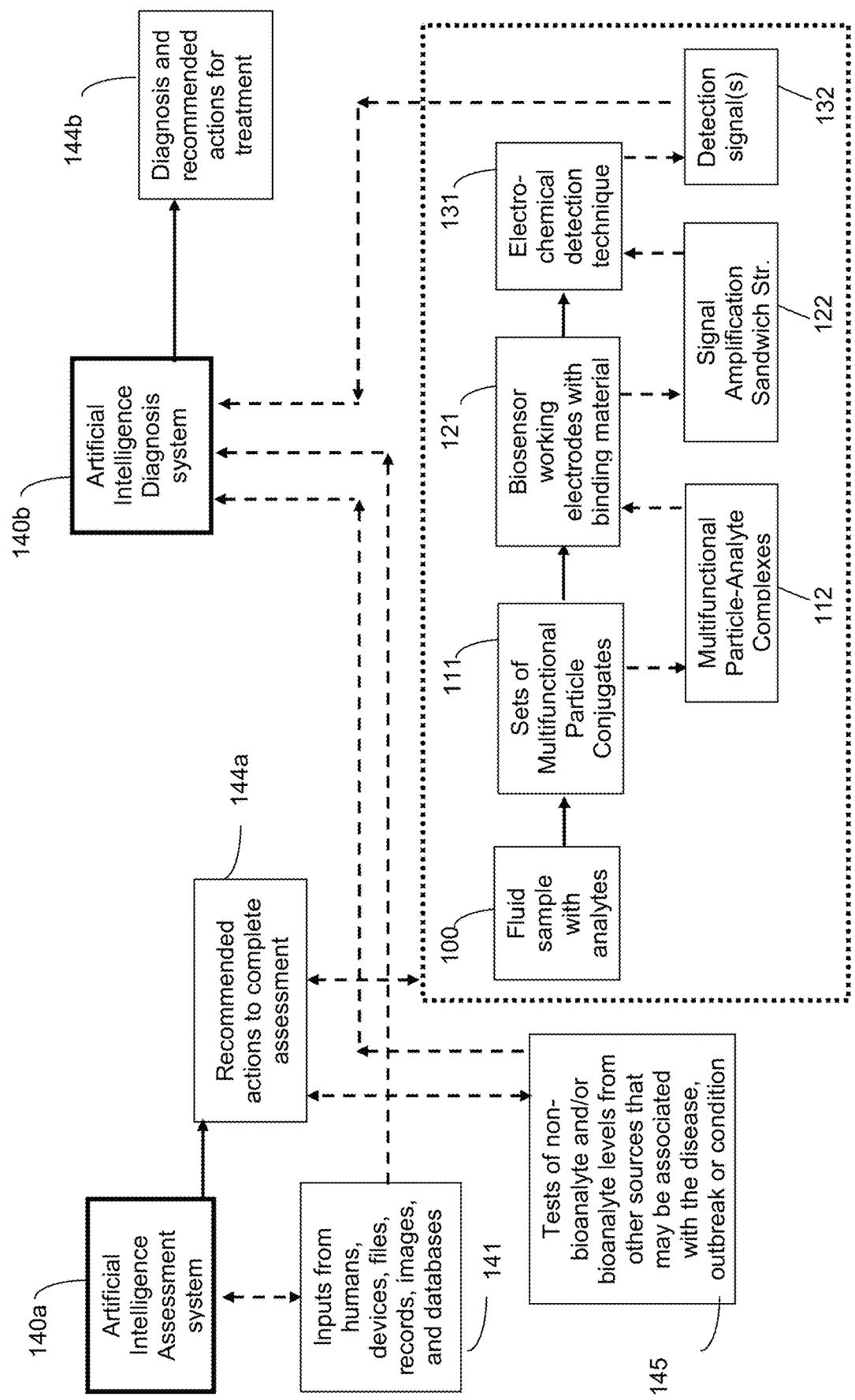
FIG. 7 shows a flow chart generally illustrating a method for amplifying, detecting and/or quantifying one or more analytes in a fluid sample, and diagnosing a disease, outbreak or condition according to an embodiment of the present invention.

Referring to FIG. 7, a flow chart is shown illustrating the main steps of an embodiment of a method for amplifying, detecting, and/or quantifying an analyte or multiple different analytes in a fluid sample and diagnosing a disease, outbreak or condition. The method comprises: (a) providing an artificial intelligence assessment system 140a to recommend actions for assessment of the disease, outbreak or condition from inputs 141 and other tests 145; (b) providing a means for amplifying, detecting and/or quantifying one or more analytes in the fluid sample consisting of: i. providing a fluid sample 100 that may contain nonspecific materials and one or more analytes, ii. providing one or more sets of multifunctional particle conjugates 111, wherein each set comprises a plurality of multifunctional particles conjugated with a plurality of a first analyte binding material and is also conjugated with a plurality of an electrochemically detectable oligonucleotide tag in greater amounts than said analyte to create multifunctional particle-analyte complexes 112 if a complementary analyte is present, iii. providing one or more biosensor working electrodes 121 or sorbents situated near the biosensor working electrodes, wherein each biosensor working electrode comprises a plurality of a second analyte binding material to create signal amplification sandwich structures 122, iii. providing an electrochemical detection technique 131 that produces peak electrochemical detection signals 132 on each biosensor working electrode in proportion to the level of a complementary analyte if said analyte is present in the fluid sample; (c) providing one or more test results consisting of analyte quantities, and non-bioanalyte and/or bioanalyte levels from other sources that may be associated with the disease, outbreak or condition 145, (d) providing an artificial intelligence diagnosis system 140b to diagnose and recommend actions for treatment of the disease, outbreak or condition 144b based on electrochemical detection signals 132, test results consisting of non-bioanalyte and/or bioanalyte levels 145, and (e) providing an artificial intelligence learning system to incorporate improvements, additions and modifications to the artificial intelligence systems and its constituents.

The artificial intelligence assessment system and the artificial intelligence diagnosis system each comprise: (1) an input system to obtain answers, medical histories, allergies, predispositions and symptoms from doctors, patients, operators and other people, and to import one or more of images, signals and data from sensors, devices, instruments, actuators, smart phone, computers, databases, records, files, and combinations thereof; (2) a knowledge base comprising one or more of deterministic rules, mathematical models, concentration formulas, image and pattern recognition, Boolean logic, algorithms, standards, changes of parameters over time, rate, temperature, environmental conditions, phases, reactions, events, treatments, remedies, guidelines, regulations, standards, norms, diseases, outbreaks, conditions, other pertinent information and combinations thereof; and (3) an inference engine to interpret inputs, data knowledge base in order to provide recommended actions to complete the assessment and/or diagnosis.

Figure 8:
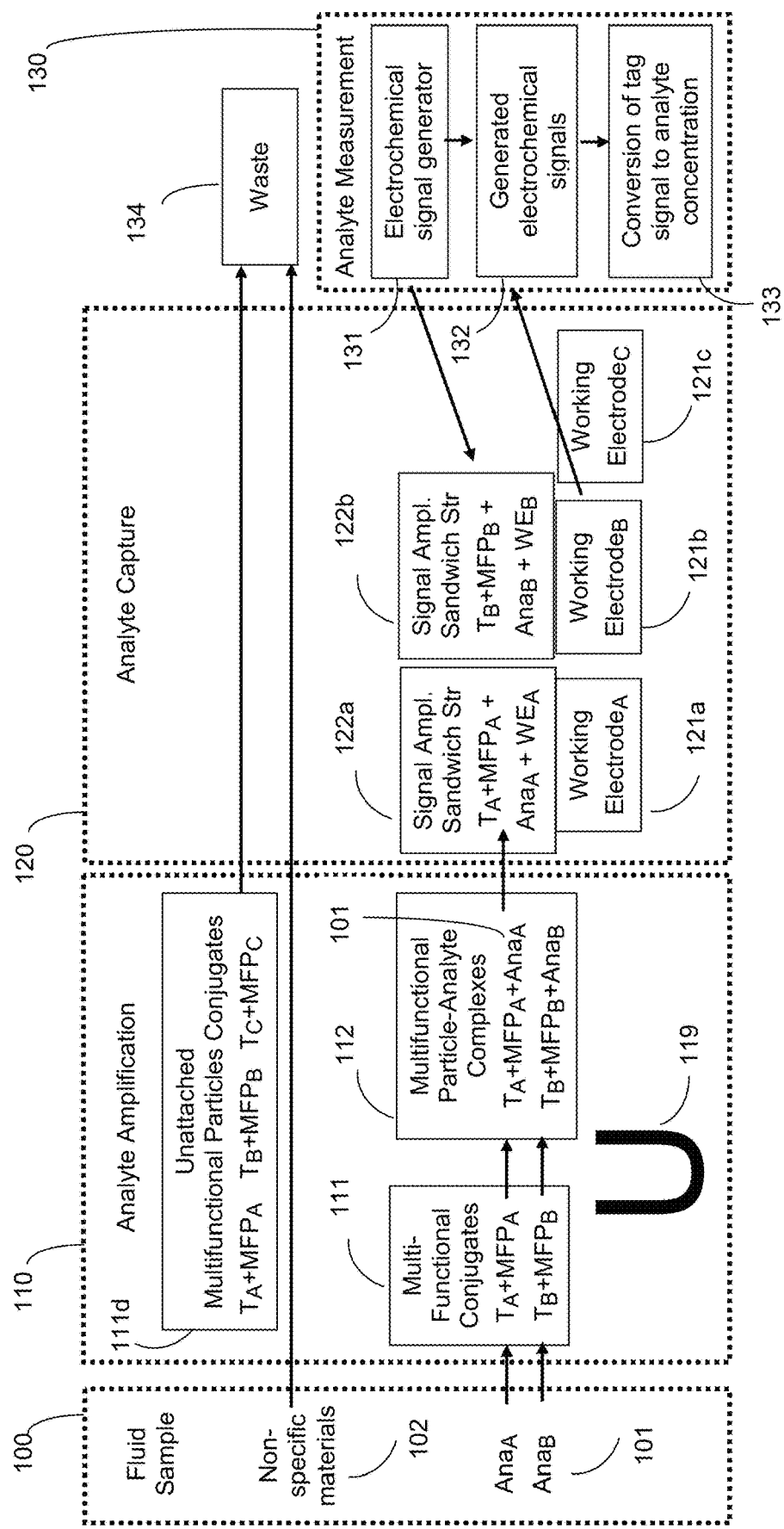
FIG. 8 shows a detailed flow chart illustrating a method for amplifying, detecting and/or quantifying one or more analytes in a fluid sample according to an embodiment of the present invention.

Referring to FIG. 8, a detailed flow chart is shown illustrating the main steps of an embodiment of a method for amplifying, detecting, and/or quantifying an analyte or multiple different analytes in a fluid sample.

Analyte Amplification

The method includes an analyte amplification step for binding a large quantity of electrochemically detectable oligonucleotide tags to analytes in order to improve the ability of detecting low abundance analytes. The fluid sample 100 containing nonspecific materials 102 and may also contain analytes 101 is provided to sets of multifunctional particle conjugates 111 bound with electrochemically detectable oligonucleotide tags 111. Analytes 101 bind with multifunctional particle conjugates which have analyte binding materials that bind with the analytes and form multifunctional particle-analyte complexes 112 for each analyte in the solution. Nonspecific materials 102 and unbound multifunctional particle conjugates 111 that are not bound to analytes because their corresponding analytes are not present in fluid sample 100 or are present in a low quantity so that all analyte-multifunctional particles have already been bound to tags, are delivered to a waste reservoir or wick 134.

In another embodiment, the fluid sample 100 that may contain nonspecific materials and one or more analytes are provided to the analyte amplification process 110. Also provided is one of more sets of multifunctional particle conjugates 111 wherein each set also comprises a plurality of an analyte binding material that conjugates with an analyte to be detected if the associated analyte is present in the sample. For example a first multifunctional particle set $MFP_A$ is associated with extracting analyte $Ana_A$, a second multifunctional particle set $MFP_B$ is associated with extracting analyte $Ana_B$, and a third multifunctional particle set $MFP_C$ is associated with extracting analyte $Ana_C$.

Figure 3:
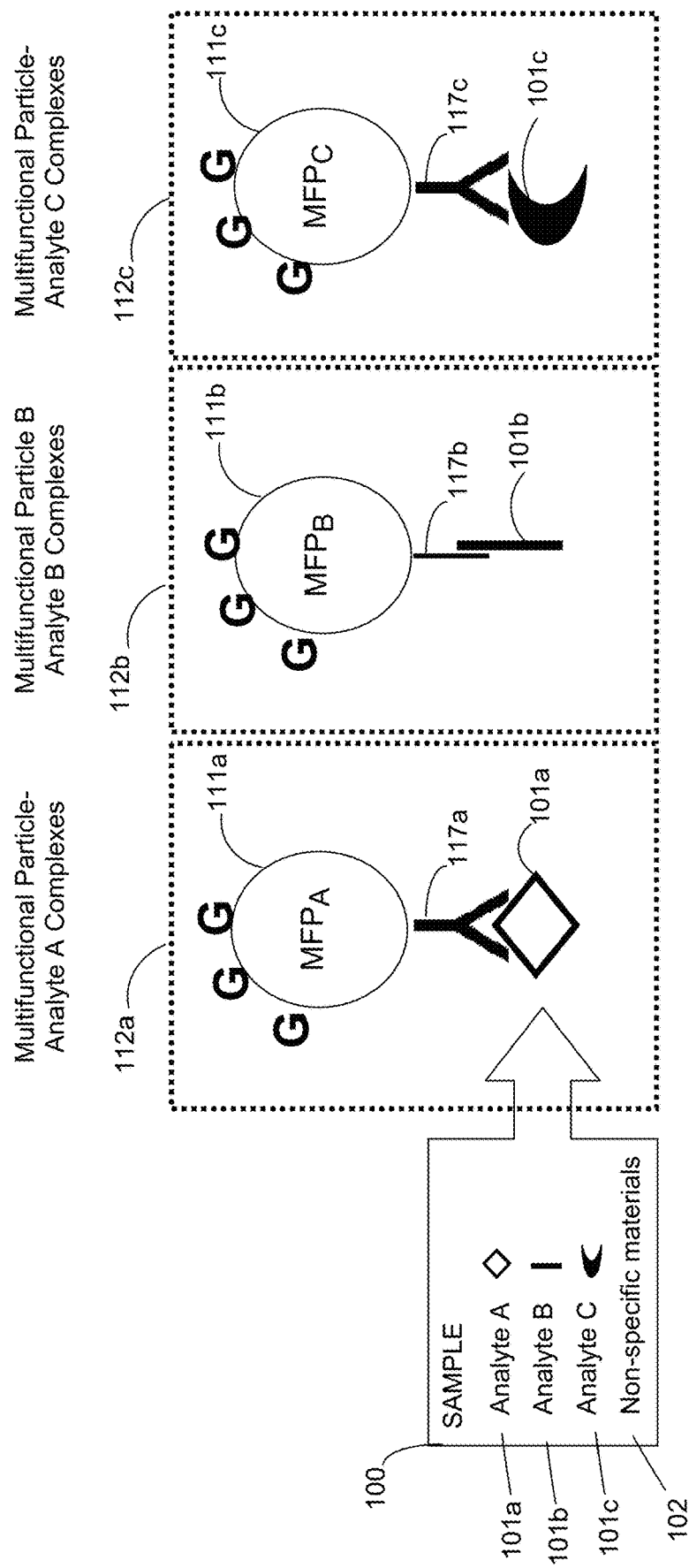
FIG. 3 is a schematic representation of multifunctional particle-analyte complexes.

Referring to FIG. 3, as an example, the fluid sample 100 comprises 3 different analytes: microorganism analyte A 101a, nucleic acid analyte B 101b, and protein analyte C 101c along with nonspecific materials 102. There is also provided sets of multifunctional particle conjugates 111a, 111b. 111c. The first multifunctional particle set $MFP_A$ in the conjugate 111a Is associated with extracting analyte $Ana_A$ 101a and is conjugated with a suitable analyte binding material 117a. Each set of multifunctional particle conjugates 111a, 111b, 111c, would have its own analyte binding material 117a, 117b 117c that is used to bind to the associated analyte. In the case of a cell, bacteria, virus particle or protein, the analyte binding material can be an antibody, and preferably a highly specific monoclonal antibody. In the case of a nucleic acid the analyte binding material can be a complementary DNA probe. Other analyte binding materials can also be provided. The first multifunctional particle set $MFP_A$ in conjugate 111a would form a multifunctional particle A-analyte A complex $MFP_A$-$Ana_A$ 112a should analyte A 101a be present in the fluid sample and bind with analyte binding material 117a which is conjugated with the multifunctional particle set $MFP_A$ in conjugate 111a. While this example illustrates the presence of 3 sets of multifunctional particles associated with three different analytes, it should be clear that a plurality of sets of multifunctional particles can be employed for multiplexed and multi-analyte applications. In some embodiments a set of multifunctional particle conjugates may be associated with an analyte. In some embodiments a set of multifunctional particle conjugates may be associated with a group of multiple different analytes. In some embodiments multiple sets of multifunctional particle conjugates may be associated with an analyte. The method described herein can be adapted to a variety of other samples and analyte configurations.

Referring again to FIG. 8, the fluid sample 100 is delivered to multifunctional particle conjugates 111 for analyte amplification. In some embodiments the fluid sample and multifunctional particle conjugates are mixed by mechanical agitation, diffusion, or other method. The analytes bind with the associated sets of multifunctional particle conjugates to form multifunctional particle-analyte complexes, if the analytes are present in the fluid sample.

The analyte amplification step may optionally include one or more steps for pre-treating the fluid sample. In one embodiment, a membrane is used to prevent large materials from entering the mixing chamber. In another embodiment, a membrane is used to concentrate analytes in a large sample volume by allowing filtered solution and small nonspecific materials to flow through the filter to a reservoir and retain the analyte concentrate for analyte amplification.

In another embodiment, a chemical such as an adherent could be employed to remove interfering materials. In another embodiment, a disaggregation technique such as a chemical surfactant, sonication or hydrodynamic cavitation can be employed to disaggregate clumps potentially containing target analytes. In another embodiment, the method includes a step for improving detection accuracy by extracting analytes from nonspecific materials to reduce the incidence of undesirable false negative and false positive detection outcomes using magnetic separation. This step has the added benefit of improving the detection signal-to-noise ratio by reducing the background noise cause by nonspecific materials.

In one embodiment, the multifunctional particles 114 are comprised of magnetic materials in their inner structures and a magnetic field 119 is applied to draw the multifunctional particle-analyte complexes 112 away from nonspecific materials by immobilizing the complexes while the nonspecific materials and fluid solution flows to a waste reservoir or wick 134. Washes can optionally be added to the process to flush nonspecific materials from the complexes temporarily held under the magnetic field. In this example, the multifunctional particle-analyte complexes 112 for analyte A, $MFP_A+Ana_A$, and analyte B, $MFP_B+Ana_B$, are magnetically separated. In this example there is no analyte C. Multifunctional particle conjugates 111 that do not form complexes are also magnetically extracted.

Analyte Capture

Referring to FIG. 8, the multifunctional particle-analyte complexes 112 from the analyte amplification process 110 are then provided to the analyte capture process 120 to produce signal amplification sandwich structures. Said analyte capture process provides one or more biosensor working electrodes conjugated with a plurality of an analyte binding material on or near the biosensor working electrodes. For example, the biosensor working electrodes with analyte binding materials 121a, 121b, 121c, . . . are used for capturing the associated analytes in the multifunctional particle-analyte complexes 112a, 112b, 112c, . . . if the analyte in the conjugate binds with the analyte binding materials on the working electrodes. Once the complexes are captured, they form signal amplification detection structures.

Referring to FIG. 3, as an example, the multifunctional particle-analyte complexes 112 may contain 3 sets of multifunctional particle-analyte complexes 112a, 112b, 112c, associated with three analytes: microorganism analyte A 101a, nucleic acid analyte B 101b and protein analyte C 101c. There is also provided sets of biosensor working electrodes with analyte binding materials 121a, 121b, 121c. The first biosensor working electrode with analyte binding materials 121a Is associated with detecting or quantifying analyte $Ana_A$ 101a and is conjugated with a suitable analyte binding material 118a which may bind with analyte A 101a conjugated to the multifunctional particle A-analyte A complex 112a.

Figure 4:
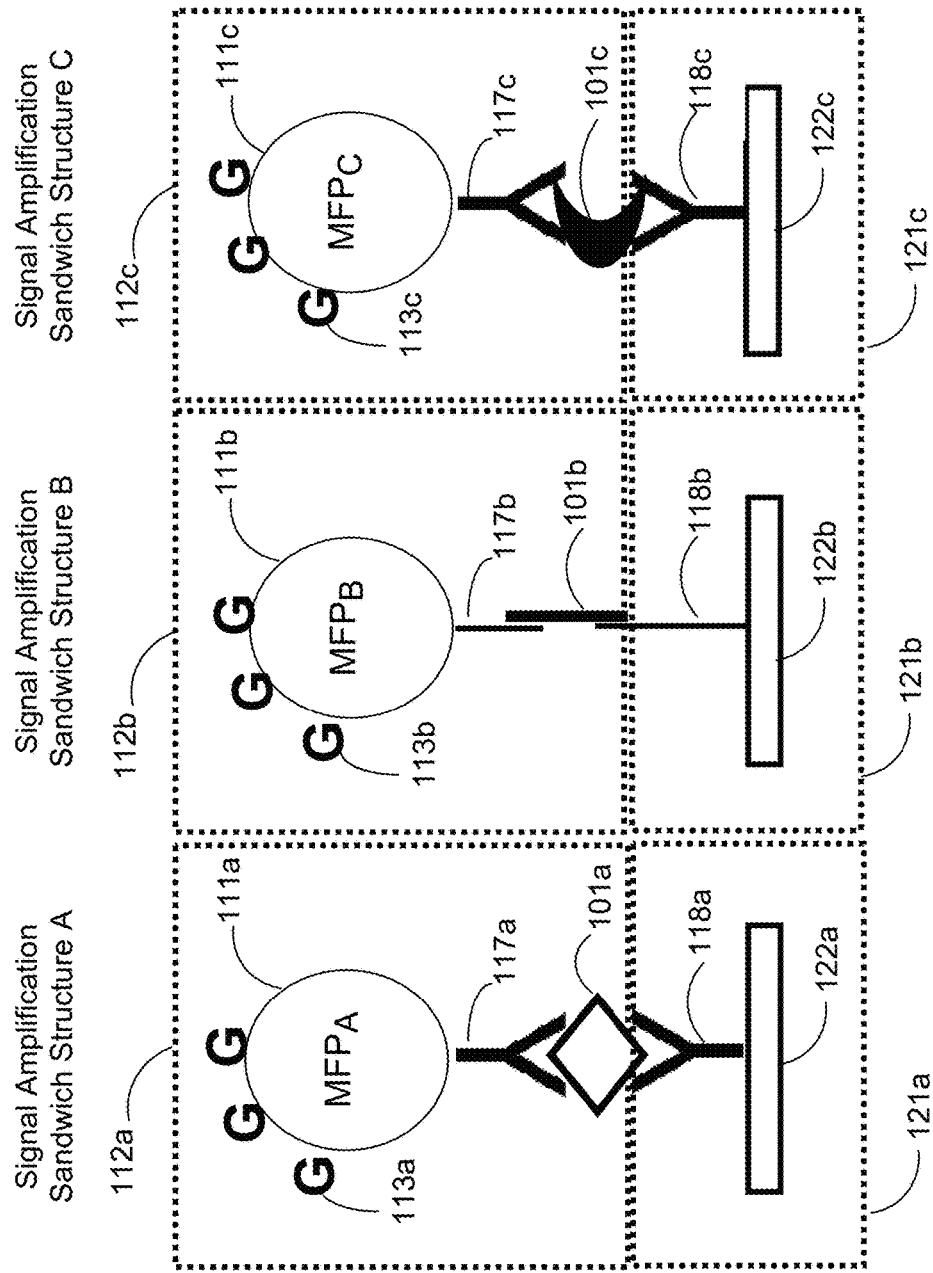
FIG. 4 is a schematic representation of electrochemically detectible oligonucleotide sandwich structures according to one embodiment of the invention.

Referring to FIG. 4, as an example, each biosensor working electrode 122a, 122b, 122c, would have its own analyte binding material 118a, 118b, 118c that is used to bind to the associated analyte 101a, 101b, 101c, and may be the same as or different than the analyte binding materials 117a, 117b, 117c conjugated to the multifunctional particles 111a, 111b, 111c. In the case of a cell, virus particle or protein, the analyte binding material can be an antibody, and preferably a highly specific monoclonal antibody. In the case of a nucleic acid the analyte binding can be a complementary DNA probe. Other analyte binding materials can also be provided.

Figure 6:
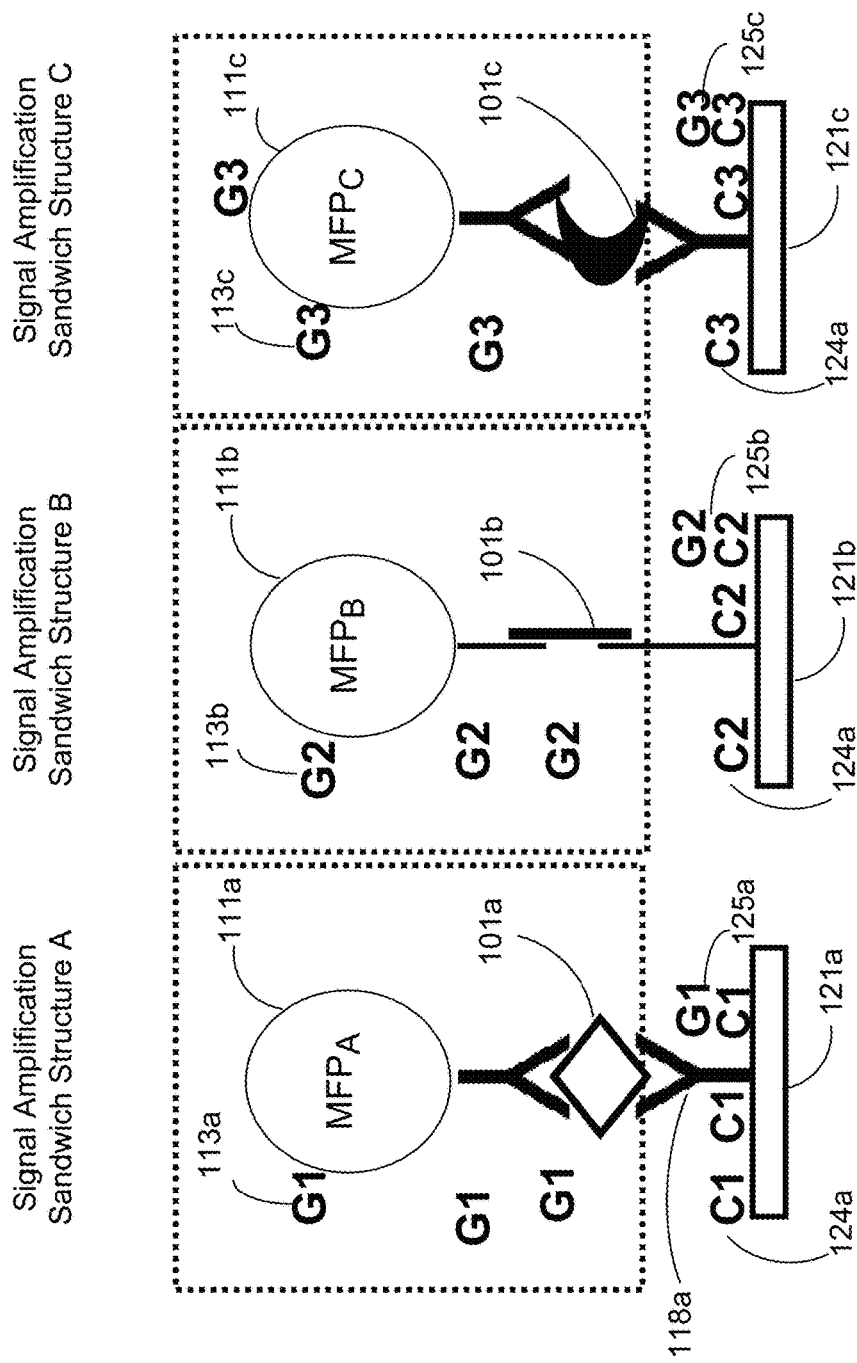
FIG. 6 is a schematic representation of electrochemically detectible oligonucleotide sandwich structures according to one embodiment of the invention.

The signal amplification sandwich structure 122a containing the multifunctional particle A-analyte A complex $MFP_A-Ana_A$ 112a is also conjugated with a plurality of detectable tags 113a. Referring to FIG. 6, in one embodiment the tags 113a are electrochemically detectable oligonucleotide tags comprising quadruplex structures, wherein the majority of the nucleotides within said structures are guanine with at least 4 guanines in a consecutive sequence; wherein sets of 4 guanine comprise square planar tetrad structures bound by eight Hoogsteen hydrogen bonds, wherein two or more square planar tetrad structures are stacked on top of each other and stabilized by pi-pi hydrophobic interactions, wherein between each square planar tetrad structure in the stack is a monovalent cation which is coordinated to the lone pairs of electrons of O6 in each guanine; wherein the quadruplex electrochemically detectable oligonucleotides are exposed, adsorbed or hybridized to a biosensor working electrode surface wherein a redox detection technique oxidizes guanine and produces 8-oxoguanine signals; and wherein the majority of the nucleotides within said single-stranded oligonucleotide detection tags are guanine, and when used for detecting and/or quantifying multiple analytes simultaneously from the same sample, the nucleotides within the single-stranded oligonucleotide detection tags are selected from the group consisting of guanine, adenine, thymine, and cytosine, and wherein the combination of said nucleotides produces a unique oligonucleotide tag that is used to detect and/or quantify a specific analyte or group of specific analytes.

In another embodiment the electrochemically detectable oligonucleotide tags are single stranded oligonucleotides with 20-500 bases with the majority being guanine. In the event of the determination of multiple target analytes from the same sample, the tags will be slight variations with the majority being guanine in non-random placements of guanine, adenine, thymine, and cytosine. In one embodiment, the electrochemically detectable oligonucleotide tags are the same. In another embodiment, the electrochemically detectable tags are different. In another embodiment, the electrochemically detectable oligonucleotide tags are eluted or denatured from the signal amplification sandwich structures and are exposed, adsorbed, and/or hybridized to one or more biosensor working electrodes in order for analytes to be measured. Referring to FIG. 6, in this embodiment, the tags 113a, 113b, 113c, . . . are eluted and hybridize with a complementary oligonucleotide probe 124a, 124b, 124c, . . . on or near the surface of the biosensor working electrode 121a, 122b, 122c, . . . to form duplexes 125a, 125b, 125c, . . . which allow detection signals to be produced for each associate analyte.

The number of electrochemically detectable oligonucleotide tags must exceed the number of associated analytes, preferably by several orders of magnitude, in order to amplify the analyte detection signal. In one embodiment there are $10^6$ electrochemically detectable oligonucleotide tags bound to each multifunctional particle. Each of the oligonucleotide tags contains about 20 guanine nucleotides. This produces an amplification ratio of about $2 \times 10^7$ guanine nucleotides per analyte. In every situation the amplification ratio of guanine to target analyte needs to be statistically calibrated to account for losses from the sample composition and volume, the analyte binding materials, the type and concentration of the analytes, the type and amount of non-specific materials in the sample, etc.

Figure 5:
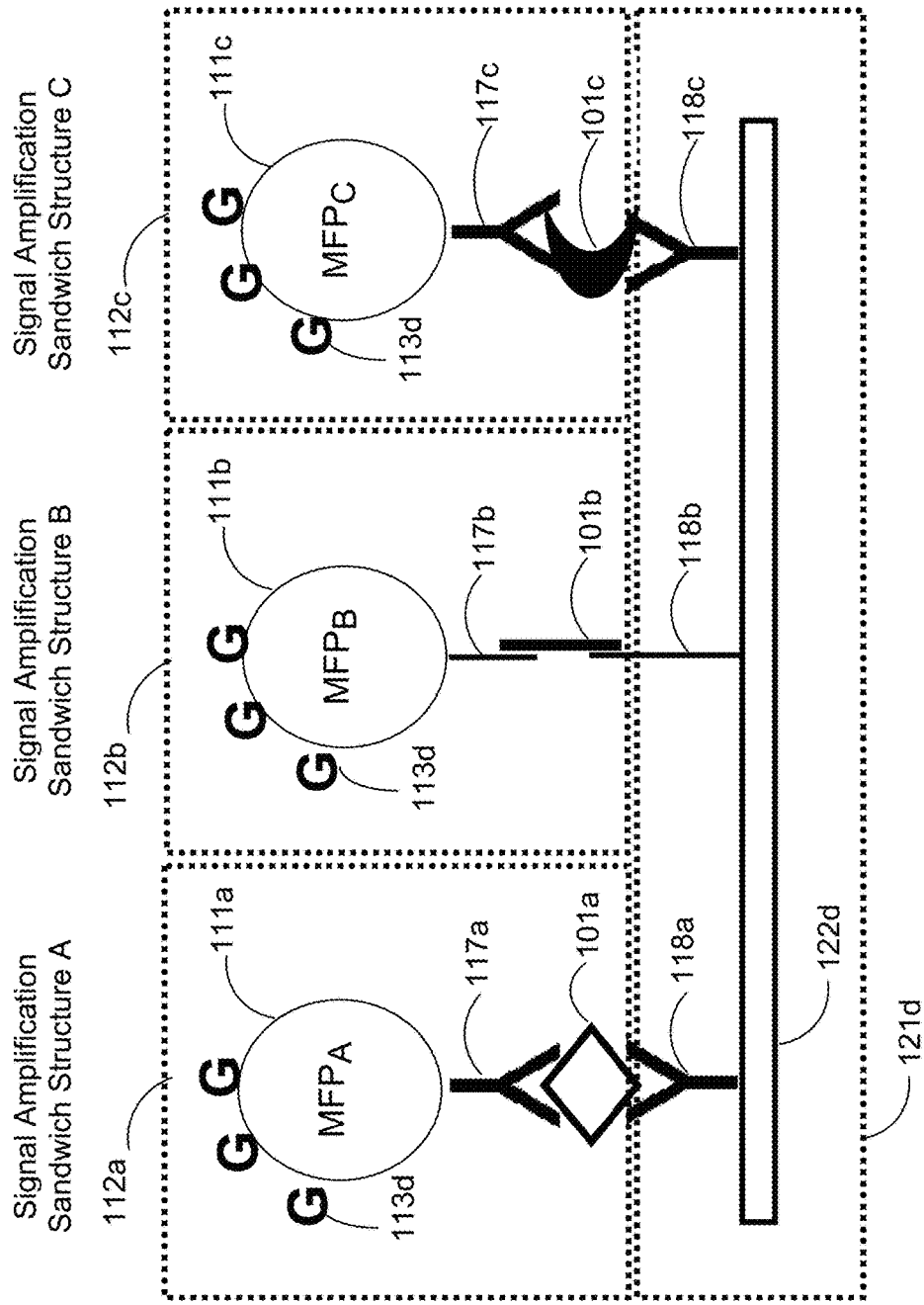
FIG. 5 is a schematic representation of electrochemically detectible oligonucleotide sandwich structures according to one embodiment of the invention.

Referring to FIG. 4, each multifunctional particle conjugate may bind to one individual biosensor working electrode to allow individual analytes to be detected and quantified. Referring to FIG. 5, many multifunctional particle conjugates may bind to one common working electrode to any analyte in a group of analytes to be detected and quantified. This feature allows for a high number of analytes to be detected at a very low cost. Referring again to FIG. 8, in the abovementioned example a first multifunctional particle conjugate 111a and multifunctional particle-analyte complex 112a are associated with amplifying, detecting and/or quantifying analyte A $Ana_A$ 101a, a second multifunctional particle conjugate 111b and multifunctional particle-analyte conjugate 112b are associated with amplifying, detecting and/or quantifying analyte $Ana_B$, 101b and a third multifunctional particle conjugate 112c is associated with amplifying, detecting and/or quantifying analyte $Ana_C$ 101c. In this example, analyte C $Ana_C$ 101c is not present in sample 100.

The complexes 112 are delivered to the biosensor working electrodes conjugated with analyte binding materials 121 by lateral flow, mechanical agitation, diffusion, or other method. The analytes on the conjugates then bind with the associated sets of analyte binding materials on the biosensor working electrodes to form signal amplification detection structures if the multifunctional particle-analyte conjugates are present.

Nonspecific materials 102 and unbound multifunctional particle conjugates 111d are delivered to the waste reservoir or wick 134 along with multifunctional particle conjugates associated with analyte C, since there is no analyte C in the fluid sample. In this example there is also a low abundance of analyte A and analyte B in the fluid sample 100. As a consequence, all analyte A and analyte B are bound to multifunctional particle complexes leaving a surplus of unbound multifunctional particle conjugates associated with analyte A and analyte B. These surplus unbound multifunctional particle conjugates will also be delivered to the waste reservoir or wick 134.

In some embodiments the multifunctional particles have a magnetic material interior. A magnetic field 119 is applied to separate multifunctional particle conjugates and multifunctional particle-analyte complexes from nonspecific materials in the fluid sample by magnetically immobilizing the conjugates and complexes while the waste solution with nonspecific materials is flushed away to a waste reservoir or wick 134. While this example illustrates the presence of 3 sets of multifunctional particles and biosensor working electrodes associated with three analytes, it should be clear that a plurality of sets of multifunctional particles and biosensor working electrodes can be employed for multiplexed and multi-analyte applications. The method described herein can be adapted to a variety of other samples, analyte configurations, and types of electrochemically detectable oligonucleotide tags.

Analyte Measurement

The method next includes an analyte measurement step 130 for generating electrochemical signals from electrochemically detectable oligonucleotide tags. The tags are on signal amplification sandwich structures associated with analytes. The amplitude of the generated signals are used to determine the presence and/or quantity of electrochemically detectable oligonucleotide tags bound to the biosensor working electrodes, which correlate to the presence and/or quantity of associated analytes in the fluid sample. Referring to FIG. 8, the method provides an electrochemical signal generator 131 and electrochemical measurement technique. As will be readily understood by those skilled in the art, the method can readily be adapted to support other electrochemical measurement techniques such as voltammetry, potentiometry, coulometry, conductimetry, AC voltammetry, differential pulse voltammetry, square wave voltammetry, electrochemical impedance spectroscopy, anodic stripping voltammetry, cyclic voltammetry, or fast scan cyclic voltammetry. The electrochemical detection system further provides a counter electrode, a reference electrode, and optionally a reservoir for providing a mediator and/or other required electrochemical selection capabilities as is readily understood by those skilled in the art.

In one embodiment the electrochemical signal generator 131 applies a potential scan across a range of potentials to create an electrical current flowing between a counter electrode and one or more working electrodes through a liquid solution. The liquid solution is one or more of the liquid sample 100, the filtered liquid sample, a buffer, a mediator, and other liquid that can facilitate electrochemical detection.

The method continues by generating electrochemical signals 132 from the electrochemically detectable oligonucleotide tags using the electrochemical measurement technique. In one embodiment the electrochemically signals are from guanine oxidation, the electrochemically detectable oligonucleotide tags are single stranded oligonucleotides rich in guanine, and the electrochemical measurement technique is differential pulse voltammetry with a 25 mV/sec scan rate and the following settings: a pulse size of 20 mV, a step size of 5 mV, sample time of 1.5 seconds and pulse time of 0.1 seconds, applied potential from 0.50 volts to 1.20 volts.

In another embodiment the electrochemically signals are from 8-oxoguanine oxidation and the electrochemically tags are quadruplex oligonucleotides rich in guanine. The electrochemical measurement technique generates 8-oxoguanine signals. A square wave voltammetry scan was applied with a 1400 mV/sec scan rate and the following settings: scan increment 5 mV, frequency 280 Hz (0.0035/sec), pulse height 20 mV, equilibrium time 3 sec, initial E −0.35V, final E −1.2 V).

Figure 9B:
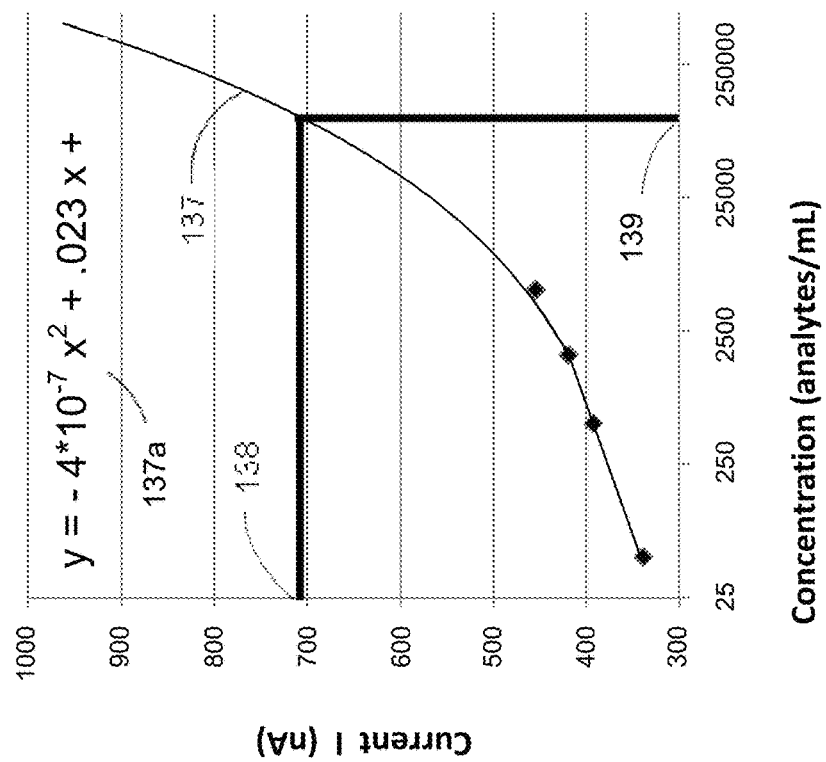
FIG. 9B is a graph of an analyte concentration curve plotting peak electrical current versus analyte level or concentration for quantifying test samples.
Figure 9A:
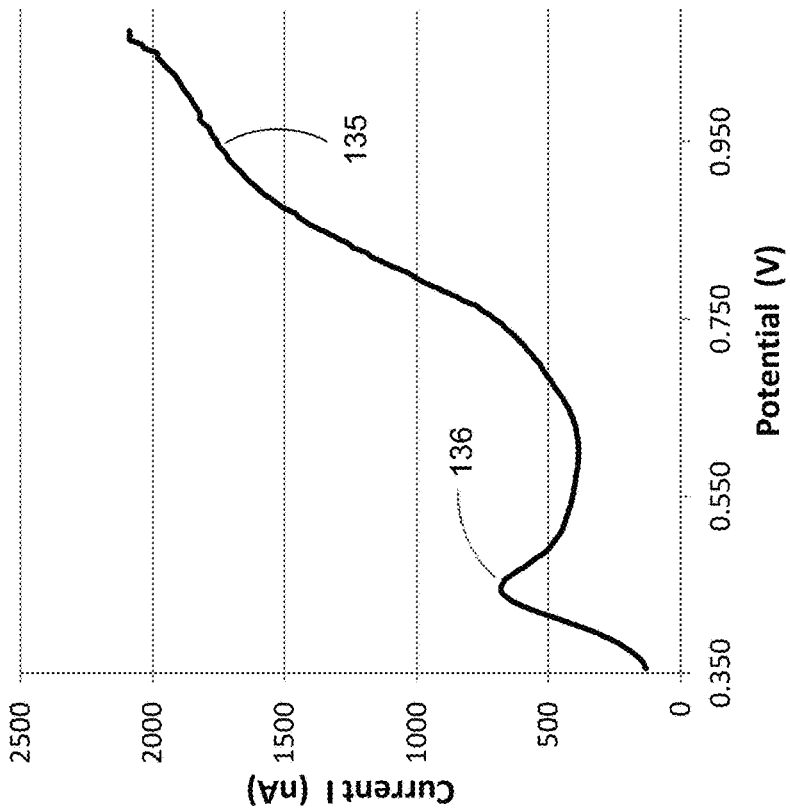
FIG. 9A is a graph of an electrochemical scan plotting electrical current versus potential.

Referring to FIG. 9A, the generated electrochemical signal 135 is plotted as current in nanoamps (nA) on the Y axis versus potential in volts (V) on the X axis. A peak signal 136 is produced at approximately 0.47V from 8-oxoguanine oxidation. The amplitude of the peak signal is proportional to the quantity of electrochemically detectable oligonucleotide tags in signal amplification detection structures bound to the biosensor working electrode, and is also proportional to the quantity of analytes in the sample being measured at the working electrode.

The method continues by measuring analytes by converting the peak electrochemical signals into analyte concentrations 133. Referring to FIG. 9B, analyte concentrations associated with known quantities of generated electrochemical signal 137 is plotted as generated electrochemical signal or electrical current in nanoamps (nA) on the Y axis versus analyte concentration on the X axis. The peak signal 138 which was produced as the peak signal 136 from FIG. 9A is plotted and the associated analyte quantity 139 is derived from the curve. In another embodiment, the slope of the curve is computed in a mathematical formula 137a which can be used to calculate the analyte quantity manually or automatically by programming the formula into a measurement instrument.

As will be readily understood by those skilled in the art, other techniques can be used to generate and convert electrochemical signals into analyte concentrations including but not limited to one or more of measuring the peak signal from the analyte sample minus the peak signal or variability from the negative control signal, measuring the average analyte peak signal from multiple portions of the same sample, adding a mediator to the sample and generating a first scan from the analyte plus mediator and a second scan from only the mediator, apply multiple scans to decrease noise and measuring a later scan after noise has been reduced, and measuring the signal under the curve 136.

Artificial Intelligence Assessment, Diagnosis, and Learning

Figure 10:
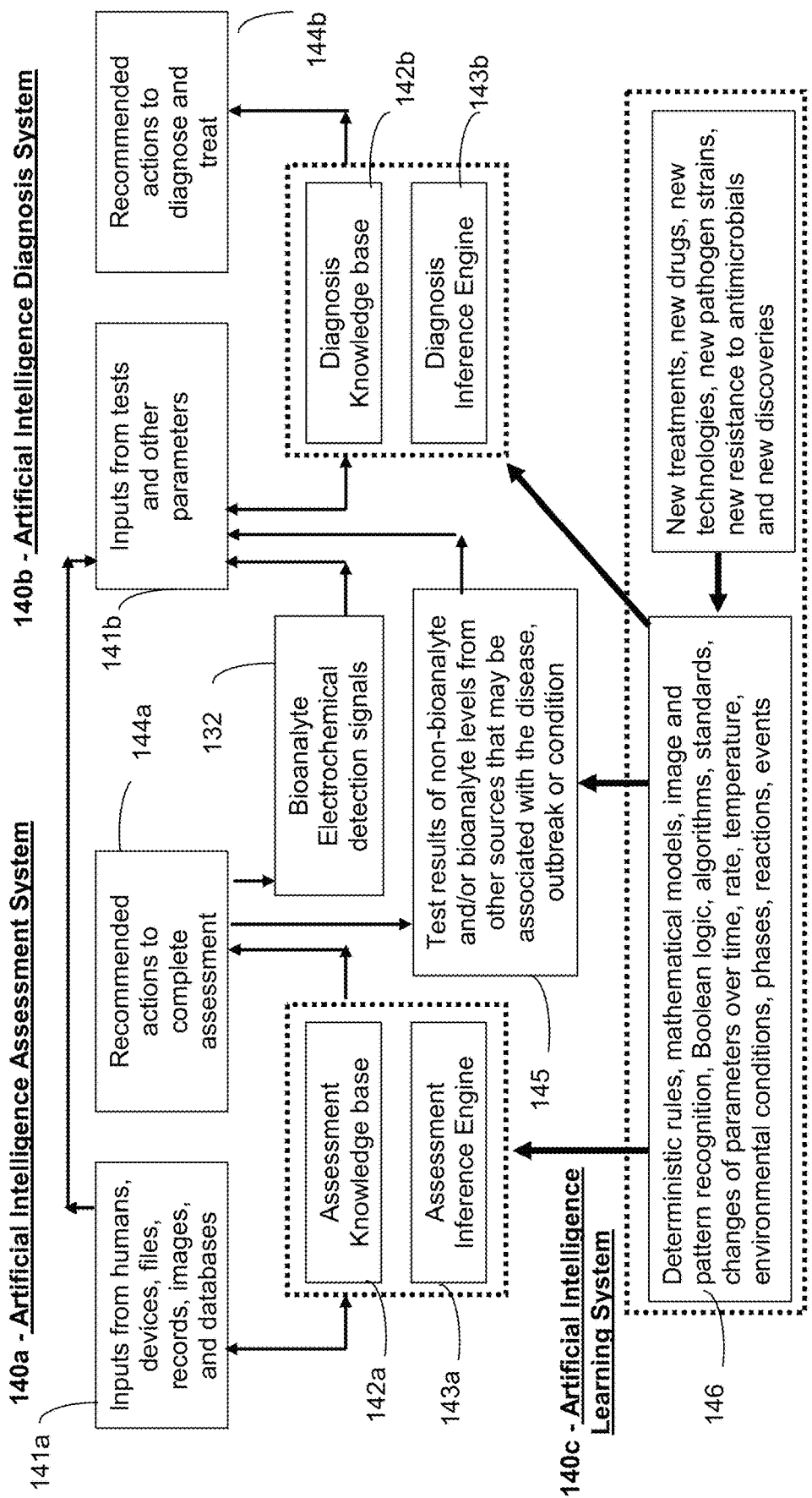
FIG. 10 is a schematic representation of the main components of an artificial intelligence method and device for diagnosing a disease, outbreak or condition according to an embodiment of the present invention.

The method further includes three artificial intelligence systems that improve the diagnostic performance of the analyte testing alone. Referring to FIGS. 7 and 10, the artificial intelligence assessment system 140*a* is initially used. An Input system 141*a* queries doctors, patients, operators and other people to obtain answers, medical histories, allergies, predispositions and symptoms pertaining to the disease, outbreak and condition. The input system further imports one or more of images, signals and data from sensors, devices, instruments, actuators, smart phone, computers, databases, records, files, and combinations thereof in order to obtain further clues about what could be needed to properly assess the situation. The artificial intelligence assessment system applies the inputs to its assessment knowledge base 142*a* which comprises one or more of deterministic rules, mathematical models, concentration formulas, image and pattern recognition, Boolean logic, algorithms, standards, changes of parameters over time, rate, temperature, environmental conditions, phases, reactions, events, treatments, remedies, guidelines, regulations, standards, norms, diseases, outbreaks, conditions, other pertinent information and combinations thereof. The artificial intelligence assessment system processes the information using assessment inference engine 143*a* in order to provide a recommendation for completing the assessment 144*a*. The recommendations can include specific analyte tests to be undertaken by the present invention. The assessment recommendation can also include tests of non-bioanalyte and/or bioanalyte levels from other sources that may be associated with the disease, outbreak or condition 145 as they may be required by regulations and guidelines.

It should be noted that the non-bioanalyte tests and particularly the bioanalyte tests are well recognized in the art. These may include one or more of immunoassays, culture, nucleic acid amplification testing, PCR, genomics, proteomics, other OMICs, microbiome, and tests with detection tags and instruments that are electrochemical, optical, other technologies, and/or direct detection.

After the requirements of the assessment recommendations are fully or partially met, the artificial intelligence diagnostic system 140*b* imports the relevant information from inputs 141*a*, bioanalyte electrochemical detection signals 132, and test results of non-bioanalyte and/or bioanalyte levels from other sources 145 and any other inputs that may be required to diagnose the disease, outbreak or condition 141*b*. The artificial intelligence assessment system applies the inputs to its assessment knowledge base 142*b* which comprises one or more of deterministic rules, mathematical models, concentration formulas, image and pattern recognition, Boolean logic, algorithms, standards, changes of parameters over time, rate, temperature, environmental conditions, phases, reactions, events, treatments, remedies, guidelines, regulations, standards, norms, diseases, outbreaks, conditions, other pertinent information and combinations thereof. The artificial intelligence diagnosis system processes the information using assessment inference engine 143*b* in order to provide a recommendation for treating the disease, outbreak or condition 144*b*

In one embodiment, regulatory authorities and/or experts develop guidelines that define specific treatments based on analyte concentrations being within or outside of acceptable ranges. The guidelines may recommend corrective actions and treatments so that analyte concentrations can be changed to provide acceptable levels in subsequent tests. Examples include biomarkers for infectious diseases, cancers, cardiac conditions and food safety. In these embodiment the artificial intelligence diagnosis system contains algorithms directly derived from these guidelines for converting analyte levels into recommended actions and treatments that can employ models and Boolean logic "IF-THEN" rules. In another embodiment, the system can also rule out certain diseases if analytes are not present or if the analytes or other information positively confirm that the disease is not present. As will be readily understood by those skilled in the art, other input parameters may need to assessed to improve diagnosis beyond analyte concentrations alone. In another embodiment the diagnosis and recommendations include one or more of positive outcome, negative outcome, probabilistic outcome, undetermined outcome, alternative outcome, analyte level, do nothing, specific treatment, additional test, other action, and combinations thereof.

Another unique aspect of the method is that the guidelines and recommendations are effective at a certain point in time but can become obsolete with the discovery of new treatments, new drugs, new technologies, new pathogen strains, new resistance to antimicrobials and many factors that have not yet been discovered. As a consequence the present invention will have a learning system 146 that can incorporate additions and modifications to any portion of the artificial intelligence system and its constituents.

Different Method Configurations

The method can also be used in different configurations. In one embodiment the method for amplifying an analyte or multiple different analytes in a fluid sample comprises a) providing the fluid sample, b) providing one or more sets of multifunctional particle conjugates, c) providing one or more sets of biosensor working electrodes to create signal amplification sandwich structures. In another embodiment the method for amplifying, detecting and/or quantifying an analyte or multiple different analytes in a fluid sample comprises a) providing the fluid sample, b) providing one or more sets of multifunctional particle conjugates, c) providing one or more sets of biosensor working electrodes to create signal amplification sandwich structures, and d) providing an electrochemical detection technique that produces electrochemical detection signals on each biosensor working electrode in proportion to the level of a complementary analyte if said analyte is present in the fluid sample.

In another embodiment the method for detecting, and/or quantifying an analyte or multiple different analytes in a fluid sample and diagnosing a disease, outbreak or condition comprises a) providing the fluid sample, e) providing an artificial intelligence system that interprets other input parameters to diagnose a disease, outbreak or condition where the fluid sample detects and/or quantifies an analyte or multiple different analytes using detection tags and instruments that are electrochemical, optical, other technologies, and/or by direct detection of the analytes.

Amplification, Detection, Quantification and Diagnosis Device

Figure 12A:
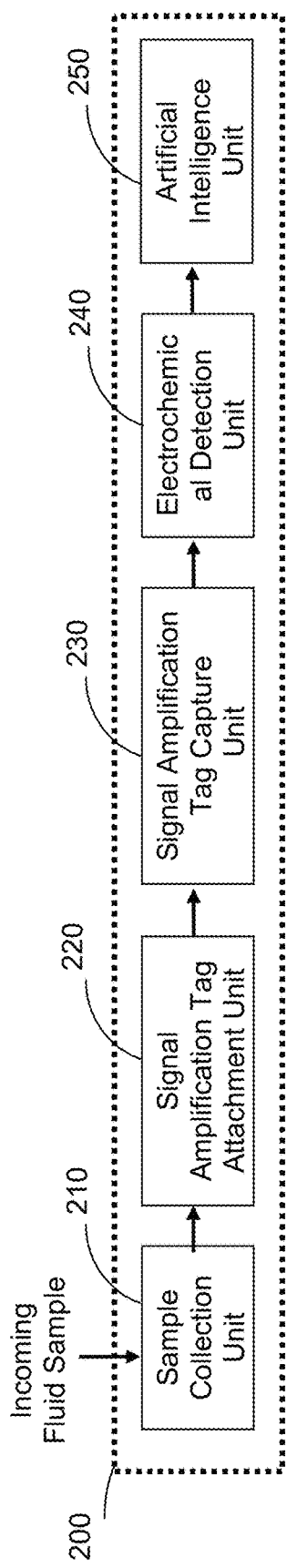
FIGS. 12A and 12B are schematic representations of a device for amplifying, detecting and/or quantifying an analyte or multiple different analytes in a fluid sample and diagnosing a disease, outbreak or condition according to embodiments of the present invention.

Referring to FIG. 12A, the main units are shown of a device 200 for amplifying, detecting and/or quantifying an analyte or multiple different analytes in a fluid sample, and diagnosing a disease, outbreak or condition. The device comprises a) a sample collection unit 210 configured to collect said fluid sample, b) a signal amplification tag attachment unit 220 configured to form a first outer layer and inner layer of signal amplification sandwich structures, c) a signal amplification tag capture unit 230 configured to form a second outer layer of signal amplification sandwich structures, d) an electrochemical detection unit 240 with at least one biosensor working electrode configured to measure detection signals from the electrochemically detectable oligonucleotide tags contained on said signal amplification sandwich structures, and e) an artificial intelligence unit 250 that interprets detection signals along with other input parameters to diagnose a disease, outbreak or condition.

The device first includes a sample collection unit 210 comprising an inlet port for receiving the fluid sample that may contain nonspecific materials and an analyte or multiple different analytes. The sample collection unit also includes a reservoir or sample pad for collecting or absorbing fluid. The sample collection unit is in fluid communications with the signal amplification tag attachment unit 220 to facilitate the movement of the analyte or multiple different analytes to the signal amplification tag attachment unit.

The device next includes a signal amplification tag attachment unit 220 comprising one or more sets of multifunctional particle conjugates, wherein each set comprises a plurality of multifunctional particles conjugated with a plurality of an analyte binding material and also conjugated with a plurality of electrochemically detectable oligonucleotide tags in greater amounts than the bound analyte to form multifunctional particle-analyte complexes if an associated analyte is present. The signal amplification tag attachment unit is in fluid communications with the signal amplification tag capture unit 230 to facilitate the movement of the multifunctional particle-analyte complexes to the signal amplification tag capture unit.

The device next includes a signal amplification tag capture unit 230 comprising one or more biosensor working electrodes which are used to capture and bind analytes contained in multifunctional particle-analyte complexes. The biosensor working electrodes used for amplifying, detecting and/or quantifying an analyte or multiple different analytes are conjugated with a plurality of an analyte binding material on or near the biosensor working electrode surface for capturing and binding the analyte or multiple different analytes and forming signal amplification sandwich structures from the multifunctional particle-analyte complexes if the analyte is present. The remaining constituents of the fluid sample include nonspecific materials and multifunctional particle conjugates that do not form multifunctional particle-analyte complexes. These constituents could interfere with detection or cause false detection outcomes and are flow past the biosensor working electrodes to a waste reservoir or wick.

The device further includes an electrochemical detection unit 240 comprising the biosensor with one or more working electrodes and an electrochemical detection system that produces electrochemical signals on each working electrode in proportion to the level of the analyte or group of analytes contained in signal amplification sandwich structures bound on or near the biosensor working electrode.

The electrochemical detection unit further provides at least one counter electrode and one reference electrode which are used to facilitate electrochemical detection as is known to those skilled in the art. The electrochemical detection unit also provides electronic circuitry that electrically connects each working electrode, counter electrode, and reference electrode to corresponding connection pads.

The connection pads are needed to electrically attach the electrochemical detection unit and/or biosensor to a potentiostat or other instrument that can generate an electrical source such as potential to the electrochemical detection unit and measure the resulting electrical signal, such as current, that is provided if guanine or other redox materials on the electrochemically detectable tags oxidize. The potentiostat can be part of the measurement instrument or used as a standalone instrument and is connected to other apparatuses that may be needed to support the electrochemical detection unit as will be described below. Other electrochemical techniques and configurations can be supported as would be obvious to those skilled in the art. The electrochemical detection unit may also provide a reservoir containing an electron transport mediator or other reagents that may be used by the detection method in some embodiments.

Another unique aspect of this invention is the ability to support different types of biosensor working electrodes. In one embodiment, the working electrode is a solid material such as carbon which is commonly used in a low-cost disposable test strip. The benefit of this biosensor working electrode is its low cost and low detection limit when the multifunctional particles provide a sufficient amplification ratio electrochemically detectable oligonucleotide tags. In another embodiment the biosensor working electrode is a nanobiosensor with nanoscale features. Nanobiosensor working electrodes can be employed when an improved detection level is desirable, at a higher cost per biosensor. Other types of biosensors can also be supported.

Figure 12B:
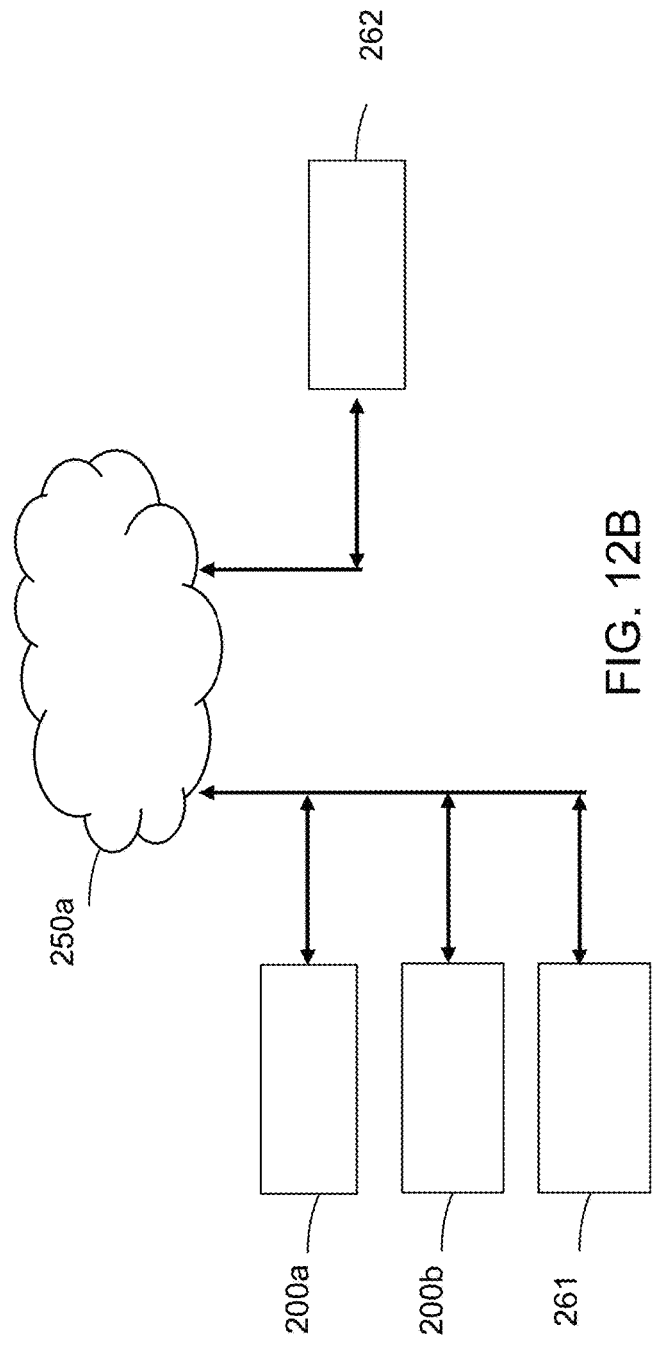

The device next includes an artificial intelligence unit 250 that interprets detection signals along with other input parameters to diagnose a disease, outbreak or condition. The artificial intelligence unit comprises one or more of central processing units, memories, concentration formulas, deterministic rules, algorithms, mathematical models, processes, decisions, inference engines, Boolean rules question and answer system, output recommendations, databases, user interfaces, communications interfaces, communications modules, device interfaces, device modules, image recognition interfaces image recognition modules. instrument interfaces, instrument modules, sensor interfaces, sensors, voice interface, voice module, software and devices to operate the interfaces and modules, other capabilities that would facilitate artificial intelligence processing and combinations thereof. Referring to FIG. 12A, in one embodiment, the artificial intelligence unit 250 is configured to operate as a unit within the device 250, Referring to FIG. 12B, in another embodiment, the artificial intelligence unit 250a is configured to operate as a unit within a cloud server or another device and communicate with the amplification, detection and quantification device 200a, with other assays 200b and with other smart phones, computers, instruments, devices and databases 261. In both embodiments, the artificial intelligence recommendations can be transmitted to other smart phones, computers, instruments, devices and databases 262.

Device Configurations

The above invention can also take the form of device configurations that provide beneficial aspects for particular applications. In some embodiments the fluid samples are processed in test cartridges or panels that are single use or multiple use, and are operated by instruments containing electrical, mechanical and other systems required to process fluid samples in the test cartridges. Embodiments are described below which illustrate a partial list of possible device configurations.

Figure 13A:
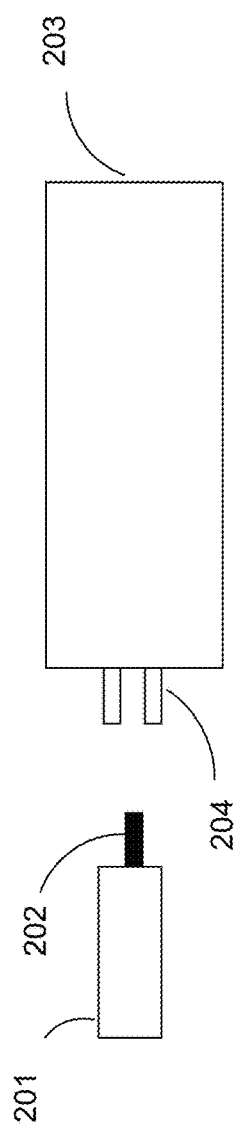
FIGS. 13A and 13B are schematic representations of an amplification, detection and/or quantification device according to embodiments of the present invention.
Figure 13B:
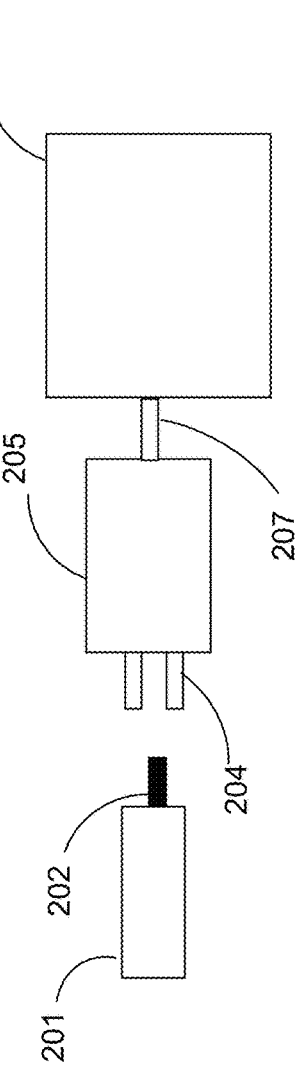

Referring to FIG. 13A, in one embodiment the device units are configured to comprise a test cartridge 201 comprising portions of the device units for processing the fluid sample; and an instrument 203 comprising portions of the device units for operating one or more test cartridges to process the fluid sample. The test cartridge interface 202 on the test cartridge 201 allows the test cartridge to connect to the instrument interface 204 on the instrument 202. This embodiment can be used as a handheld device, point-of-care device, point-of-use device, lateral flow device, laboratory device, in vitro device, portable device, Referring to FIG. 13B, in another embodiment the device units are configured to comprise a test cartridge 201 comprising portions of the device units for processing the fluid sample; a plug-in instrument 205 comprising portions of the device units for operating one or more test cartridges to process the fluid sample; and a standalone instrument 206 that provides additional capabilities which are not available on the plug-in instrument. The test cartridge interface 202 on the test cartridge 201 allows the test cartridge to connect to the plug-in instrument interface 204a on the plug-in instrument 205. The plug-in instrument 205 has a second interface 207 to connect to the standalone instrument, which could be a physical connection or a wireless connection. The plug-in instrument can be a computer plug-in, adapter, printed circuit board, semiconductor, wearable device, embedded device, and the standalone instrument can be a smart phone, computer, tablet, medical device, communications device, testing device, or other device containing additional functionality that the plug-in instrument does not provide.

Figure 13C:
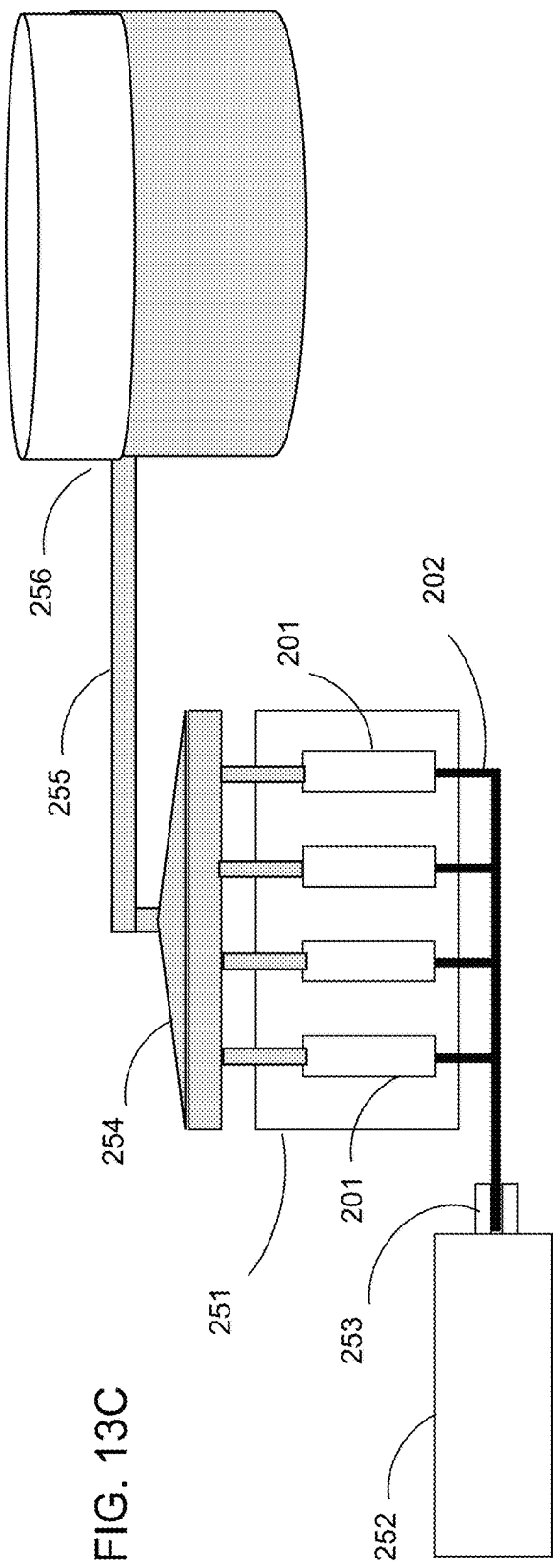
FIG. 13C is a schematic representation of an amplification, detection and/or quantification device and test cartridges contained in a panel with a manifold and other instruments according to one embodiment of the present invention.

Referring to FIG. 13C, in another embodiment the device units are configured to comprise one or more test cartridges 201 contained in a panel 251, wherein the test cartridge comprises portions of the device units for processing the fluid samples; and an instrument 252 comprising portions of the device units for operating one or more test cartridges in the panel to process one or more fluid samples. An interface 202b on test cartridges 201 allows the test cartridges to connect to the instrument interface 253 on the instrument 252. In another embodiment, the panel 251 is also connected to a manifold 254 that delivers one or more fluid samples to the one or more test cartridges contained in the panel. In another embodiment, the manifold 254 is also connected to a delivery system 255 that delivers one or more fluid samples to the manifold for testing in the one or more test cartridges. In another embodiment the delivery system is connected to a sample source 256 that contains one or more samples. The sample source can be a tank, a concentrator, an environmental source, an industrial source, a water source, a medical source, a system to liquefy solid samples, a system to liquefy gas samples. The instrument 252 may have additional capabilities to operate, house and/or coordinate the functions of the one or more ancillary instruments, devices and interfaces required to extract samples, process samples, concentrate samples, measure analytes, transmit test results and deliver secondary materials or perform additional functions required for the multifunctional particles results. This embodiment can be used as an inline meter, field analyzer, networked sensing node.

Instrument

The device is further described by an instrument that provides capabilities to allow the device to collect the fluid sample, form a first outer layer and inner layer of signal amplification sandwich structures, form a second outer layer of signal amplification sandwich structures, and measure detection signals from the electrochemically detectable oligonucleotide tags conjugated on said signal amplification sandwich structures, The instrument provides an electronic capability to generate an electrochemical technique such as square wave voltammetry and subsequently measure the corresponding signal generated from the electrochemically detectable oligonucleotide tags and the electrochemical biosensor. The electronic capability can be a potentiostat instrument, a potentiostat printed circuit board, a potentiostat chip, or electronics that provide the capability to generate an electrochemical technique and subsequently measure the corresponding signal generated from the electrochemically detectable oligonucleotide tags and the electrochemical biosensor.

The instrument further provides other capabilities to perform the test in the test cartridge and communicate the test results. Other capabilities and systems that can be provided in the instrument include one or more of a user interface, display, multiplexer to interface with multiple biosensor working electrodes, processor, memory, communications, pump and compressor to operate the test cartridge.

The instrument can further provide additional capabilities to support the collection of samples, support the functionality of the multifunctional particles, and interface with other devices. Other capabilities and systems that can be provided in the instrument include one or more of physical separation, filtering, concentrating, magnetic separation, optical reading, storing and delivering chemicals and reagents, lysing, heating, cooling, releasing and delivering materials from the inner structure of multifunctional particles.

In some embodiments the instrument will be used to operate the test sample with other devices. In some embodiments the other devices can be standalone instruments that provide one or more of the capabilities required to operate the test and as a consequence are not required to be provided by the instrument described above. In these embodiments, a plug-in instrument can offer a subset of the capabilities not provided by the standalone instrument in order to reduce instrument cost, provide portability and flexibility for the specific application.

Test Cartridge

Figure 14:
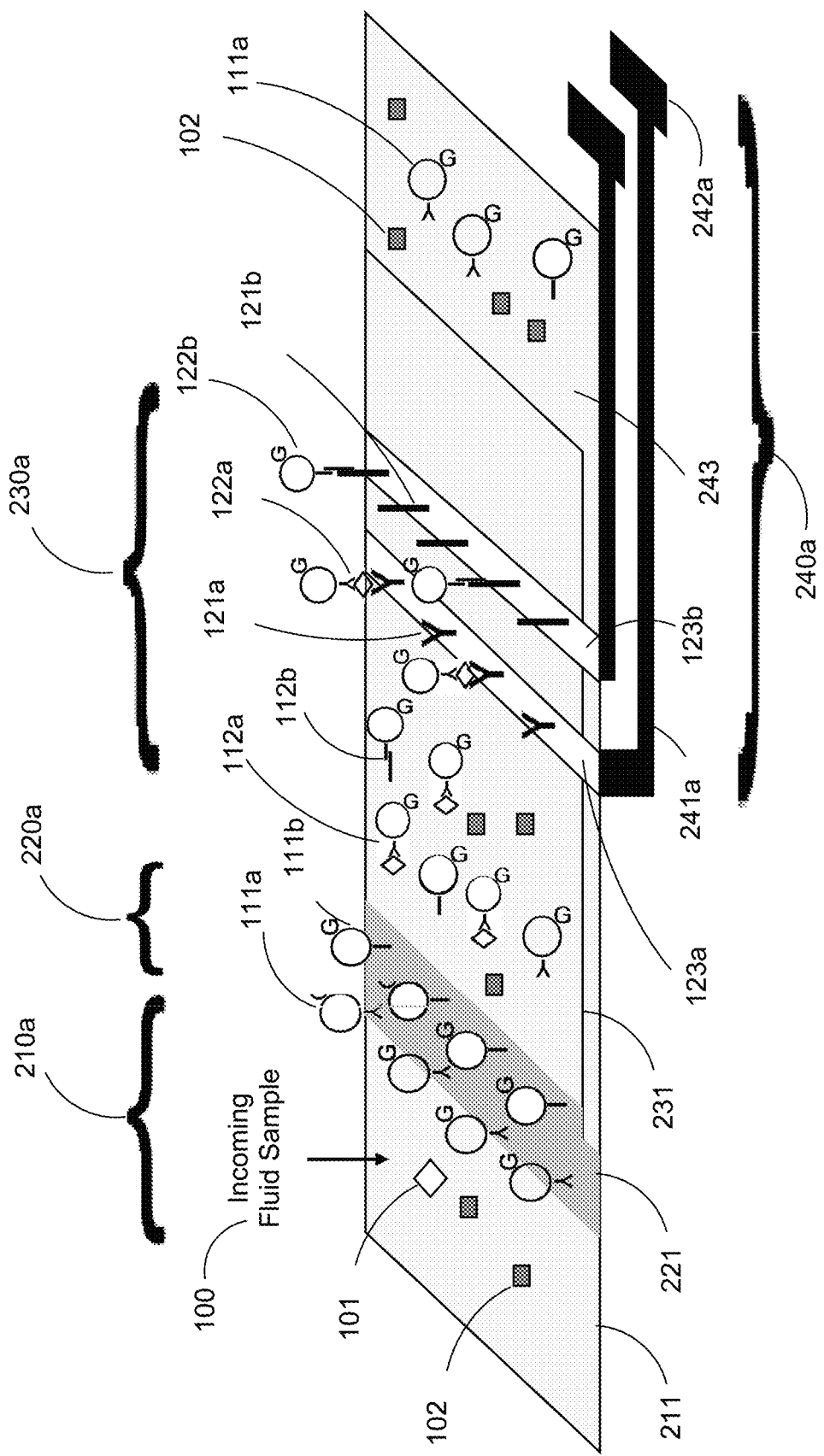
FIGS. 14, 15, 16, and 17 are schematic representations of test cartridges according to embodiments of the present invention.

The device is further described by a test cartridge used to process fluid samples that contain one or more analytes. The test cartridge is selected from the group consisting of one or more of a biosensor cartridge, microfluidics, lateral flow test strip, lateral flow device cartridge, embedded cartridge, wearable cartridge, patch, microarray, smart material, and smart package. Referring to FIG. 14, in one embodiment the test cartridge is a lateral flow device cartridge comprises a) a sample collection unit 210a configured to collect said fluid sample with a sample pad or reservoir, b) a signal amplification tag attachment unit 220a configured to form a first outer layer and inner layer of signal amplification sandwich structures with a conjugation pad or reservoir, c) a signal amplification tag capture unit 230a configured to form a second outer layer of signal amplification sandwich structures with a membrane or reservoir, and d) an electrochemical detection unit 240a with at least one biosensor working electrode configured to measure detection signals from the electrochemically detectable oligonucleotide tags contained on said signal amplification sandwich structures. Excess fluid is removed with a wick pad or reservoir. The test cartridge also contains a backing or structure and a cartridge housing.

The sample collection unit 210a receives a fluid sample 100 that can contain analytes 101 and nonspecific materials 102. The lateral flow of the fluid directs the fluid sample 100, analytes 101, and nonspecific materials 102 to the signal amplification tag attachment unit 220a, where multifunctional particle conjugates 111 are provided to bind with analytes and form multifunctional particle-analyte complexes 112. The multifunctional particle-analyte complexes are provided to the signal amplification tag capture unit 230a where analytes in the multifunctional particle-analyte complexes bind with the analyte binding materials on or near the working electrode 123a to form signal amplification sandwich structures 122a. In some configurations there are other biosensor working electrodes 122b which can be used to detect other analytes. A biosensor working electrode can also be used as a negative control to determine a baseline signal where there are no analytes, or as one or more positive controls to determine a baseline signal from a known analyte concentration. The electrochemical detection unit 240*a* also provides a counter electrode and a reference electrode (not shown) to conduct the electrochemical detection technique. Electrode circuits 242*a*, and connectors 242*a* . . . to the measuring instrument are also provided.

Figure 18:
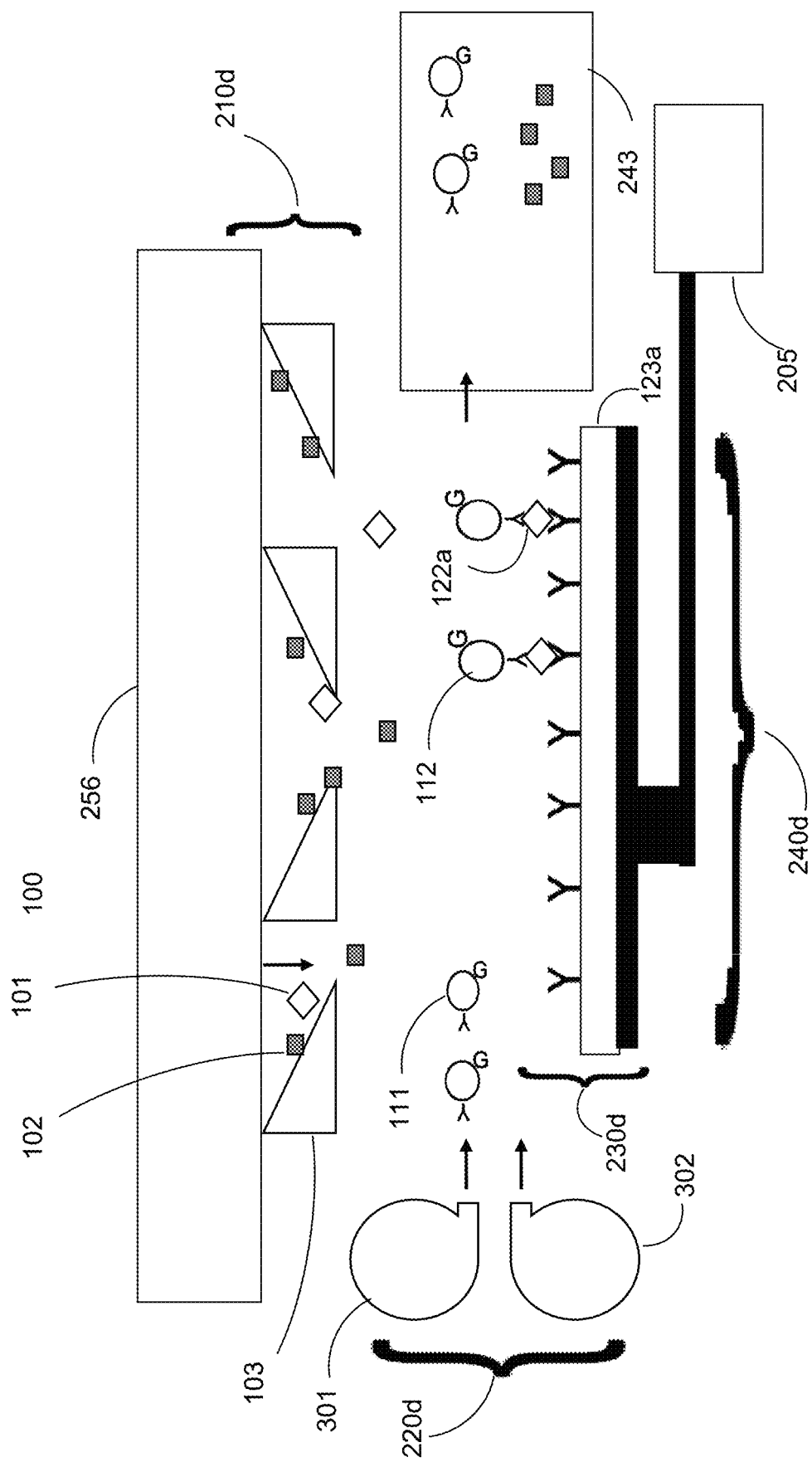
FIG. 18 is a schematic representation of a microfluidics test cartridge according to one embodiment of the present invention.

Referring to FIG. 18, in another embodiment the test cartridge is a microfluidics device cartridge comprises a) a sample collection unit 210*d* configured to collect said fluid sample, b) a signal amplification tag attachment unit 220*d* configured to form a first outer layer and inner layer of signal amplification sandwich structures, c) a signal amplification tag capture unit 230*d* configured to form a second outer layer of signal amplification sandwich structures, and d) an electrochemical detection unit 240*d* with at least one biosensor working electrode configured to measure detection signals from the electrochemically detectable oligonucleotide tags conjugated on said signal amplification sandwich structures.

The sample collection unit 210*d* is in contact with a sample source 256 which provides a fluid sample 100, analytes 101, and nonspecific materials 102. The sample source could be a person, an animal, a food product, a package surface, etc. A delivery mechanism 103 directs the fluid sample 100, analytes 101, and nonspecific materials 102 to the signal amplification tag attachment unit 220*d*, where a reservoir or sprayer 301 with multifunctional particle conjugates 111 are provided to bind with analytes and form multifunctional particle-analyte complexes 112. The multifunctional particle-analyte complexes are provided to the signal amplification tag capture unit 230*d* where analytes in the multifunctional particle-analyte complexes bind with the analyte binding materials on or near the working electrode 123*a* to form signal amplification sandwich structures 122*a*. In some configurations there are other working electrodes 122*b* which can be used to detect other analytes. A working electrode can also be used as a negative control to determine a baseline signal where there are no analytes, or as one or more positive controls to determine a baseline signal from a known analyte concentration. The electrochemical detection unit 240*a* also provides a counter electrode and reference electrode (not shown) to conduct the electrochemical technique. Electrode circuits 242*a*, and connectors 242*a* . . . to the measuring instrument are also provided. Other types of test cartridges can be used that are not described here. A unique aspect of the invention is that the test cartridge and multifunctional particles can be configured to support many diverse applications including complex samples media, ultra-low limits of detection, portability, field use, high throughput, etc.

Additional Features and Configurations

The above invention provides additional features and configurations of the method and device for amplifying, detecting, and/or quantifying an analyte or multiple different analytes in a fluid sample that provide beneficial aspects for particular applications. The following descriptions are made using lateral flow device cartridges, however the configurations can readily apply to other types of test cartridges. As well, many of the features described as embodiments can also be used as a combined embodiment.

Multiplexing

The method and device can be used to amplify, detect and/or quantify multiple analytes simultaneously from the same fluid sample in a multiplex assay. Referring to FIG. 14, there are two biosensor working electrodes in the signal amplification tag capture unit 230*a*. In another embodiment there can be three or more biosensor working electrodes, along with one or more counter electrodes and a reference electrode. In one embodiment, multiple different analytes are measured simultaneously from the fluid sample individually at unique biosensor working electrodes associated with each different analyte. Referring to FIG. 4, each biosensor working electrode has a plurality of a single set of an analyte binding material for capturing individual analytes, and subsequently amplifying, detecting and/or quantifying individual analytes on individual biosensor working electrodes. For example, biosensor working electrode 122*a* is conjugated with analyte binding material 118*a* for binding analyte A 101*a*, biosensor working electrode 122*b* is conjugated with analyte binding material 118*b* for binding with analyte B 101*b*, and biosensor working electrode 122*c* is conjugated with analyte binding material 118*c* for binding with analyte C 101*c*.

Referring to FIG. 6, in another embodiment, each biosensor working electrode has a plurality of a single set of analyte binding material for capturing individual analytes, and is also conjugated with a plurality of an oligonucleotide recognition probe that is complementary to the electrochemically detectable oligonucleotide tag used for amplifying, detecting and/or quantifying individual analytes on individual biosensor working electrodes. For example, biosensor working electrode 122*a* is conjugated with analyte binding material 118*a* for binding analyte A 101*a*, and is also conjugated with oligonucleotide recognition probe C1 124*a* for hybridizing with electrochemically detectable oligonucleotide tags G1 113*a*. In one embodiment the electrochemically detectable oligonucleotide tag G1 is eluted using elution methods commonly known to one skilled in the art such as an elution agent formamide/with sodium acetate and heated for 10 minutes at 90° C. The eluted tags G1 are delivered to oligonucleotide recognition probe C1 124*a* and hybridize to form duplexes C1-G1 125*a* at the surface of the biosensor working electrode 121*a*. In another embodiment the electrochemically detectable oligonucleotide tags G1 113*a* are adsorbed to the surface of the biosensor working electrode 121*a* with no oligonucleotide recognition probes C1.

In another embodiment, multiple different analytes are measured simultaneously from the fluid sample as a group individually at a common biosensor working electrode associated with each different analyte. Referring to FIG. 5, each biosensor working electrode has a plurality of multiple sets of analyte binding materials for capturing multiple analytes in a group, and subsequently amplifying, detecting and/or quantifying any analytes in a group on a common biosensor working electrode. For example, biosensor working electrode 122*d* is conjugated with analyte binding material 118*a* for binding analyte A, analyte binding material 118*b* for binding analyte B 101*b*, and analyte binding material 118*c* for binding analyte C 101*c*.

Referring to FIG. 6, in another embodiment each biosensor working electrode has a plurality of a single set of oligonucleotide recognition probes for hybridizing with electrochemically detectable oligonucleotide tags, and subsequently amplifying, detecting and/or quantifying individual analytes on individual biosensor working electrodes. In another embodiment, each biosensor working electrode has a plurality of multiple sets of oligonucleotide recognition probes for hybridizing with electrochemically detectable oligonucleotide tags or no oligonucleotide recognition probes for hybridizing or adsorbing multiple analytes in a group, and subsequently amplifying, detecting and/or quantifying any analytes in a group on a common biosensor working electrode.

Diverse Sample Volumes

The method and device can be used to amplify, detect and/or quantify an analyte or a group of multiple different analytes using a wide range of sample volumes. This includes very small samples which tend to use less reagents in assays. The range also extends to very large samples in order to provide a better representation of the source being tested and also provide a greater quantify of analytes to permit lower levels of detection and less variability in quantification at low analyte levels.

Referring to FIG. 14, there is a sample collection unit 210a for receiving the incoming fluid sample 100. In one embodiment the sample collection unit receives a few drops of incoming fluid sample with a volume of between 5 µL to 120 µL as provided to a typical lateral flow test cartridge, such as a pregnancy test or blood glucose test.

Figure 16:
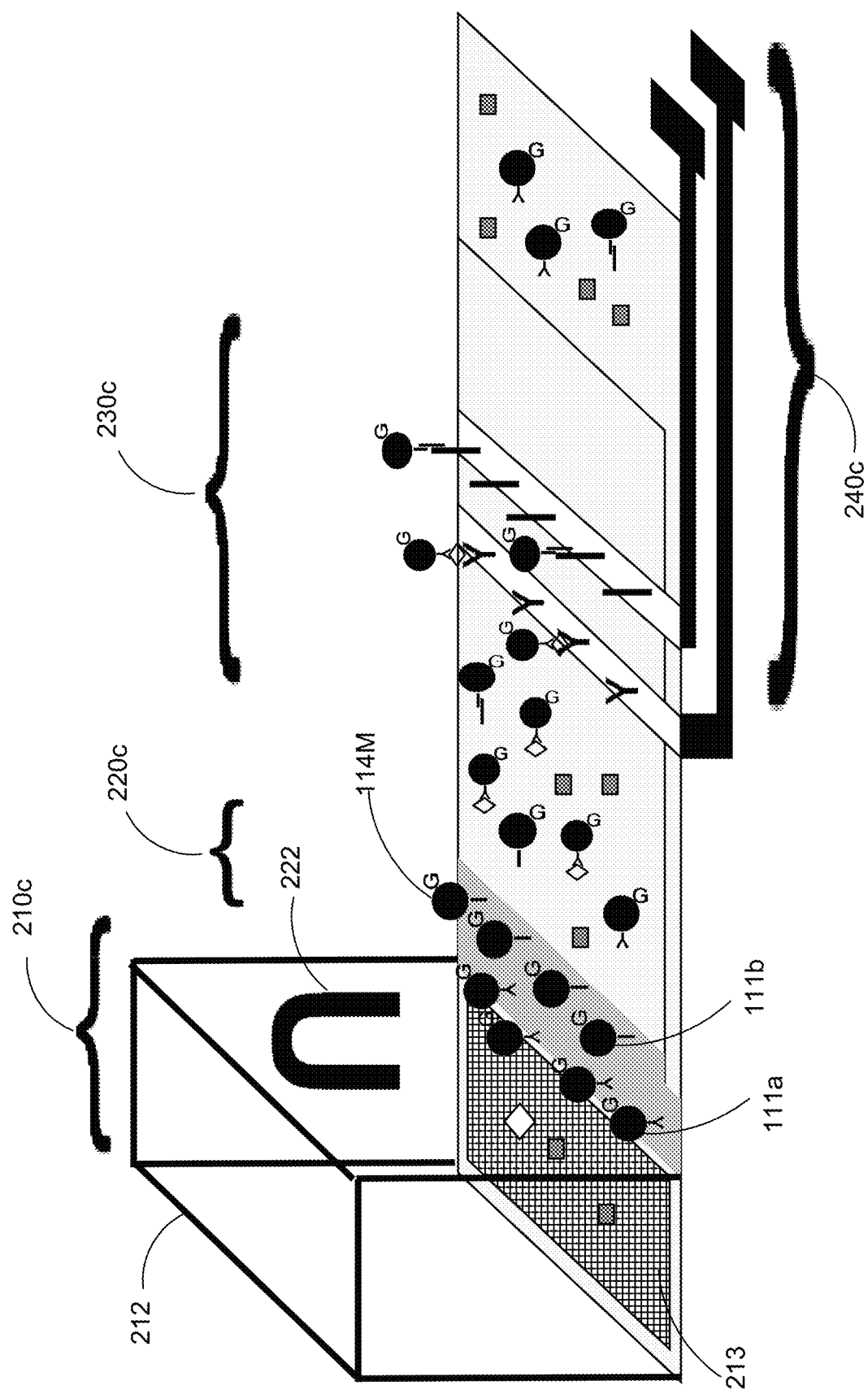

The sample collection unit can also accommodate a wide range of sample volumes. Referring to FIG. 16, in another embodiment, the sample collection unit 210c contains a reservoir 212 which allows a larger fluid sample volume to be provided for improved detection performance. For example, an incoming fluid sample of 100 mL volume can be used with 1000 times the quantity of analytes as a typical lateral flow test cartridge fluid sample. This is particularly useful when detecting low dose pathogens and cancer biomarkers that are not able to be measured because the small volume samples lack a detectable quantity of analytes.

In another embodiment, the sample collection unit 210c also contains a filter 213 to concentrate the sample and increase the concentration of analytes by filtering out fluid that does not contain the analytes. The filter is selected with adequate pore size that allows a portion of the liquid sample to pass through the filter and leave behind the analytes 101 which are too large to pass through the filter pores. In addition to retaining the analytes for detection, certain nonspecific materials that are smaller than the pores will exit the sample collection unit and not be passed to the signal amplification tag attachment unit 220c.

When complex sample media are used, such as food or blood, samples can be pre-processed in the sample collection unit using one or more of a pre-filtration mesh to remove very large non-specific materials, chemical and mechanical processes to break up clumps that may contain analytes, prevent analytes from sticking to the filter or sample collection unit, facilitate washing and the delivery of analytes in the sample to the multifunctional particles, or lysing the analytes to release nucleic acids or proteins. In another embodiment, the sample collection unit 210c also provides chemical and mechanical processes to break up clumps and/or remove analytes from the filter surface. An optional heater can also be provided.

In another embodiment the sample collection unit also provides one or more lysing reagents to lyse cells and other materials in order to release internal constituents and transcriptions such as target nucleic acids and proteins for delivery to the signal amplification tag attachment unit and subsequently for detection. An optional heater can also be provided. In another embodiment, the sample collection unit also provides one or more antibiotics in order to produce antimicrobial susceptibility analytes such as proteins, biomarkers, endotoxins, and target nucleic acids that can be used to determine antimicrobial susceptibility. An optional heater can also be provided.

In another embodiment, the sample collection divides the incoming fluid sample into two portions and delivers one portion to a first signal amplification tag attachment unit and subsequently to the first signal amplification tag attachment unit. The second potion is provided nutrients and heat for a sufficient time to permit viable organisms to reproduce. The treated second portion is subsequently delivered to a second signal amplification tag attachment unit and subsequently a second signal amplification tag attachment unit, The signals from the two portions are compared on a concentration curve to determine if the analytes in the second portion have significantly increased due to the presence of viable organisms.

Magnetic Separation

Figure 15:
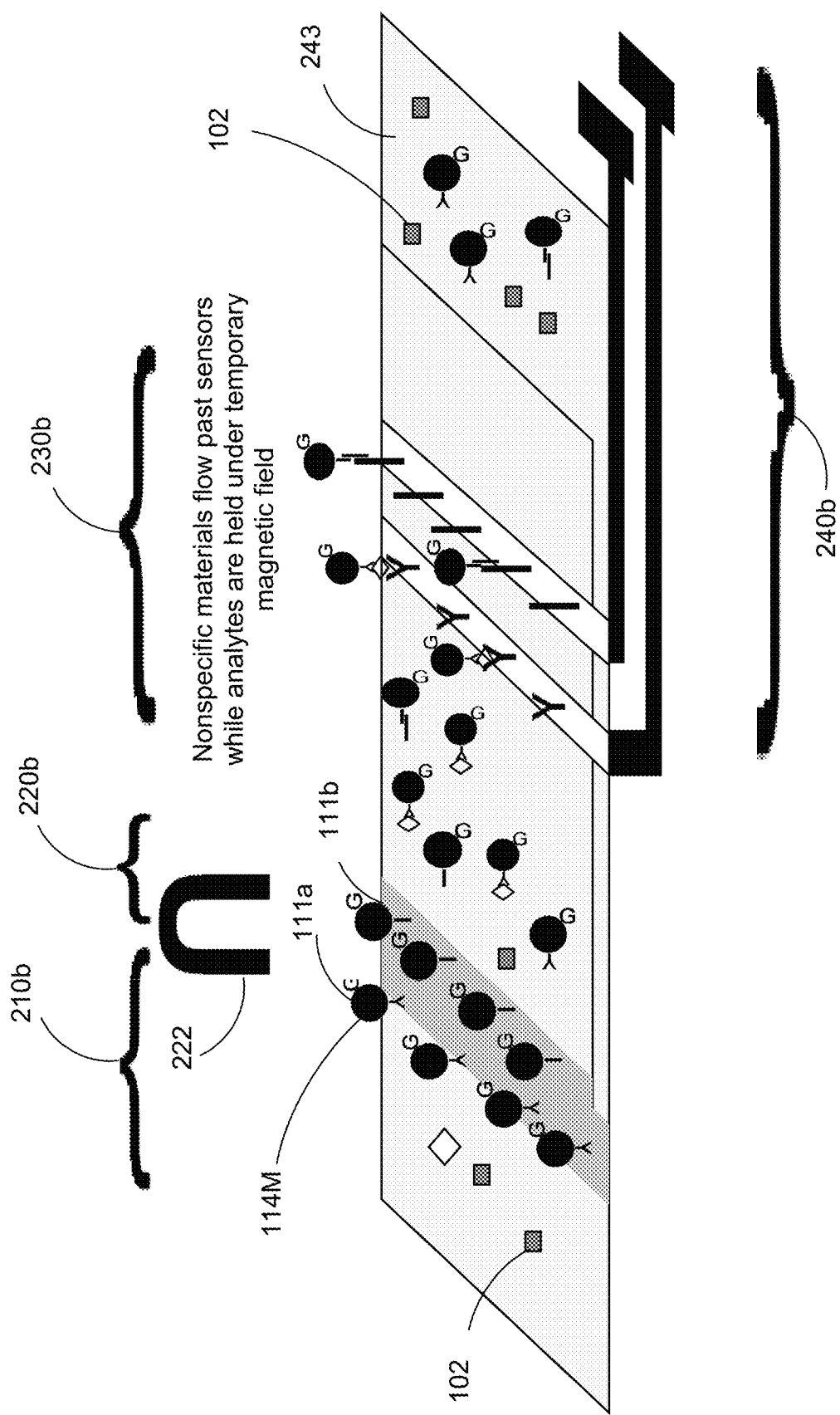

The method and device can be used to amplify, detect and/or quantify an analyte or a group of multiple different analytes using magnetic separation to separate analytes from nonspecific materials to remove the incidence of false detection outcomes. Referring to FIG. 15, there are multifunctional particles 114M filled in their inner structures with a magnetic material. The magnetic inner structure allows the multifunctional particles to also act as magnetic particles that are used to magnetically separate analytes in the fluid sample from nonspecific materials. In this embodiment, one or more sets of multifunctional particles 111a, 111b, . . . are contained in the signal amplification tag attachment unit 220b. The analytes bind with multifunctional particle conjugates in the signal amplification tag attachment unit 220b to form a first outer layer and inner layer of signal amplification sandwich structures. A magnetic field 222 is used to temporarily immobilize the multifunctional particles 114M bound with the analytes 101 and allow the fluid sample 100 and nonspecific materials 102 to flow past the biosensor in the signal amplification tag capture unit 230b to a waste reservoir or wick 243. The magnetic field is subsequently removed and multifunctional particles 114M bound with the analytes 101 are no longer immobilized and flow to the biosensor in the signal amplification tag capture unit 230b to form signal amplification sandwiches.

Referring to FIG. 16, in another embodiment the sample collection unit 210c contains a filter 213 that allows a portion of the liquid sample to pass through the filter leaving behind the analytes 101 which are too large to pass through the filter pores. The sample collection unit also contains multifunctional particles 114M filled in their inner structures with a magnetic material. In this embodiment, one or more sets of multifunctional particles 111a, 111b, . . . are contained in the sample collection unit 210c. The analytes bind with multifunctional particle conjugates in the sample collection unit 210c to form a first outer layer and inner layer of signal amplification sandwich structures. A magnetic field 222 is used to temporarily immobilize the multifunctional particles 114M bound with the analytes 101 and allow the fluid sample 100 and nonspecific materials 102 to flow past the biosensor in the signal amplification tag capture unit 230b to a waste reservoir or wick 243. The magnetic field is subsequently removed and multifunctional particles 114M bound with the analytes 101 are no longer immobilized and flow to the biosensor in the signal amplification tag capture unit 230b to form signal amplification sandwiches. In another embodiment the multifunctional particles 114M and magnetic separation is used to lyse cells as described above. In another embodiment the multifunctional particles 114M and magnetic separation is used for antimicrobial susceptibility testing as described above. In another embodiment the multifunctional particles 114M and magnetic separation is used for viability testing as described above.

Additional Functionality

The method and device can be used to amplify, detect and/or quantify an analyte or a group of multiple different analytes using a wide range of materials in the inner structure of the multifunctional particles to provide additional functional to the assays. These materials are selected from the group consisting of structural materials, magnetic materials, optical materials, nuclear materials, radiological materials, quantum materials, biological materials, energetic materials, electrochemical materials, chemical materials, pharmaceutical materials, antibiotic materials, chemotherapy materials, antibodies, and combinations thereof.

In one embodiment, there are multifunctional particles filled in their inner structures with a material such as an optical material, quantum material or other material that can be used as a bar code to identify the particle. In another embodiment, there are multifunctional particles filled in their inner structures with a material such as an electrochemical material that can be used to increase the amplification capability of the electrochemically detectable tags bound to the outer structure.

In another embodiment, there are multifunctional particles filled in their inner structures with a material that is released after detection. This can be used to kill a pathogen analyte, to neutralize a chemical analyte, or interact with the analyte in the assay or in the source. In these embodiments a release mechanism to release the analytes are provided in the device instrument or cartridge.

Easy to Use

Figure 17:
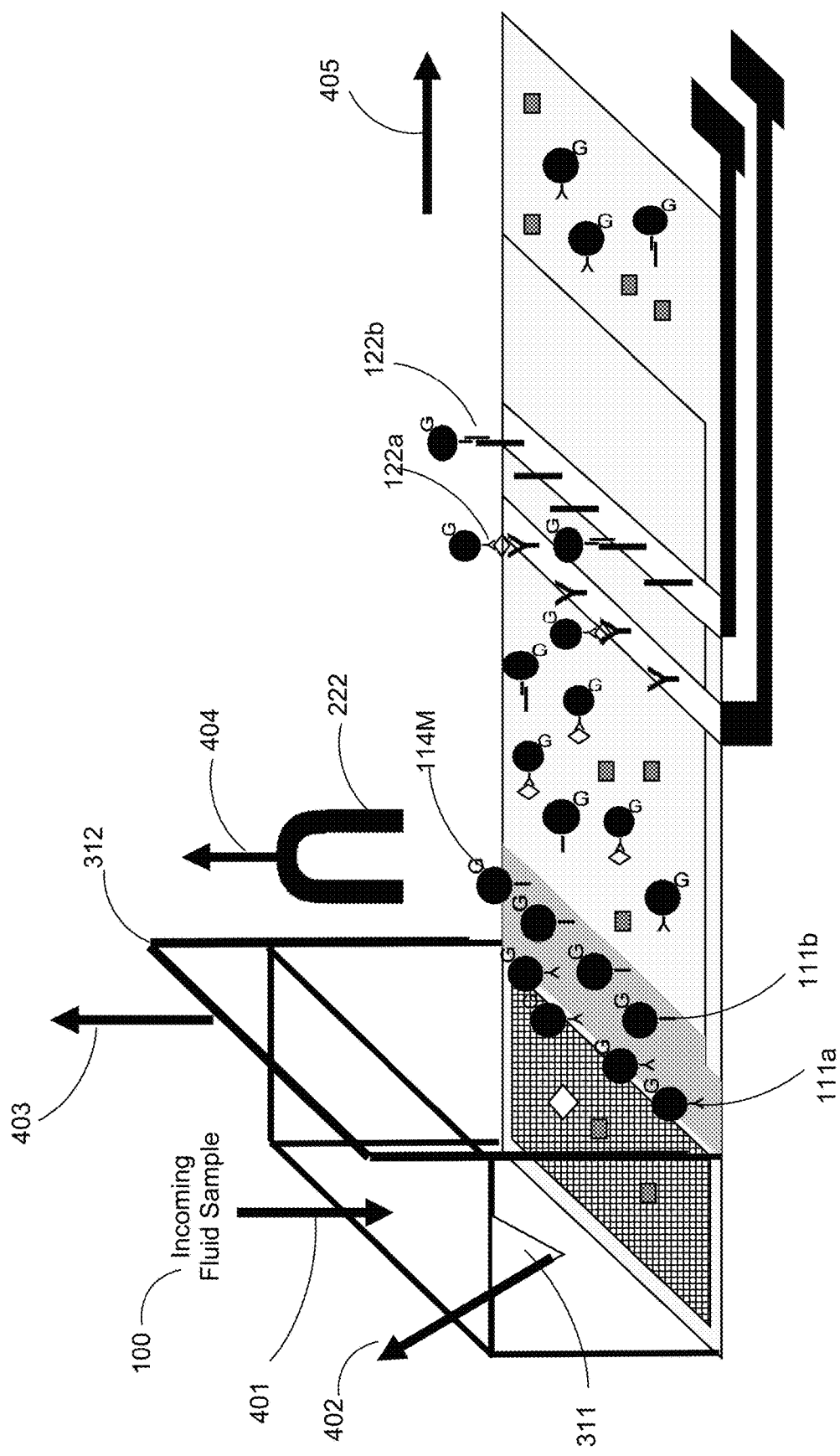

The method and device can be used to amplify, detect and/or quantify an analyte or a group of multiple different analytes with an easy to use method and device. Referring to FIG. 17, in one embodiment, a user inserts a fluid sample 100 into a test cartridge opening 401. The user next pulls tab 402 that releases lysis reagents to the fluid sample from a lysis reservoir 311. This allows the lysis reagents to lyse bacteria and release protein and nucleic acid targets. The cartridge can be shaken to assist the reaction. The user next pulls tab 403 that allows the protein and nucleic acid targets to laterally flow to the conjugates 111a and 111b which comprise magnetic particles 114M and form multifunctional particle-analyte complexes. The magnetic field 222 temporarily attracts the multifunctional particle-analyte complexes and allows nonspecific materials to flow past the biosensor working electrodes. The user next pulls tab 404 to remove the magnetic field and allow the multifunctional particle-analyte complexes to laterally flow to the biosensor working electrodes and form signal amplification sandwich structures 122a and 122b. The user next inserts the cartridge 405 into a test instrument where an electrochemical signal generator generates electrochemical signals and converts signals into the concentration of each analyte using a pre-programmed formula.

EXAMPLES

In order that this invention may be better understood, the following examples are set forth. These examples are provided solely for the purpose of further illustrating certain specific aspects and embodiments of the invention. Although embodiments of the invention have been disclosed for illustrative purposes, those skilled in the art will appreciate that various modifications, additions and substitutions are possible, including multiple target types without departing from the scope and spirit of the invention as herein described, and all are included within the scope of the invention.

Example 1—Present/Absent Immunoassay. The platform was configured as an immunoassay to detect the presence of specific analytes through their properties as antigens or antibodies. Although the following immunoassay example illustrates *E. coli* O157:H7, other protein analytes can also be used. A test cartridge was prepared with conjugates comprising 1-micron polystyrene beads as the multifunctional particle conjugated with approximately 10% anti-*E. coli* O157:H7 polyclonal antibodies and 90% 20-mer guanine quadruplex oligonucleotides. The antibodies and oligonucleotides were biotinylated and conjugated to streptavidin coated polystyrene beads. A biosensor working electrode was conjugated with anti-*E. coli* O157:H7 monoclonal antibodies. A second biosensor working electrode was provided as a negative control. A 0.5 mL fluid sample was placed in the test cartridge sample collection unit and laterally flowed to the signal amplification tag attachment unit containing the conjugates. *E. coli* O157:H7 analytes in the fluid sample had bound with the conjugates to form multifunctional particle-*E. coli* complexes. The fluid sample, multifunctional particle-*E. coli* complexes, unbound conjugates, and nonspecific materials in the fluid sample laterally flowed to the signal amplification tag capture unit where the multifunctional particle-*E. coli* complexes bound to the anti-*E. coli* O157:H7 monoclonal antibodies on the biosensor working electrode to form signal amplification sandwich structures. The electrochemical detection unit employed a potentiostat to generate a square wave voltammetry scan with a 1400 mV/s scan rate on each biosensor working electrode. *E. coli* was deemed to be present when the peak signal on the *E. coli* working electrode exceeded the peak signal on the negative control electrode by a significant amount predetermined by industry norms. In this example, the negative control was scanned 3 times and the and negative control cut-off signal was determined as the mean of the three scans plus 3 standard deviations of the variance. Typical detection limits were 50 cfu/mL using 1 micron multifunctional particles with 20-mer quadruplex oligonucleotide tags and 0.5 mL sample volumes. Options for reducing the detection limit include bigger particles, longer oligonucleotide tags and larger sample volumes.

Example 2—Quantitative Immunoassay. The Present/Absent Immunoassay described in Example 2 was further evaluated to obtain a quantitative value associated with the *E. coli* O157:H7 fluid sample. The peak signal on the *E. coli* working electrode was entered into a mathematical formula derived from pre-determined standards of peak signals from known *E. coli* O157:H7 concentrations. The peak signal generated from *E. coli* O157:H7 in the sample was used in the formula to convert the peak signal to a estimated *E. coli* O157:H7 concentration.

Example 3—Multiplexed Quantitative Immunoassay. The Quantitative Immunoassay described in Example 2 was further evaluated by quantifying two different analytes in the same assay, *E. coli* O157:H7 and *Listeria monocytogenes*. In addition to the *E. coli* conjugates described above, a second set of analyte conjugates was added comprising 1-micron polystyrene beads as the multifunctional particle conjugated with approximately 90% 20-mer guanine quadruplex oligonucleotides and 10% anti-*Listeria monocytogenes* polyclonal antibodies that bind *Listeria monocytogenes* to create multifunctional particle-*Listeria monocytogenes* complexes. An additional biosensor working electrode was also added that was conjugated with anti-*Listeria monocytogenes* monoclonal antibodies to create signal amplification sandwich structures on the *Listeria* working electrode if the *Listeria monocytogenes* were present in the sample.

Example 4—Multiplexed Quantitative Immunoassay for Group of Analytes. The Quantitative Immunoassay described in Example 3 was further evaluated by quantifying any two different analytes in a group in the same assay, *E.*

*coli* O157:H7 and *Listeria monocytogenes*. In addition to the *E. coli* conjugates described above, a second analyte conjugate was added that contained anti-*Listeria monocytogenes* polyclonal antibodies that bind *Listeria monocytogenes* to create multifunctional particle-*Listeria monocytogenes* complexes. The initial additional biosensor working electrode was conjugated with both anti-*E. coli* O157:H7 monoclonal antibodies and anti-*Listeria monocytogenes* monoclonal antibodies to create signal amplification sandwich structures if either the *E. coli* O157:H7 or *Listeria monocytogenes* were in the sample.

Example 5—Quantitative Immunoassay in Complex Media. The Quantitative Immunoassay described in Example 2 was further evaluated by changing the conjugate's multifunctional particle from 1-micron polystyrene particles to 1-micron magnetic particles, such as iron oxide, with a polystyrene coating. The polystyrene surface was further coated with streptavidin to enable conjugation with biotinylated antibodies and oligonucleotides. The sample was added to the sample collection unit and mixed with the conjugates to form multifunctional particle-*E. coli* complexes. A magnetic field was applied for a predetermined time ranging from 1 to 20 minutes in the signal amplification tag attachment unit to allow nonspecific materials to laterally flow past the biosensor working electrodes before the magnetic field was removed to release the multifunctional particle-*E. coli* complexes.

Example 6—Concentrated Quantitative Immunoassay in Complex Media. The Quantitative Immunoassay in Complex Media described in Example 5 was further evaluated by adding a filter and reservoir to the sample collection unit to allow the fluid sample to be concentrated before being delivered to the signal amplification tag attachment unit. The fluid sample was increased from 0.5 mL to 100 mL. A tab was placed between the sample collection unit and the signal amplification tag attachment unit to allow necessary time for the sample to concentrate through the filter. A spring mechanism was used to force the liquid sample through the filter. After a few minutes the tab was released to allow the retentate to flow from the sample collection unit to the signal amplification tag attachment unit to continue the assay.

Example 7—Quantitative Hybridization Assay from Lysed Bacteria. The Concentrated Quantitative Immunoassay in Complex Media described in Example 6 was further evaluated by changing the conjugate's anti-*E. coli* O157:H7 polyclonal antibodies to oligonucleotide probes that hybridize one end of an *E. coli* 16S rRNA target to create multifunctional particle-*E. coli* O157:H7 16S rRNA complexes. A biosensor working electrode was conjugated with a second set of oligonucleotide probes that that hybridize with the opposite end of an *E. coli* 16S RNA target. The sample collection unit was modified to add a lysis reservoir for delivering lysis reagents and a tab for releasing the lysis reagents to the sample collection unit. The assay begins by providing a sample to the sample collection unit and in some embodiments concentrating the sample as described in example 4. After concentration a tab was released to allow the lysis reagents to flow from the lysis reservoir to the concentrate to lyse bacteria. Other processes such as shaking the cartridge may be beneficial. After a few minutes the second tab was released to allow the lysate to flow from the sample collection unit to the signal amplification tag attachment unit to continue the assay.

Example 8—Multiplex Quantitative Hybridization Assay from Lysed Bacteria. The Quantitative Hybridization Assay without PCR from Lysed Bacteria described in Example 7 was further evaluated by quantifying two different analytes in the same assay, a 16S rRNA and a mRNA. In addition to the *E. coli* 16S rRNA target described above, a second analyte conjugate was added that contained oligonucleotide probes that hybridize with one end of an *E. coli* O157:H7 mRNA target to create multifunctional particle-*E. coli* O157:H7 mRNA complexes. An additional biosensor working electrode was also added that was conjugated with a second set of oligonucleotide probes to hybridize with the opposite end of an *E. coli* O157:H7 mRNA target.

Example 9—Viability Assay. The Concentrated Quantitative Immunoassay in Complex Media described in Example 6 was further evaluated by metering a sample into two parts and delivering one part of the sample to a first cartridge to generate a peak signal then determine the associated *E. coli* O157:H7 concentration. The second part of the sample was provided to nutrients and heat to allow viable *E. coli* O157:H7 to reproduce for 2 to 6 reproduction cycles. The second part of the sample is then provided to a second cartridge to generate a peak signal and associated *E. coli* O157:H7 concentration. The *E. coli* O157:H7 is determined to be viable if the concentration from the second cartridge has been found to increase over the first cartridge by a statistically significant amount.

Example 10—Antimicrobial Susceptibility Test. The Concentrated Quantitative Immunoassay in Complex Media described in Example 6 was further evaluated for detecting Carbapenemase producing (CP)—Carbapenem-resistant Enterobacteriaceae (CRE). A test cartridge was prepared with conjugates comprising 1-micron magnetic particles with a polystyrene coating as the multifunctional particles which were further coated with streptavidin. The conjugates were conjugated with approximately 10% biotinylated anti-*Klebsiella pneumoniae* carbapenemases enzyme (KPC) antibodies and 90% biotinylated 20-mer guanine quadruplex oligonucleotides. A biosensor working electrode was conjugated with anti-*Klebsiella pneumoniae* carbapenemases enzyme (KPC) antibodies. A second biosensor working electrode was provided as a negative control. The sample collection unit was pre-filled with cefotaxame and nutrients. The sample collection unit was also provided with a lysis reservoir for delivering lysis reagents and a tab for releasing the lysis reagents to the sample collection unit. The assay begins by providing a sample to the sample collection unit and in some embodiments concentrating the sample as described in example 4. The cartridge was incubated at 35° for about 2.5 hours to produce KPC enzymes if the CP-CRE are viable and KPC producing. After incubation a tab was released to allow the lysis reagents to flow from the lysis reservoir to the sample. Other processes such as shaking the cartridge may be beneficial. After a few minutes the second tab was released to allow the lysate and KPC enzymes to flow from the sample collection unit to the signal amplification tag attachment unit where the KPC enzymes form multifunctional particle-KPC complexes. A magnetic field was applied to allow nonspecific materials and constituents to laterally flow past the biosensor working electrodes. Another tab is then pulled to remove the magnetic field and allow KPC to form sandwiches on the KPC working electrode. The cartridge is inserted into the potentiostat instrument and a peak electrical current is generated in proportional to the KPC concentration.

Example 11—Reusable Biosensor for Cumulative Detection. The Quantitative Immunoassay described in Example 2 was further evaluated by adding a conjugate reservoir in the signal amplification tag attachment unit. The conjugates contain quadruplex oligonucleotides which are reversible and can be retested. Each sample added to the sample collection unit would be provided with an unused set of conjugates to form multifunctional particle-*E. coli* O157:H7 complexes and subsequently signal amplification sandwich structures. After the first sample is processed a second sample and second set of conjugated would provide additional signal amplification sandwich structures to increase the cumulative signal as more *E. coli* O157:H7 is added from subsequent samples to the biosensor working electrode.

Example 12—Sanitize Pathogens After Detection. The Quantitative Immunoassay described in Example 2 was further evaluated by changing the conjugate's multifunctional particle from 1-micron solid polystyrene particles to 1-micron polystyrene shells filled with or encapsulating an antimicrobial agent or sanitizing chemical that can kill viable organisms. After the detection scan, a process or chemical is provided to release the antimicrobial agent or sanitizing chemical in order to kill the viable organisms.

What is claimed is:

1. A signal amplification sandwich structure for amplifying, detecting and/or quantifying an analyte in a fluid sample, wherein said structure comprises:
   (a) a first outer layer comprising a multifunctional particle conjugated with a plurality of a first analyte binding material, and the multifunctional particle is also conjugated on its outer structure or filled in its inner structure with a plurality of an electrochemically detectable oligonucleotide tag in greater amounts than said analyte in the inner layer;
   (b) an inner layer comprising said analyte; and
   (c) a second outer layer comprising a biosensor working electrode, or a sorbent situated near a biosensor working electrode, conjugated with a plurality of a second analyte binding material that is a matched pair with the first analyte binding material;

wherein:
   (i) said electrochemically detectable oligonucleotide tags are single-stranded, duplex or quadruplex, wherein said electrochemically detectable oligonucleotide tags are majority guanine ranging from 8 to 400 guanine nucleotides per tag;
   (ii) said multifunctional particles comprise one or more of structural materials, magnetic materials, optical materials, nuclear materials, radiological materials, quantum materials, biological materials, energetic materials, electrochemical materials, chemical materials, pharmaceutical materials, antibiotic materials, chemotherapy materials, antibodies, and combinations thereof, wherein the number of electrochemically detectable oligonucleotide tags per multifunctional particle ranges from $10^2$ to $10^{13}$, wherein the multifunctional particles are spherical and/or nonspherical, wherein the diameter of spherical multifunctional particles ranges from 0.05 to 400 micrometers, wherein the surface area of nonspherical multifunctional particles has an equivalent surface area of spherical multifunctional particles with ranges from 0.05 to 400 micrometers, and wherein the surface of the multifunctional particles is smooth, rough, porous, or extended with attachments to other particles;

(iii) said signal analyte amplification performance of said signal amplification sandwich structure can be tuned to meet the desired limit of detection by adjusting one or more of the following: the number of electrochemically detectable oligonucleotide tags per multifunctional particle; the number of guanines per electrochemically detectable oligonucleotide tag; the size of the multifunctional particle for delivering electrochemically detectable oligonucleotide tags or electrochemical materials; and the surface area of the multifunctional particle for conjugating electrochemically detectable oligonucleotide tags.

2. A method for amplifying, detecting and/or quantifying an analyte in a fluid sample comprising:
(a) providing the fluid sample that may contain non-specific materials and an analyte;
(b) providing multifunctional particle conjugates comprising a plurality of a multifunctional particle conjugated with a plurality of a first analyte binding material and also conjugated with a plurality of an electrochemically detectable oligonucleotide tag in greater amounts than said analyte to create multifunctional particle-analyte complexes if said analyte is present;
(c) providing a biosensor working electrode, or a sorbent situated near a biosensor working electrode, conjugated with a plurality of a second analyte binding material that is a matched pair with the first analyte binding material to create signal amplification sandwich structures if said analyte is present; and
(d) providing an electrochemical detection technique that produces a peak electrochemical signals on the biosensor working electrode, in proportion to the quantity of said analyte if said analyte is present in the fluid sample;
wherein said method employs the steps to form one or more signal amplification sandwich structures for amplifying, detecting and/or quantifying the analyte in the fluid sample, wherein said structure is comprised of a first outer layer comprising a multifunctional particle conjugated with a plurality of a first analyte binding material, and the multifunctional particle is also conjugated on its outer structure or filled in its inner structure with a plurality of an electrochemically detectable oligonucleotide tag for signal amplification in greater amounts than said analyte in the inner layer, an inner layer comprising said analyte, and a second outer layer comprising a biosensor working electrode, or a sorbent situated near a biosensor working electrode, conjugated with a plurality of a second analyte binding material for binding said analyte that is a matched pair with the first analyte binding material;
wherein:
(i) said electrochemically detectable oligonucleotide tags are single-stranded, duplex or quadruplex, wherein said oligonucleotide tags are majority guanine ranging from 8 to 400 guanine nucleotides per tag;
(ii) said multifunctional particles comprise one or more of structural materials, magnetic materials, optical materials, nuclear materials, radiological materials, quantum materials, biological materials, energetic materials, electrochemical materials, chemical materials, pharmaceutical materials, antibiotic materials, chemotherapy materials, antibodies, and combinations thereof, wherein the number of electrochemically detectable oligonucleotide tags per multifunctional particle ranges from $10^2$ to $10^{13}$, wherein the multifunctional particles are spherical and/or nonspherical, wherein the diameter of spherical multifunctional particles ranges from 0.05 to 400 micrometers, wherein the surface area of nonspherical multifunctional particles has an equivalent surface area of spherical multifunctional particles with ranges from 0.05 to 400 micrometers, and wherein the surface of the multifunctional particles is smooth, rough, porous, or extended with attachments to other particles;

(iii) said signal analyte amplification performance of said signal amplification sandwich structure can be tuned to meet the desired limit of detection by adjusting one or more of the following parameters: the number of electrochemically detectable oligonucleotide tags per multifunctional particle; the number of guanines per electrochemically detectable oligonucleotide tag; the size of the multifunctional particle for delivering electrochemically detectable oligonucleotide tags or electrochemical materials; and the surface area of the multifunctional particle for conjugating electrochemically detectable oligonucleotide tags.

3. The method of claim 2 is used for amplifying, detecting and/or quantifying one or more analytes in a fluid sample, and diagnosing a disease, outbreak or condition, wherein said method further comprises before step (a):
(a1) providing an artificial intelligence assessment system to recommend actions for assessment of the disease, outbreak or condition;
and after step (d):
(d1) providing one or more test results consisting of analyte quantities, non-bioanalyte and/or bioanalyte levels from other sources that may be associated with the disease, outbreak or condition;
(d2) providing an artificial intelligence diagnosis system to diagnose and recommend actions for treatment of the disease, outbreak or condition; and
(d3) providing an artificial intelligence learning system to incorporate improvements, additions and modifications to the artificial intelligence systems and its constituents.

4. The method of claim 3, wherein the artificial intelligence assessment system in step (a1) and the artificial intelligence diagnosis system in step (d2) each comprise:
(1) an input system to receive patient information, symptoms, medical histories, allergies, immune responses, predispositions, and genetic information, biomarker levels and states, chemical levels and states, and to import one or more of images, signals and data from sensors, devices, instruments, actuators, smart phones, computers, databases, records, files, other assays including optical assays and optical detection instruments, electrochemical assays and electrochemical detection instruments, direct detection instruments, other detection methods and/or combinations thereof;
(2) a knowledge base comprising one or more of deterministic rules, mathematical models, concentration formulas, image recognition, pattern recognition, Boolean logic, algorithms, standards, changes of bioanalyte and non-bioanalyte parameters over time, rates, temperature, environmental conditions, phases, reactions, events, treatments, remedies, guidelines, regulations, standards, norms, diseases, outbreaks, conditions, disease-specific, information, outbreak-specific information, condition-specific information, and/or combinations thereof; and (3) an inference engine to interpret inputs, data knowledge base in order to provide recommended actions to complete the assessment and/or diagnosis; and/or wherein the non-bioanalyte and bioanalyte parameters in step (d1) include:

one or more of patient information, symptoms, medical histories, allergies, immune responses, predispositions, and genetic information, biomarker levels and states, chemical levels and states, images, signals and data from sensors, devices, instruments, actuators, smart phones, computers, databases, records, files, other assays including optical assays and optical detection instruments, electrochemical assays and electrochemical detection instruments, direct detection instruments, other detection methods and/or combinations thereof, deterministic rules, mathematical models, concentration formulas, image recognition, pattern recognition, Boolean logic, algorithms, standards, changes of bioanalytes and/or non-bioanalyte parameters over time, rates and temperature, environmental conditions, phases, reactions, events or combination thereof; and/or wherein the diagnosis and recommended actions from step (d3) include:

one or more of positive outcome, negative outcome, probabilistic outcome, undetermined outcome, alternative outcome, analyte level, do nothing, specific treatment, additional test, other action, and combinations thereof.

5. The method of claim 2, wherein the electrochemical detection technique in step (d) further comprises:

(e) said analyte is determined to be present when the peak electrochemical signal in step (d) exceeds a negative control cut-off signal determined from a negative control electrode as a mean of multiple peak negative control scans plus 3 standard deviations of the variance;

(f) the quantity of said analyte is determined by comparing the generated peak electrochemical signal from an associated electrochemically detectable oligonucleotide tag in step (d) with predetermined signals from known quantities of said analyte.

6. The method of claim 2, wherein said method further comprises one or more of:

(g) the fluid sample in step (a) is filtered to increase the concentration of analytes;

(h) the fluid sample in step (a) is exposed to antimicrobials or chemicals to produce antimicrobial-resistant protein and/or nucleic acid analytes;

(i) the fluid sample in step (a) is provided with lysis reagents to release protein and/or nucleic acid analytes;

(j) the multifunctional particle-analyte complexes in step (b) are magnetically immobilized and the non-magnetically immobilized constituents of the fluid sample which may contain nonspecific materials are flushed away; and (k) the fluid sample in step (a) is treated by one or more of the following: a membrane, a chemical adherent, a disaggregation technique involving one or more of a chemical surfactant, sonication, and hydrodynamic cavitation to disaggregate clumps potentially containing said analytes, and a dilution technique to provide multiple concentrations of samples that can be separately processed as a larger range to quantify said analyte.

7. The method of claim 3, wherein said method for amplifying, detecting and/or quantifying one or more analytes in a fluid sample, and diagnosing a disease, outbreak or condition, omits (d1).

8. The structure of claim 1, wherein the multifunctional particle comprises an exterior surface or coating in that is selected from the group consisting of styrene, polystyrene, polymer, agarose, dextran, glass, ceramic, composite material, and combinations thereof; and the first analyte binding material in (a) and the second analyte binding material in (c) are selected from the group consisting of antibodies, monoclonal antibodies, polyclonal antibodies, amino acids, peptides, proteins, haptens, nucleic acids, oligonucleotides, DNA, RNA, aptamers, matched pairs thereof and combinations thereof.

9. A device for amplifying, detecting and/or quantifying an analyte in a fluid sample, and diagnosing a disease, outbreak or condition, wherein said device comprises:

(a) one or more device units comprising:

(a1) a sample collection unit to collect said fluid sample that may contain non-specific materials and an analyte, (a2) a signal amplification tag attachment unit for providing multifunctional particle conjugates comprising a plurality of a multifunctional particle conjugated with a plurality of a first analyte binding material and is also conjugated with a plurality of an electrochemically detectable oligonucleotide tag in greater amounts than said analyte to create multifunctional particle-analyte complexes if said analyte is present, (a3) a signal amplification tag capture unit configured for providing a biosensor working electrode, or a sorbent situated near the biosensor working electrode, conjugated with a plurality of a second analyte binding material that is a matched pair with the first analyte binding material to create signal amplification sandwich structures if said analyte is present, and (a4) an electrochemical detection unit for providing an electrochemical detection technique that produces a peak electrochemical signal on the biosensor working electrode, in proportion to the quantity of said analyte if said analyte is present in the fluid sample;

(b) optionally an artificial intelligence unit comprising:

(b1) an artificial intelligence assessment system configured to collect inputs and recommend actions for assessment using an assessment knowledge base, an assessment inference engine, and computer components, (b2) an artificial intelligence diagnosis system configured to collect inputs and recommend actions for diagnosis using a diagnosis knowledge base, a diagnosis inference engine, and computer components, (b3) an artificial intelligence learning system configured to store, process and improve the capabilities of the artificial intelligence assessment system and the artificial intelligence diagnosis system, and (c) optionally one or more units or interfaces that measure non-bioanalyte parameters and bioanalyte parameters;

wherein said device employs the device units to form one or more signal amplification sandwich structure for amplifying, detecting and/or quantifying an analyte in a fluid sample, wherein said structure comprises a first outer layer comprising a multifunctional particle conjugated with a plurality of a first analyte binding material, and the multifunctional particle is also conjugated on its outer structure or filled in its inner structure with a plurality of an electrochemically detectable oligonucleotide tag for signal amplification in greater amounts than said analyte in the inner layer, an inner layer comprising said analyte, and a second outer layer comprising a biosensor working electrode, or a sorbent situated near a biosensor working electrode, conjugated with a plurality of a second analyte binding material that is a matched pair with the first analyte binding material;

wherein:

(i) said electrochemically detectable oligonucleotide tags are single-stranded, duplex or quadruplex, wherein said oligonucleotide tags are majority guanine ranging from 8 to 400 guanine nucleotides per tag;

(ii) said multifunctional particles comprise one or more of structural materials, magnetic materials, optical materials, nuclear materials, radiological materials, quantum materials, biological materials, energetic materials, electrochemical materials, chemical materials, pharmaceutical materials, antibiotic materials, chemotherapy materials, antibodies, and combinations thereof, wherein the number of electrochemically detectable oligonucleotide tags per multifunctional particle ranges from $10^2$ to $10^{13}$, wherein the multifunctional particles are spherical and/or nonspherical, wherein the diameter of spherical multifunctional particles ranges from 0.05 to 400 micrometers, wherein the surface area of nonspherical multifunctional particles has an equivalent surface area of spherical multifunctional particles with ranges from 0.05 to 400 micrometers, and wherein the surface of the multifunctional particles is smooth, rough, porous, or extended with attachments to other particles;

(iii) said signal analyte amplification performance of said signal amplification sandwich structure can be tuned to meet the desired limit of detection by adjusting one or more of the following parameters: the number of electrochemically detectable oligonucleotide tags per multifunctional particle; the number of guanines per electrochemically detectable oligonucleotide tag; the size of the multifunctional particle for delivering electrochemically detectable oligonucleotide tags or electrochemical materials; and the surface area of the multifunctional particle for conjugating electrochemically detectable oligonucleotide tags.

10. The device of claim 9, wherein at least one of the device units is configured to comprise
(a) one or more test cartridges or panels comprising portions of the device units for processing one or more fluid samples; and
(b) an instrument comprising portions of a device unit for operating the one or more test cartridges or panels to process one or more fluid samples.

11. The device of claim 10, wherein the instrument comprises one or more of electrical systems, mechanical systems, electrochemical signal generation capability, electrochemical measurement capability, mathematical models, user interface, display, multiplexer, processor, memory, communications, pump, compressor, magnetic field, physical separation, filtering, magnetic separation, optical reading, storing and delivering chemicals and reagents, lysing capability, heating capability, cooling capability, releasing capability and the capability to deliver materials.

12. The device of claim 10, wherein the instrument is selected from the group consisting of a handheld device, a point-of-care device, a point-of-use device, a lateral flow device, a laboratory device, an in vitro device, and a portable device.

13. The device of claim 10, wherein the instrument is configured as:
(a) a plug-in instrument selected from the group consisting of a device plug-in, adapter, printed circuit board, semiconductor, wearable device, and an embedded device, or
(b) a standalone instrument selected from the group consisting of a smart phone, computer, tablet, medical device, communications device, and a testing device.

14. The device of claim 10, wherein the instrument is configured as:
(a) a field instrument selected from the group consisting of inline meter, field analyzer, and networked sensing node, and is further configured to accommodate
(b) a sample source that contains one or more samples selected from the group consisting of a tank, a concentrator, an environmental source, an industrial source, a water source, a medical source, a system to liquefy solid samples, a system to liquefy gas samples, and further comprises
(c) one or more of a sample delivery system, a manifold, one or more test cartridges contained in a panel, and capabilities to operate, house and/or coordinate the functions of one or more ancillary instruments, devices and interfaces required to extract samples, process samples, concentrate samples, measure analytes, transmit test results and deliver secondary materials or perform additional functions required for the multifunctional particle results.

15. The device of claim 10, wherein one or more of said test cartridge comprise one or more of a biosensor cartridge, microfluidics, a lateral flow test strip, a lateral flow device cartridge, an embedded cartridge, a wearable cartridge, a patch, a microarray cartridge, smart material, and a smart package.

16. The device of claim 10, wherein the test cartridge comprises:
(a) a sample collection unit comprising a sample port for collecting said fluid sample and a sample pad or reservoir for removing fluid,
(b) a signal amplification tag attachment unit comprising a conjugation pad or reservoir for forming a first outer layer and inner layer of signal amplification sandwich structures,
(c) a signal amplification tag capture unit comprising a membrane or reservoir for enabling the fluid sample, the signal amplification sandwich structures, non-specific materials and unattached multifunctional particles to flow from the signal amplification attachment unit to a biosensor working electrode, or a sorbent near a biosensor working electrode, conjugated with a plurality of a second analyte binding material for binding said analyte that is a matched pair with the first analyte binding material to form a second outer layer of signal amplification sandwich structures with the first outer layer and inner layer of signal amplification sandwich structures,
(d) an electrochemical detection unit with at least one biosensor working electrode configured to measure detection signals from the electrochemically detectable oligonucleotide tags contained on said signal amplification sandwich structures, (e) a wick pad or reservoir to remove excess fluid, non-specific materials and unattached multifunctional particles, and (f) a backing or structure, and a cartridge housing.

17. The device of claim 9, wherein said device further comprises one or more of a sample input reservoir for collecting large volume fluid samples, a filter for concentrating fluid samples, a pressure mechanism for forcing fluid sample through a filter, a pre-filter for removing large particles from the fluid sample, a magnetic field for magnetically separating conjugates from nonspecific materials, a lysis reservoir for delivering lysis reagents to the analytes, a conjugate reservoir for delivering conjugates, a membrane for passing conjugates and complexes, one or more biosensor working electrodes, a counter electrode, a reference electrode, a panel containing multiple biosensors or multiple test strips.

18. The structure of claim 1, or the method of claim 2, or the device of claim 9, 10, 13, 14, 15, 16 or 17, wherein the first outer layer comprises a multifunctional particle conjugated on its outer structure with a plurality of an oligonucleotide in greater amounts than said analyte in the inner layer and comprising (a) an electrochemically detectable sequence, (b) a linker, and (c) a first analyte binding material comprising a nucleic acid sequence for binding a nucleic acid analyte inner layer or an aptamer sequence for binding a protein analyte inner layer.

19. The structure of claim 1, or the method of claim 2, or the device of claim 9, 10, 13, 14, 15, 16 or 17 wherein (a) the majority of the nucleotides within said electrochemically detectable oligonucleotide tags are guanine and an electrochemical detection technique produces guanine oxidation signals; or (b) the majority of the nucleotides within said quadruplex electrochemically detectable oligonucleotide tags are guanine with at least 4 guanine in a square tetrad structure and an electrochemical detection technique produces 8-oxoguanine signals; or (c) the majority of the nucleotides within said electrochemically detectable oligonucleotide tags are not guanine but instead are adenine and an electrochemical detection technique produces adenine oxidation signals; or (d) wherein the majority of the nucleotides within said quadruplex electrochemically detectable oligonucleotide tags are not guanine but instead are adenine with at least 4 adenine in a square tetrad structure and an electrochemical detection technique produces 8-oxoadenine signals; or (e) the majority of the nucleotides within said electrochemically detectable oligonucleotide tags are not guanine but instead are thymine and an electrochemical detection technique produces thymine oxidation signals; or (f) wherein the majority of the nucleotides within said quadruplex electrochemically detectable oligonucleotide tags are not guanine but instead are thymine with at least 4 thymine in a square tetrad structure and an electrochemical detection technique produces 8-oxothymine signals; or (g) the majority of the nucleotides within said electrochemically detectable oligonucleotide tags are not guanine but instead are cytosine and an electrochemical detection technique produces cytosine oxidation signals; or (h) wherein the majority of the nucleotides within said quadruplex electrochemically detectable oligonucleotide tags are not guanine but instead are cytosine with at least 4 cytosine in a square tetrad structure and an electrochemical detection technique produces 6-oxocytosine signals; or (i) wherein one or more nucleotide sequences and/or one or more quadruplex tetrads can be formed on different segments of the same electrochemically detectable oligonucleotide tag and produce multiple signals from the oxidation of one or more different nucleotides and/or oxo derivatives.

20. The device of claim 9, wherein the artificial intelligence unit comprises one or more of assessment system, assessment knowledge base, assessment inference engine, diagnosis system, diagnosis knowledge base, diagnosis inference engine, learning system, units or interfaces that measure non-bioanalyte parameters and bioanalyte parameters, computer systems, central processing units, memories, databases, user interfaces, communications interfaces, communications modules, device interfaces, device modules, image recognition interfaces, image recognition modules, instrument interfaces, instrument modules, sensor interfaces, sensors, voice interface, voice module, software and devices to operate the interfaces and modules, other capabilities that would facilitate artificial intelligence processing and combinations thereof.

21. The structure of claim 1, or the method of claim 2, or the device of claim 9, wherein the signal amplification sandwich structure is used for amplifying, detecting and/or quantifying one or more different analytes in the fluid sample wherein:

i. multiple sets of multifunctional particle conjugates are provided where each set comprises a plurality of a multifunctional particle conjugated with a plurality of a first analyte binding material and is also conjugated with a plurality of an electrochemically detectable oligonucleotide tag in greater amounts than said one or more different analytes to create multifunctional particle-analyte complexes if one or more different analytes are present;

ii. multiple sets of biosensor working electrodes, and/or multiple sorbents situated near multiple biosensor working electrodes, are conjugated with a plurality of a second analyte binding material that is a matched pair with the first analyte binding material to create signal amplification sandwich structures if one or more different analytes are present; and iii. optionally providing an electrochemical detection technique that produces peak electrochemical signals on each biosensor working electrode, in proportion to the quantity of one or more different analytes present in the fluid sample;

wherein multiple different analytes can be measured simultaneously from the said fluid sample: (i) as multiple different analytes measured individually at unique biosensor working electrodes associated with each different analyte wherein each said analyte is associated with (a) a unique multifunctional particle conjugated with a plurality of a first analyte binding material for binding the analyte, and the multifunctional particle is also conjugated on its outer structure or filled in its inner structure with a plurality of an electrochemically detectable oligonucleotide tag in greater amounts than said analyte in the inner layer, wherein the majority of nucleotides within said oligonucleotide tags are guanine and when a unique electrochemically detectable oligonucleotide tag is used to amplify, detect and/or quantify said analyte, said electrochemically detectable oligonucleotide tag comprises additional nucleotides selected from the group of nucleotides consisting of guanine, adenine, thymine, and cytosine; and (b) a unique biosensor working electrode, or a sorbent situated near a biosensor working electrode, conjugated with a plurality of a second analyte binding material for binding said analyte that is a matched pair with the first analyte binding material, or conjugated with a plurality of a unique oligonucleotide recognition probe to bind or hybridize with the complementary electrochemically detectable oligonucleotide tag of said analyte to determine the quantity of said analyte; or (ii) as multiple different analytes measured as a group at a common biosensor working electrode associated with any analyte in said group of multiple different analytes wherein each said analyte in said group is associated with (a) a unique multifunctional particle conjugated with a plurality of a first analyte binding material for binding the analyte, and the multifunctional particle is also conjugated on its outer structure or filled in its inner structure with a plurality of a common electrochemically detectable oligonucleotide tag in greater amounts than any said analyte in said group in the inner layer, wherein the majority of nucleotides within said oligonucleotide tags are guanine and when a unique electrochemically detectable oligonucleotide tag is used to amplify, detect and/or quantify any analyte in said group of analytes, said electrochemically detectable oligonucleotide tag comprises additional nucleotides selected from the group of nucleotides consisting of guanine, adenine, thymine and cytosine; and (b) a unique biosensor working electrode, or a sorbent situated near a biosensor working electrode, conjugated with a plurality of a second analyte binding material for binding said any analyte in said group that is a matched pair with the first analyte binding material of any analyte in said group, or conjugated with a plurality of a unique oligonucleotide recognition probe to bind or hybridize with the common complementary electrochemically detectable oligonucleotide tag for any said analyte in said group to determine the combined quantity for all said analytes in said group.

* * * * *

```
SEQUENCE LISTING

<160> NUMBER OF SEQ ID NOS: 5

<210> SEQ ID NO 1
<211> LENGTH: 12
<212> TYPE: DNA
<213> ORGANISM: Artificial sequence
<220> FEATURE:
<223> OTHER INFORMATION: Synthesized oligonucleotide rich in
      electrochemically detectable guanine to act as a tag for
      amplifying analyte detection signals
<220> FEATURE:
<221> NAME/KEY: Tag
<222> LOCATION: (1)..(12)
<223> OTHER INFORMATION: single-stranded polyguanine detection sequence
<220> FEATURE:
<221> NAME/KEY: Tag
<222> LOCATION: (1)..(12)
<223> OTHER INFORMATION: Single-stranded polyguanine detection sequence
<220> FEATURE:
<221> NAME/KEY: Tag
<222> LOCATION: (1)..(12)
<223> OTHER INFORMATION: Single-stranded polyguanine detection sequence

<400> SEQUENCE: 1
gggggggggg gg                                                          12

<210> SEQ ID NO 2
<211> LENGTH: 12
<212> TYPE: DNA
<213> ORGANISM: Artificial sequence
<220> FEATURE:
<223> OTHER INFORMATION: Synthesized oligonucleotide rich in
      electrochemically detectable guanine to act as a tag for
      amplifying analyte detection signals
<220> FEATURE:
<221> NAME/KEY: Ligand
<222> LOCATION: (1)..(12)
<223> OTHER INFORMATION: Analyte binding material

<400> SEQUENCE: 2
atgggtgggt aa                                                          12

<210> SEQ ID NO 3
<211> LENGTH: 12
<212> TYPE: DNA
<213> ORGANISM: Artificial sequence
<220> FEATURE:
<223> OTHER INFORMATION: Synthesized oligonucleotide rich in
      electrochemically detectable guanine to act as a tag for
      amplifying analyte detection signals
<220> FEATURE:
<221> NAME/KEY: Quadruplex
<222> LOCATION: (1)..(12)
<223> OTHER INFORMATION: Polyguanine detection sequence assembled into
      guanine quadruplex
```

```
<400> SEQUENCE: 3
gggggggggg gg                                                              12

<210> SEQ ID NO 4
<211> LENGTH: 24
<212> TYPE: DNA
<213> ORGANISM: Artificial sequence
<220> FEATURE:
<223> OTHER INFORMATION: Synthesized oligonucleotide rich in
      electrochemically detectable guanine to act as a tag for
      amplifying analyte detection signals
<220> FEATURE:
<221> NAME/KEY: Quadruplex
<222> LOCATION: (1)..(12)
<223> OTHER INFORMATION: Quadruplex detection sequence
<220> FEATURE:
<221> NAME/KEY: Ligand
<222> LOCATION: (13)..(24)
<223> OTHER INFORMATION: Analyte binding sequence

<400> SEQUENCE: 4
gggggggggg ggatgggtgg gtaa                                                 24

<210> SEQ ID NO 5
<211> LENGTH: 81
<212> TYPE: DNA
<213> ORGANISM: Artifical sequence
<220> FEATURE:
<221> NAME/KEY: Linker
<222> LOCATION: (1)..(3)
<223> OTHER INFORMATION: Linker between biotin and quadruplex
<220> FEATURE:
<221> NAME/KEY: Quadruplex
<222> LOCATION: (4)..(23)
<223> OTHER INFORMATION: Quadruplex tag
<220> FEATURE:
<221> NAME/KEY: Linker
<222> LOCATION: (24)..(32)
<223> OTHER INFORMATION: Linker between quadruplex tag and analyte
      binding material
<220> FEATURE:
<221> NAME/KEY: Ligand
<222> LOCATION: (33)..(81)
<223> OTHER INFORMATION: Analyte binding material

<400> SEQUENCE: 5 ttagggggg gggggggggg gggttatttt tccattatta ggtcagccat tgttgcttgc           60
catgcgactc cgccttttt t                                                     81
```